US008883721B2

(12) United States Patent
Bowers et al.

(10) Patent No.: US 8,883,721 B2
(45) Date of Patent: Nov. 11, 2014

(54) METHODS OF INHIBITING THE GHRELIN/GROWTH HORMONE SECRETATOGUE RECEPTOR PATHWAY AND USES THEREOF

(75) Inventors: Cyril Y. Bowers, New Orleans, LA (US); David H. Coy, New Orleans, LA (US); Simon J. Hocart, New Orleans, LA (US); Gloria S. Tannenbaum, Hampstead (CA)

(73) Assignees: McGill University, Montreal (CA); The Administrators of the Tulane Educational Fund, New Orleans, LA (US)

( * ) Notice: Subject to any disclaimer, the term of this patent is extended or adjusted under 35 U.S.C. 154(b) by 130 days.

(21) Appl. No.: 13/320,408

(22) PCT Filed: May 12, 2010

(86) PCT No.: PCT/US2010/034570
§ 371 (c)(1),
(2), (4) Date: Feb. 3, 2012

(87) PCT Pub. No.: WO2010/132580
PCT Pub. Date: Nov. 18, 2010

(65) Prior Publication Data
US 2012/0135918 A1     May 31, 2012

Related U.S. Application Data

(60) Provisional application No. 61/177,400, filed on May 12, 2009.

(51) Int. Cl.
| | | |
|---|---|---|
| A61K 38/08 | (2006.01) | |
| A61K 38/10 | (2006.01) | |
| C07K 7/06 | (2006.01) | |
| C07K 7/08 | (2006.01) | |
| A61K 31/00 | (2006.01) | |
| A61K 45/06 | (2006.01) | |
| A61K 31/404 | (2006.01) | |
| A61K 38/16 | (2006.01) | |
| A61K 38/25 | (2006.01) | |

(52) U.S. Cl.
CPC ............ *A61K 38/08* (2013.01); *A61K 31/00* (2013.01); *A61K 45/06* (2013.01); *A61K 31/404* (2013.01); *A61K 38/16* (2013.01); *A61K 38/25* (2013.01); *A61K 38/10* (2013.01)
USPC .............. 514/4.8; 514/5.3; 514/6.9; 514/7.3; 514/21.5; 514/21.6; 514/21.7; 514/21.8; 530/327; 530/328; 530/329; 530/330

(58) Field of Classification Search
None
See application file for complete search history.

(56) References Cited

U.S. PATENT DOCUMENTS

| | | | |
|---|---|---|---|
| 7,250,399 B2 | 7/2007 | Bowers et al. | |
| 7,385,026 B1 * | 6/2008 | Kangawa et al. | 530/324 |
| 2005/0272648 A1 * | 12/2005 | Dong et al. | 514/12 |
| 2006/0089404 A1 * | 4/2006 | Desai et al. | 514/456 |
| 2006/0142397 A1 * | 6/2006 | Junien et al. | 514/635 |
| 2007/0021331 A1 | 1/2007 | Fraser et al. | |
| 2009/0069245 A1 | 3/2009 | Bowers et al. | |
| 2010/0086955 A1 * | 4/2010 | Harran et al. | 435/15 |
| 2011/0257086 A1 | 10/2011 | Cole et al. | |

FOREIGN PATENT DOCUMENTS

| | | | |
|---|---|---|---|
| WO | WO 0107475 A1 * | 2/2001 | |
| WO | 2004/009124 A2 | 1/2004 | |
| WO | WO 2005110463 A1 * | 11/2005 | |
| WO | WO 2007127457 A2 * | 11/2007 | |
| WO | WO 2010039461 A2 * | 4/2010 | |

OTHER PUBLICATIONS

Petersen et al. In Vivo Characterization of High Basal Signaling from the Ghrelin Receptor. Endocrinology. Nov. 2009, vol. 150, No. 11, pp. 4920-4930.*
Bowers, C. Y., et al. "The role of GHS/Ghrelin in Feeding and Body Composition. Obesity and Energy Metabolism: research and Clinical Applications" (Eds) Conn PM and Donohoue P.The Humans Press, 2007.
Bowers, C. Y., et al. "Biochemistry of growth hormone secretagogue molecules, In: Fat Loss, Wasting and Cachexia in Medicine" (Ed) Schuster M and Mantovani G, Springer Verlag, Chapter 5.7, p. 219-234, 2006.
Gelling, R.W., et al. "Effect of uncontrolled diabetes on plasma ghrelin concentrations and ghrelin-induced feeding." Endocrinology 2004; 145:4575-4582.
Gualillo, O., et al. "Introducing GOAT: a target for obesity and anti-diabetic drugs?" Trends Pharmacol. Sci., Aug. 2008, vol. 29(8):398-401.
Inui, A., et al., "appetite and growth-The emerging role of the stomach as an endocrine organ." FASEB Journal 2004; 18:439-456.
Korbonits, M, et al. "Ghrelin-a hormone with multiple functions." Neuroendocrinology 2004; 25:27-68.
Laferrere B. et al., "Growth hormone releasing peptide-2 (GHRP-2), like ghrelin, increases food intake in healthy men." J Clin Endocrinol Metab 2005; 90:611-614.

(Continued)

*Primary Examiner* — Jeffrey E Russel
(74) *Attorney, Agent, or Firm* — Nixon Peabody LLP.

(57) ABSTRACT

The invention provides methods for treatment, prevention or management of obesity, obesity related disorders, diabetes mellitus, and metabolic syndrome in a subject by administering a ghrelin O-acyltransferase (GOAT) inhibitor and/or a ghrelin receptor antagonist to the subject. The invention also provides ghrelin receptor antagonists of formula (VII): $A^{11}$-$A^{12}$-$A^{13}$-Gly-Ser-$A^{14}$-Phe-Leu-$A^{15}$-$A^{16}$-$A^{17}$-$A^{18}$ (SEQ ID NO: 93), wherein each of $A^{11}$, $A^{12}$, and $A^{13}$ is independently absent, an amino acid, or an amino protecting group; each of $A^{15}$, $A^{16}$, $A^{17}$, and $A^{18}$ is independently absent or an amino acid; and $A^{14}$ is a serine conjugated with a —(O)$C_1$-$C_{20}$alky or a diaminopropionic acid conjugated with a —C(O)$C_1$-$C_{20}$alkyl group, provided that at least one of $A^{11}$, $A^{12}$, or $A^{13}$ is present.

15 Claims, 12 Drawing Sheets

(56) References Cited

OTHER PUBLICATIONS

Laferrere B., et al. "Obese subjects respond to the stimulatory effect of the ghrelin agonist Growth Hormone Releasing Peptide-2 (GHRP-2) on food intake." Obesity 14(6):1056-63, 2006.
Petersen P. S., et al. "Effect of icv infusion of the ghrelin receptor selective inverse agonist [DArg1,DPhe5, DTrp7,9 Leu11]-Sub P on body weight gain in rats." Keystone Symposium Gut Hormone and Other Regulators of Appetite, Satiety and Energy Expenditure Mar. 2-7, 2006, p. 53.
Tannenbaum, G.S., et al. "Ghrelin and growth hormone neuroendocrine axis. In: Brain Somatic Cross-Talk and the Central Control of Metabolism." Eds. C Kordon et al. 2003; Springer-Verlag, Berlin/Heidelberg p. 65-80.
Tannenbaum, G.S., et al. "Interrelationship between the novel peptide ghrelin and somatostatin/GHRH in regulation of pulsatile growth hormone secretion." Endocrinology 2003; 144:967-974.
Van Der Lely, A.J., et al. "Biological, physiological, pathophysiological and pharmacological aspects of ghrelin." Endocrine Reviews 2004; 25:426-457.
Wortley, K.E., et al. "Absence of ghrelin protects against early-onset obesity." J Clin Invest 2005; 115:3573-3578.
Wren A.M., et al. "Ghrelin enhances appetite and increases food intake in humans." J Clin Endocrinol Metab 2001; 86:5992-5995.
Yang, J., et al. "Inhibition of ghrelin O-acyltransferase (GOAT) by octanoylated pentapeptides" Proc Natl Acad Sci USA, Aug. 5, 2008, vol. 105(31)10750-10755.
Zigman, K.M., et al. "Mice lacking ghrelin receptors resist the development of diet induced obesity." J Clin Invest 2005; 115:3564-3572.
Betts et al., "Amino acid properties and consequences of substitutions" Bioinformatics for Geneticists, Barnes et al., John Wiley & Sons pp. 297-327 (2003).
Bitar et al., Effects of Substance P/Bombesin antagonists on the release of growth hormone by GHRP and GHRH. Biochem Biophy Res Comm 180(1):156-161, 1991.
Bodart et al., CD36 mediates cardiovascular action of growth hormone-releasing peptides in the heart. Circ Res 2002; 90:844-49.
Bowers, Growth Hormone Releasing Peptides (GHRPs). In: Handbook of Physiology, Eds. J Kostyo, H Goodman 1999; Oxford University Press, New York, p. 267-297.
Bowers, Octanoyl ghrelin is hypothalamic rooted. Endocrinology 146:2508-9, 2005.
Bowers, Unnatural growth hormone-releasing peptide begets natural ghrelin. J Clin Endocrinol Metab 2001; 86:1464-1469.
Camina JP. Cell biology of the ghrelin receptor. J Neuroendocrinol 2006; 18:65-76.
Holst et al., Common structural basis for constitutive activity of the ghrelin receptor family. J Biol Chem 2004; 279:53806-53817.
Holst et al., High constitutive signaling of the ghrelin receptor-identification of a potent inverse agonist. Mol. Endocrinol 2003; 17 (11):2201-10.
Holst et al., Identification of an efficacy switch region in the ghrelin receptor responsible for interchange between agonism and inverse agonism. Journal Biol Chem 282:15799, 2007.
Kojima et al., Ghrelin is a growth-hormone-releasing acylated peptide from stomach. Nature 1999; 402:656-60.
Matsumoto et al., Structure-activity relationship of ghrelin: Pharmacological study of ghrelin peptides. Biochemical and Biophysical Research Communications, 287:142-146 (2001).
Sethumadhaven et al., Demonstration and characterization of the specific binding of growth hormone-releasing peptide to rat anterior pituitary and hypothalamic membranes. Biochem Biophy Res Comm 178(1):31-37, 1991.
Veeraragavan et al., Growth hormone releasing peptide (GHRP) binding to porcine anterior pituitary and hypothalamic membranes. Life Sciences 50:1149-1155, 1992.
Yang et al., Identification of the acyltransferase that octanoylates ghrelin, an appetite-stimulating peptide hormone.Cell. Feb. 8, 2008;132(3):387-96.
Yang et al., Inhibition of ghrelin O-acyltransferase (GOAT) by octanoylated pentapeptides.Proc Natl Acad Sci U S A. Aug. 5, 2008;105(31):10750-5. Epub Jul. 31, 2008.
Zigman et al., Expression of ghrelin receptor mRNA in the rat and the mouse brain. J Comparative Neurology 2006; 494:528-548.

* cited by examiner

SEQUENCE LISTING

```
<160> NUMBER OF SEQ ID NOS: 98

<210> SEQ ID NO 1
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
```

```
<222> LOCATION: (3)..(3)
<223> OTHER INFORMATION: Ser(Oct)

<400> SEQUENCE: 1

Gly Ser Ser Phe Leu
1               5

<210> SEQ ID NO 2
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Dap(Oct)

<400> SEQUENCE: 2

Gly Ser Xaa Phe Leu
1               5

<210> SEQ ID NO 3
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Dap(Oct)
<220> FEATURE:
<223> OTHER INFORMATION: C-terminus amidated

<400> SEQUENCE: 3

Gly Met Ala Gly Ser Xaa Phe Leu Ser Pro Glu His
1               5                   10

<210> SEQ ID NO 4
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Dap(palmityl)
<220> FEATURE:
<223> OTHER INFORMATION: C-terminus amidated

<400> SEQUENCE: 4

Gly Met Ala Gly Ser Xaa Phe Leu Ser Pro Glu His
1               5                   10

<210> SEQ ID NO 5
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Ser(Des-Oct)
<220> FEATURE:
```

<223> OTHER INFORMATION: C-terminus amidated

<400> SEQUENCE: 5

Gly Ser Ser Phe Leu
1               5

<210> SEQ ID NO 6
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Dap(Oct)
<220> FEATURE:
<223> OTHER INFORMATION: C-terminus amidated

<400> SEQUENCE: 6

Gly Ser Xaa Phe Leu Ser Pro Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 7
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Dap(Oct)
<220> FEATURE:
<223> OTHER INFORMATION: C-terminus amidated

<400> SEQUENCE: 7

Gly Ser Xaa Phe Leu
1               5

<210> SEQ ID NO 8
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Ser(Des-Oct)
<220> FEATURE:
<223> OTHER INFORMATION: C-terminus amidated

<400> SEQUENCE: 8

Gly Ser Ser Phe
1

<210> SEQ ID NO 9
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:

```
<221> NAME/KEY: MOD_RES
<222> LOCATION: (3)..(3)
<223> OTHER INFORMATION: Ser(Des-Oct)
<220> FEATURE:
<223> OTHER INFORMATION: C-terminus amidated

<400> SEQUENCE: 9

Gly Ser Ser Phe Leu Ser Pro Glu His Gln Arg Val Gln Gln Arg Lys
1               5                   10                  15

Glu Ser

<210> SEQ ID NO 10
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Ser(Des-Oct)
<220> FEATURE:
<223> OTHER INFORMATION: C-terminus amidated

<400> SEQUENCE: 10

Gly Ser Ser Phe Leu Ser Pro Glu His Gln Arg Val Gln Gln Arg Lys
1               5                   10                  15

Glu Ser Lys Lys Pro Pro Ala Lys Leu Gln Pro Arg Tyr
            20                  25

<210> SEQ ID NO 11
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: D-Trp
<220> FEATURE:
<221> NAME/KEY: MOD_RES
<222> LOCATION: (3)..(3)
<223> OTHER INFORMATION: D-Lys
<220> FEATURE:
<221> NAME/KEY: MOD_RES
<222> LOCATION: (5)..(5)
<223> OTHER INFORMATION: D-Phe
<220> FEATURE:
<223> OTHER INFORMATION: C-terminus amidated

<400> SEQUENCE: 11

Tyr Trp Lys Trp Phe
1               5

<210> SEQ ID NO 12
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: D-Trp
<220> FEATURE:
<221> NAME/KEY: MOD_RES
<222> LOCATION: (5)..(5)
```

-continued

```
<223> OTHER INFORMATION: D-Phe
<220> FEATURE:
<223> OTHER INFORMATION: C-terminus amidated

<400> SEQUENCE: 12

Tyr Trp Lys Trp Phe
1               5

<210> SEQ ID NO 13
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: D-Trp
<220> FEATURE:
<221> NAME/KEY: MOD_RES
<222> LOCATION: (3)..(3)
<223> OTHER INFORMATION: D-Lys
<220> FEATURE:
<221> NAME/KEY: MOD_RES
<222> LOCATION: (5)..(5)
<223> OTHER INFORMATION: D-Phe
<220> FEATURE:
<223> OTHER INFORMATION: C-terminus amidated

<400> SEQUENCE: 13

His Trp Lys Trp Phe
1               5

<210> SEQ ID NO 14
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: D-Trp
<220> FEATURE:
<221> NAME/KEY: MOD_RES
<222> LOCATION: (3)..(3)
<223> OTHER INFORMATION: D-Lys
<220> FEATURE:
<221> NAME/KEY: MOD_RES
<222> LOCATION: (5)..(5)
<223> OTHER INFORMATION: D-Trp
<220> FEATURE:
<223> OTHER INFORMATION: C-terminus amidated

<400> SEQUENCE: 14

His Trp Lys Phe Trp
1               5

<210> SEQ ID NO 15
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: D-Trp
<220> FEATURE:
<221> NAME/KEY: MOD_RES
```

```
<222> LOCATION: (3)..(3)
<223> OTHER INFORMATION: D-Arg
<220> FEATURE:
<221> NAME/KEY: MOD_RES
<222> LOCATION: (5)..(5)
<223> OTHER INFORMATION: D-Phe
<220> FEATURE:
<223> OTHER INFORMATION: C-terminus amidated

<400> SEQUENCE: 15

His Trp Arg Trp Phe
1               5

<210> SEQ ID NO 16
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: D-Trp
<220> FEATURE:
<221> NAME/KEY: MOD_RES
<222> LOCATION: (3)..(3)
<223> OTHER INFORMATION: D-Lys
<220> FEATURE:
<221> NAME/KEY: MOD_RES
<222> LOCATION: (5)..(5)
<223> OTHER INFORMATION: D-Phe
<220> FEATURE:
<223> OTHER INFORMATION: C-terminus amidated

<400> SEQUENCE: 16

His Trp Lys Trp Phe Lys
1               5

<210> SEQ ID NO 17
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Desamino-Tyr
<220> FEATURE:
<221> NAME/KEY: MOD_RES
<222> LOCATION: (2)..(2)
<223> OTHER INFORMATION: D-Trp
<220> FEATURE:
<221> NAME/KEY: MOD_RES
<222> LOCATION: (5)..(5)
<223> OTHER INFORMATION: D-Phe
<220> FEATURE:
<223> OTHER INFORMATION: C-terminus amidated

<400> SEQUENCE: 17

Tyr Trp Ala Trp Phe
1               5

<210> SEQ ID NO 18
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

```
<221> NAME/KEY: MOD_RES
<222> LOCATION: (1)..(1)
<223> OTHER INFORMATION: Desamino-Tyr
<220> FEATURE:
<221> NAME/KEY: MOD_RES
<222> LOCATION: (2)..(2)
<223> OTHER INFORMATION: D-Trp
<220> FEATURE:
<221> NAME/KEY: MOD_RES
<222> LOCATION: (3)..(3)
<223> OTHER INFORMATION: D-Lys
<220> FEATURE:
<221> NAME/KEY: MOD_RES
<222> LOCATION: (5)..(5)
<223> OTHER INFORMATION: D-Phe
<220> FEATURE:
<223> OTHER INFORMATION: C-terminus amidated

<400> SEQUENCE: 18

Tyr Trp Lys Trp Phe
1               5

<210> SEQ ID NO 19
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Desamino-Tyr
<220> FEATURE:
<221> NAME/KEY: MOD_RES
<222> LOCATION: (2)..(2)
<223> OTHER INFORMATION: D-Trp
<220> FEATURE:
<221> NAME/KEY: MOD_RES
<222> LOCATION: (5)..(5)
<223> OTHER INFORMATION: D-Phe
<220> FEATURE:
<223> OTHER INFORMATION: C-terminus amidated

<400> SEQUENCE: 19

Tyr Trp Ser Trp Phe Lys
1               5

<210> SEQ ID NO 20
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Desamino-Tyr
<220> FEATURE:
<221> NAME/KEY: MOD_RES
<222> LOCATION: (2)..(2)
<223> OTHER INFORMATION: D-Trp
<220> FEATURE:
<221> NAME/KEY: MOD_RES
<222> LOCATION: (5)..(5)
<223> OTHER INFORMATION: D-Phe
<220> FEATURE:
<223> OTHER INFORMATION: C-terminus amidated

<400> SEQUENCE: 20

Tyr Trp Ser Trp Phe
1               5
```

```
<210> SEQ ID NO 21
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(3)
<223> OTHER INFORMATION: D-Trp
<220> FEATURE:
<223> OTHER INFORMATION: C-terminus amidated

<400> SEQUENCE: 21

His Trp Trp Phe Met
1               5

<210> SEQ ID NO 22
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(3)
<223> OTHER INFORMATION: D-Trp
<220> FEATURE:
<223> OTHER INFORMATION: C-terminus amidated

<400> SEQUENCE: 22

Tyr Trp Trp Phe Phe
1               5

<210> SEQ ID NO 23
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Gly Psi[CH2NH]
<220> FEATURE:
<221> NAME/KEY: MOD_RES
<222> LOCATION: (2)..(2)
<223> OTHER INFORMATION: D-Beta-Nal
<220> FEATURE:
<221> NAME/KEY: MOD_RES
<222> LOCATION: (5)..(5)
<223> OTHER INFORMATION: D-Phe
<220> FEATURE:
<223> OTHER INFORMATION: C-terminus amidated

<400> SEQUENCE: 23

Gly Xaa Ala Trp Phe Lys
1               5

<210> SEQ ID NO 24
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
```

```
<223> OTHER INFORMATION: Gly Psi[CH2NH]
<220> FEATURE:
<221> NAME/KEY: MOD_RES
<222> LOCATION: (2)..(2)
<223> OTHER INFORMATION: D-Beta-Nal
<220> FEATURE:
<221> NAME/KEY: MOD_RES
<222> LOCATION: (3)..(3)
<223> OTHER INFORMATION: D-Lys
<220> FEATURE:
<221> NAME/KEY: MOD_RES
<222> LOCATION: (5)..(5)
<223> OTHER INFORMATION: D-Phe
<220> FEATURE:
<223> OTHER INFORMATION: C-terminus amidated

<400> SEQUENCE: 24

Gly Xaa Lys Trp Phe Lys
1               5

<210> SEQ ID NO 25
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Ala
<220> FEATURE:
<221> NAME/KEY: MOD_RES
<222> LOCATION: (2)..(2)
<223> OTHER INFORMATION: D-Beta-Nal
<220> FEATURE:
<221> NAME/KEY: MOD_RES
<222> LOCATION: (3)..(3)
<223> OTHER INFORMATION: D-Lys
<220> FEATURE:
<221> NAME/KEY: MOD_RES
<222> LOCATION: (4)..(4)
<223> OTHER INFORMATION: D-Trp
<220> FEATURE:
<223> OTHER INFORMATION: C-terminus amidated

<400> SEQUENCE: 25

Ala Xaa Lys Trp Phe Lys
1               5

<210> SEQ ID NO 26
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: D-Beta-Nal
<220> FEATURE:
<221> NAME/KEY: MOD_RES
<222> LOCATION: (3)..(3)
<223> OTHER INFORMATION: D-Lys
<220> FEATURE:
<221> NAME/KEY: MOD_RES
<222> LOCATION: (5)..(5)
<223> OTHER INFORMATION: D-Phe
<220> FEATURE:
<223> OTHER INFORMATION: C-terminus amidated

<400> SEQUENCE: 26

His Xaa Lys Trp Phe Lys
```

```
<210> SEQ ID NO 27
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: D-Trp
<220> FEATURE:
<221> NAME/KEY: MOD_RES
<222> LOCATION: (4)..(4)
<223> OTHER INFORMATION: D-Lys
<220> FEATURE:
<221> NAME/KEY: MOD_RES
<222> LOCATION: (6)..(6)
<223> OTHER INFORMATION: D-Phe
<220> FEATURE:
<223> OTHER INFORMATION: C-terminus amidated

<400> SEQUENCE: 27

Ala His Trp Lys Trp Phe Lys
1               5

<210> SEQ ID NO 28
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Ala Psi[CH2NH]
<220> FEATURE:
<221> NAME/KEY: MOD_RES
<222> LOCATION: (2)..(2)
<223> OTHER INFORMATION: D-Beta-Nal
<220> FEATURE:
<221> NAME/KEY: MOD_RES
<222> LOCATION: (5)..(5)
<223> OTHER INFORMATION: D-Phe
<220> FEATURE:
<223> OTHER INFORMATION: C-terminus amidated

<400> SEQUENCE: 28

Ala Xaa Ala Trp Phe Lys
1               5

<210> SEQ ID NO 29
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Beta-Nal
<220> FEATURE:
<221> NAME/KEY: MOD_RES
<222> LOCATION: (4)..(4)
<223> OTHER INFORMATION: D-Phe
<220> FEATURE:
<223> OTHER INFORMATION: C-terminus amidated

<400> SEQUENCE: 29
```

```
Xaa Ala Trp Phe Ala
1               5

<210> SEQ ID NO 30
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Ala
<220> FEATURE:
<221> NAME/KEY: MOD_RES
<222> LOCATION: (2)..(2)
<223> OTHER INFORMATION: D-cyclohexyl-Ala
<220> FEATURE:
<221> NAME/KEY: MOD_RES
<222> LOCATION: (5)..(5)
<223> OTHER INFORMATION: D-Phe
<220> FEATURE:
<221> NAME/KEY: MOD_RES
<222> LOCATION: (6)..(6)
<223> OTHER INFORMATION: Nle
<220> FEATURE:
<223> OTHER INFORMATION: C-terminus amidated

<400> SEQUENCE: 30

Ala Ala Ala Phe Phe Xaa
1               5

<210> SEQ ID NO 31
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-cyclohexyl-Ala
<220> FEATURE:
<221> NAME/KEY: MOD_RES
<222> LOCATION: (4)..(4)
<223> OTHER INFORMATION: D-Trp
<220> FEATURE:
<223> OTHER INFORMATION: C-terminus amidated

<400> SEQUENCE: 31

Ala Ala Phe Trp Lys
1               5

<210> SEQ ID NO 32
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Ala
<220> FEATURE:
<221> NAME/KEY: MOD_RES
<222> LOCATION: (2)..(2)
<223> OTHER INFORMATION: D-Beta-Nal
<220> FEATURE:
<221> NAME/KEY: MOD_RES
<222> LOCATION: (5)..(5)
<223> OTHER INFORMATION: D-Thr
```

```
<220> FEATURE:
<223> OTHER INFORMATION: C-terminus amidated

<400> SEQUENCE: 32

Ala Xaa Ala Thr Thr Lys
1               5

<210> SEQ ID NO 33
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-cyclohexyl-Ala
<220> FEATURE:
<221> NAME/KEY: MOD_RES
<222> LOCATION: (4)..(4)
<223> OTHER INFORMATION: D-Phe
<220> FEATURE:
<223> OTHER INFORMATION: C-terminus amidated

<400> SEQUENCE: 33

Ala Ala Trp Phe
1

<210> SEQ ID NO 34
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Ala
<220> FEATURE:
<221> NAME/KEY: MOD_RES
<222> LOCATION: (2)..(2)
<223> OTHER INFORMATION: D-Beta-Nal
<220> FEATURE:
<221> NAME/KEY: MOD_RES
<222> LOCATION: (5)..(5)
<223> OTHER INFORMATION: D-Ala
<220> FEATURE:
<223> OTHER INFORMATION: C-terminus amidated

<400> SEQUENCE: 34

Ala Xaa Ala Ala Ala Lys
1               5

<210> SEQ ID NO 35
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Beta-Nal
<220> FEATURE:
<221> NAME/KEY: MOD_RES
<222> LOCATION: (4)..(4)
<223> OTHER INFORMATION: D-Phe
<220> FEATURE:
<223> OTHER INFORMATION: C-terminus amidated
```

```
<400> SEQUENCE: 35

Xaa Ala Trp Phe Leu
1               5

<210> SEQ ID NO 36
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: D-Trp
<220> FEATURE:
<221> NAME/KEY: MOD_RES
<222> LOCATION: (5)..(5)
<223> OTHER INFORMATION: D-Phe
<220> FEATURE:
<223> OTHER INFORMATION: C-terminus amidated

<400> SEQUENCE: 36

His Trp Phe Trp Phe Lys
1               5

<210> SEQ ID NO 37
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Ala
<220> FEATURE:
<221> NAME/KEY: MOD_RES
<222> LOCATION: (2)..(2)
<223> OTHER INFORMATION: D-Beta-Nal
<220> FEATURE:
<221> NAME/KEY: MOD_RES
<222> LOCATION: (3)..(3)
<223> OTHER INFORMATION: D-Ala
<220> FEATURE:
<221> NAME/KEY: MOD_RES
<222> LOCATION: (4)..(4)
<223> OTHER INFORMATION: D-Trp
<220> FEATURE:
<223> OTHER INFORMATION: C-terminus amidated

<400> SEQUENCE: 37

Ala Xaa Ala Trp Phe Lys
1               5

<210> SEQ ID NO 38
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Beta-Ala
<220> FEATURE:
<221> NAME/KEY: MOD_RES
<222> LOCATION: (3)..(3)
<223> OTHER INFORMATION: D-Ala
<220> FEATURE:
<221> NAME/KEY: MOD_RES
```

```
<222> LOCATION: (4)..(4)
<223> OTHER INFORMATION: D-Trp
<220> FEATURE:
<223> OTHER INFORMATION: C-terminus amidated

<400> SEQUENCE: 38

Ala Trp Ala Trp Phe
1               5

<210> SEQ ID NO 39
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: D-Ala
<220> FEATURE:
<221> NAME/KEY: MOD_RES
<222> LOCATION: (4)..(4)
<223> OTHER INFORMATION: D-Trp
<220> FEATURE:
<223> OTHER INFORMATION: C-terminus amidated

<400> SEQUENCE: 39

His Trp Ala Trp Phe Lys
1               5

<210> SEQ ID NO 40
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Lys
<220> FEATURE:
<221> NAME/KEY: MOD_RES
<222> LOCATION: (2)..(2)
<223> OTHER INFORMATION: D-Beta-Nal
<220> FEATURE:
<221> NAME/KEY: MOD_RES
<222> LOCATION: (5)..(5)
<223> OTHER INFORMATION: D-Phe
<220> FEATURE:
<223> OTHER INFORMATION: C-terminus amidated

<400> SEQUENCE: 40

Lys Xaa Ala Trp Phe Lys
1               5

<210> SEQ ID NO 41
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Ala
<220> FEATURE:
<221> NAME/KEY: MOD_RES
<222> LOCATION: (2)..(2)
<223> OTHER INFORMATION: D-Beta-Nal
<220> FEATURE:
```

```
<221> NAME/KEY: MOD_RES
<222> LOCATION: (3)..(3)
<223> OTHER INFORMATION: D-Lys
<220> FEATURE:
<221> NAME/KEY: MOD_RES
<222> LOCATION: (4)..(4)
<223> OTHER INFORMATION: D-Trp
<220> FEATURE:
<223> OTHER INFORMATION: C-terminus amidated

<400> SEQUENCE: 41

Ala Xaa Lys Trp Phe Lys
1               5

<210> SEQ ID NO 42
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: D-Ala
<220> FEATURE:
<221> NAME/KEY: MOD_RES
<222> LOCATION: (4)..(4)
<223> OTHER INFORMATION: Aib
<220> FEATURE:
<223> OTHER INFORMATION: C-terminus amidated

<400> SEQUENCE: 42

Tyr Ala Phe Xaa
1

<210> SEQ ID NO 43
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: D-Ala
<220> FEATURE:
<221> NAME/KEY: MOD_RES
<222> LOCATION: (3)..(3)
<223> OTHER INFORMATION: Sar
<220> FEATURE:
<221> NAME/KEY: MOD_RES
<222> LOCATION: (4)..(4)
<223> OTHER INFORMATION: NMePhe
<220> FEATURE:
<223> OTHER INFORMATION: C-terminus amidated

<400> SEQUENCE: 43

Tyr Ala Xaa Phe
1

<210> SEQ ID NO 44
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Alpha-Gamma-Abu
```

```
<220> FEATURE:
<221> NAME/KEY: MOD_RES
<222> LOCATION: (2)..(3)
<223> OTHER INFORMATION: D-Trp
<220> FEATURE:
<223> OTHER INFORMATION: C-terminus amidated

<400> SEQUENCE: 44

Xaa Trp Trp Ser
1

<210> SEQ ID NO 45
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Alpha-Gamma-Abu
<220> FEATURE:
<221> NAME/KEY: MOD_RES
<222> LOCATION: (2)..(3)
<223> OTHER INFORMATION: D-Trp
<220> FEATURE:
<223> OTHER INFORMATION: C-terminus amidated

<400> SEQUENCE: 45

Xaa Trp Trp Lys
1

<210> SEQ ID NO 46
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Alpha-Gamma-Abu
<220> FEATURE:
<221> NAME/KEY: MOD_RES
<222> LOCATION: (2)..(3)
<223> OTHER INFORMATION: D-Trp
<220> FEATURE:
<221> NAME/KEY: MOD_RES
<222> LOCATION: (4)..(4)
<223> OTHER INFORMATION: Orn
<220> FEATURE:
<223> OTHER INFORMATION: C-terminus amidated

<400> SEQUENCE: 46

Xaa Trp Trp Xaa
1

<210> SEQ ID NO 47
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Alpha-Abu
<220> FEATURE:
<221> NAME/KEY: MOD_RES
<222> LOCATION: (2)..(3)
```

```
<223> OTHER INFORMATION: D-Trp
<220> FEATURE:
<221> NAME/KEY: MOD_RES
<222> LOCATION: (4)..(4)
<223> OTHER INFORMATION: Orn
<220> FEATURE:
<223> OTHER INFORMATION: C-terminus amidated

<400> SEQUENCE: 47

Xaa Trp Trp Xaa
1

<210> SEQ ID NO 48
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Thr
<220> FEATURE:
<221> NAME/KEY: MOD_RES
<222> LOCATION: (2)..(2)
<223> OTHER INFORMATION: D-Alpha-Nal
<220> FEATURE:
<221> NAME/KEY: MOD_RES
<222> LOCATION: (3)..(3)
<223> OTHER INFORMATION: D-Trp
<220> FEATURE:
<221> NAME/KEY: MOD_RES
<222> LOCATION: (4)..(4)
<223> OTHER INFORMATION: D-Pro
<220> FEATURE:
<223> OTHER INFORMATION: C-terminus amidated

<400> SEQUENCE: 48

Thr Xaa Trp Pro Arg
1               5

<210> SEQ ID NO 49
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Ala
<220> FEATURE:
<221> NAME/KEY: MOD_RES
<222> LOCATION: (3)..(3)
<223> OTHER INFORMATION: D-Ala
<220> FEATURE:
<221> NAME/KEY: MOD_RES
<222> LOCATION: (4)..(4)
<223> OTHER INFORMATION: D-Trp
<220> FEATURE:
<223> OTHER INFORMATION: C-terminus amidated

<400> SEQUENCE: 49

Ala Ala Ala Trp Phe Lys
1               5

<210> SEQ ID NO 50
<211> LENGTH: 7
<212> TYPE: PRT
<213> ORGANISM: Artificial Sequence
<220> FEATURE:
```

```
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Ala Psi[CH2NH]
<220> FEATURE:
<221> NAME/KEY: MOD_RES
<222> LOCATION: (3)..(3)
<223> OTHER INFORMATION: D-Trp
<220> FEATURE:
<221> NAME/KEY: MOD_RES
<222> LOCATION: (6)..(6)
<223> OTHER INFORMATION: D-Phe
<220> FEATURE:
<223> OTHER INFORMATION: C-terminus amidated

<400> SEQUENCE: 50

Ala His Trp Ala Trp Phe Lys
1               5

<210> SEQ ID NO 51
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: D-His
<220> FEATURE:
<221> NAME/KEY: MOD_RES
<222> LOCATION: (3)..(3)
<223> OTHER INFORMATION: D-Trp
<220> FEATURE:
<223> OTHER INFORMATION: C-terminus amidated

<400> SEQUENCE: 51

Lys His Trp Phe
1

<210> SEQ ID NO 52
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Gamma-Abu
<220> FEATURE:
<221> NAME/KEY: MOD_RES
<222> LOCATION: (2)..(3)
<223> OTHER INFORMATION: D-Trp
<220> FEATURE:
<221> NAME/KEY: MOD_RES
<222> LOCATION: (4)..(4)
<223> OTHER INFORMATION: Orn
<220> FEATURE:
<223> OTHER INFORMATION: C-terminus amidated

<400> SEQUENCE: 52

Xaa Trp Trp Xaa
1

<210> SEQ ID NO 53
<211> LENGTH: 4
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Isonipecotic carboxylic acid
<220> FEATURE:
<223> OTHER INFORMATION: C-terminus amidated

<400> SEQUENCE: 53

Xaa Trp Trp Phe
1

<210> SEQ ID NO 54
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-terminus acetylated
<220> FEATURE:
<221> NAME/KEY: MOD_RES
<222> LOCATION: (1)..(1)
<223> OTHER INFORMATION: D-Trp
<220> FEATURE:
<221> NAME/KEY: MOD_RES
<222> LOCATION: (3)..(3)
<223> OTHER INFORMATION: D-Trp
<220> FEATURE:
<223> OTHER INFORMATION: C-terminus amidated

<400> SEQUENCE: 54

Trp Phe Trp Leu
1

<210> SEQ ID NO 55
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-terminus acetylated
<220> FEATURE:
<221> NAME/KEY: MOD_RES
<222> LOCATION: (1)..(1)
<223> OTHER INFORMATION: D-Trp
<220> FEATURE:
<221> NAME/KEY: MOD_RES
<222> LOCATION: (3)..(3)
<223> OTHER INFORMATION: D-Trp
<220> FEATURE:
<223> OTHER INFORMATION: C-terminus amidated

<400> SEQUENCE: 55

Trp Phe Trp Lys
1

<210> SEQ ID NO 56
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-terminus acetylated
<220> FEATURE:
<221> NAME/KEY: MOD_RES
```

```
<222> LOCATION: (1)..(2)
<223> OTHER INFORMATION: D-Trp
<220> FEATURE:
<223> OTHER INFORMATION: C-terminus amidated

<400> SEQUENCE: 56

Trp Trp Lys
1

<210> SEQ ID NO 57
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Lys
<220> FEATURE:
<221> NAME/KEY: MOD_RES
<222> LOCATION: (3)..(4)
<223> OTHER INFORMATION: D-Trp
<220> FEATURE:
<223> OTHER INFORMATION: C-terminus amidated

<400> SEQUENCE: 57

Lys Tyr Trp Trp Phe Lys
1               5

<210> SEQ ID NO 58
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-terminus acetylated
<220> FEATURE:
<221> NAME/KEY: MOD_RES
<222> LOCATION: (1)..(1)
<223> OTHER INFORMATION: D-Beta-Nal
<220> FEATURE:
<223> OTHER INFORMATION: C-terminus amidated

<400> SEQUENCE: 58

Xaa Leu Pro
1

<210> SEQ ID NO 59
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Beta-Ala
<220> FEATURE:
<221> NAME/KEY: MOD_RES
<222> LOCATION: (3)..(4)
<223> OTHER INFORMATION: D-Trp
<220> FEATURE:
<221> NAME/KEY: MOD_RES
<222> LOCATION: (5)..(5)
<223> OTHER INFORMATION: Orn
<220> FEATURE:
<223> OTHER INFORMATION: C-terminus amidated
```

```
<400> SEQUENCE: 59

Ala Trp Trp Trp Xaa
1               5

<210> SEQ ID NO 60
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Val
<220> FEATURE:
<221> NAME/KEY: MOD_RES
<222> LOCATION: (2)..(2)
<223> OTHER INFORMATION: D-Alpha-Nal
<220> FEATURE:
<221> NAME/KEY: MOD_RES
<222> LOCATION: (3)..(3)
<223> OTHER INFORMATION: D-Trp
<220> FEATURE:
<223> OTHER INFORMATION: C-terminus amidated

<400> SEQUENCE: 60

Val Xaa Trp Phe Arg
1               5

<210> SEQ ID NO 61
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Leu
<220> FEATURE:
<221> NAME/KEY: MOD_RES
<222> LOCATION: (2)..(2)
<223> OTHER INFORMATION: D-Alpha-Nal
<220> FEATURE:
<221> NAME/KEY: MOD_RES
<222> LOCATION: (3)..(3)
<223> OTHER INFORMATION: D-Trp
<220> FEATURE:
<223> OTHER INFORMATION: C-terminus amidated

<400> SEQUENCE: 61

Leu Xaa Trp Phe Arg
1               5

<210> SEQ ID NO 62
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Cyclohexyl-Ala
<220> FEATURE:
<221> NAME/KEY: MOD_RES
<222> LOCATION: (2)..(2)
<223> OTHER INFORMATION: D-Alpha-Nal
<220> FEATURE:
<221> NAME/KEY: MOD_RES
```

```
<222> LOCATION: (3)..(3)
<223> OTHER INFORMATION: D-Trp
<220> FEATURE:
<223> OTHER INFORMATION: C-terminus amidated

<400> SEQUENCE: 62

Ala Xaa Trp Phe Arg
1               5

<210> SEQ ID NO 63
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Trp
<220> FEATURE:
<221> NAME/KEY: MOD_RES
<222> LOCATION: (2)..(2)
<223> OTHER INFORMATION: D-Alpha-Nal
<220> FEATURE:
<221> NAME/KEY: MOD_RES
<222> LOCATION: (3)..(3)
<223> OTHER INFORMATION: D-Trp
<220> FEATURE:
<223> OTHER INFORMATION: C-terminus amidated

<400> SEQUENCE: 63

Trp Xaa Trp Phe Arg
1               5

<210> SEQ ID NO 64
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Ala
<220> FEATURE:
<221> NAME/KEY: MOD_RES
<222> LOCATION: (2)..(2)
<223> OTHER INFORMATION: D-Beta-Nal
<220> FEATURE:
<221> NAME/KEY: MOD_RES
<222> LOCATION: (3)..(3)
<223> OTHER INFORMATION: D-Pro
<220> FEATURE:
<223> OTHER INFORMATION: C-terminus amidated

<400> SEQUENCE: 64

Ala Xaa Pro Phe Arg
1               5

<210> SEQ ID NO 65
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-terminus acetylated
<220> FEATURE:
<221> NAME/KEY: MOD_RES
<222> LOCATION: (1)..(1)
```

<223> OTHER INFORMATION: D-Alpha-Nal
<220> FEATURE:
<221> NAME/KEY: MOD_RES
<222> LOCATION: (2)..(2)
<223> OTHER INFORMATION: D-Trp
<220> FEATURE:
<223> OTHER INFORMATION: C-terminus amidated

<400> SEQUENCE: 65

Xaa Trp Phe Arg
1

<210> SEQ ID NO 66
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Alpha-Nal
<220> FEATURE:
<221> NAME/KEY: MOD_RES
<222> LOCATION: (2)..(2)
<223> OTHER INFORMATION: D-Trp
<220> FEATURE:
<223> OTHER INFORMATION: C-terminus amidated

<400> SEQUENCE: 66

Xaa Trp Phe Arg
1

<210> SEQ ID NO 67
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(3)
<223> OTHER INFORMATION: D-Trp
<220> FEATURE:
<223> OTHER INFORMATION: C-terminus amidated

<400> SEQUENCE: 67

His Trp Trp Lys
1

<210> SEQ ID NO 68
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-terminus acetylated
<220> FEATURE:
<221> NAME/KEY: MOD_RES
<222> LOCATION: (1)..(1)
<223> OTHER INFORMATION: D-Beta-Nal
<220> FEATURE:
<221> NAME/KEY: MOD_RES
<222> LOCATION: (2)..(2)
<223> OTHER INFORMATION: D-Trp
<220> FEATURE:
<223> OTHER INFORMATION: C-terminus amidated

<400> SEQUENCE: 68

Xaa Trp
1

<210> SEQ ID NO 69
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Alpha-Aib
<220> FEATURE:
<221> NAME/KEY: MOD_RES
<222> LOCATION: (2)..(2)
<223> OTHER INFORMATION: D-Trp
<220> FEATURE:
<221> NAME/KEY: MOD_RES
<222> LOCATION: (3)..(3)
<223> OTHER INFORMATION: D-cyclohexyl-Ala
<220> FEATURE:
<223> OTHER INFORMATION: C-terminus amidated

<400> SEQUENCE: 69

Xaa Trp Ala
1

<210> SEQ ID NO 70
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Alpha-Aib
<220> FEATURE:
<221> NAME/KEY: MOD_RES
<222> LOCATION: (2)..(2)
<223> OTHER INFORMATION: D-Trp
<220> FEATURE:
<221> NAME/KEY: MOD_RES
<222> LOCATION: (3)..(3)
<223> OTHER INFORMATION: D-Ala
<220> FEATURE:
<221> NAME/KEY: MOD_RES
<222> LOCATION: (4)..(4)
<223> OTHER INFORMATION: Cyclohexyl-Ala
<220> FEATURE:
<223> OTHER INFORMATION: C-terminus amidated

<400> SEQUENCE: 70

Xaa Trp Ala Ala
1

<210> SEQ ID NO 71
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Ala
<220> FEATURE:
<221> NAME/KEY: MOD_RES
<222> LOCATION: (2)..(2)

```
<223> OTHER INFORMATION: D-cyclohexyl-Ala
<220> FEATURE:
<221> NAME/KEY: MOD_RES
<222> LOCATION: (6)..(6)
<223> OTHER INFORMATION: D-Phe
<220> FEATURE:
<221> NAME/KEY: MOD_RES
<222> LOCATION: (7)..(7)
<223> OTHER INFORMATION: Nle
<220> FEATURE:
<223> OTHER INFORMATION: C-terminus amidated

<400> SEQUENCE: 71

Ala Ala Ala Ala Phe Phe Xaa
1               5

<210> SEQ ID NO 72
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Phe
<220> FEATURE:
<221> NAME/KEY: MOD_RES
<222> LOCATION: (4)..(4)
<223> OTHER INFORMATION: D-Pal
<220> FEATURE:
<223> OTHER INFORMATION: C-terminus amidated

<400> SEQUENCE: 72

Phe Ala Phe Xaa
1

<210> SEQ ID NO 73
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Phe
<220> FEATURE:
<221> NAME/KEY: MOD_RES
<222> LOCATION: (4)..(4)
<223> OTHER INFORMATION: D-Phe
<220> FEATURE:
<223> OTHER INFORMATION: C-terminus amidated

<400> SEQUENCE: 73

Phe Ala Phe Phe Lys
1               5

<210> SEQ ID NO 74
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Lys
<220> FEATURE:
<221> NAME/KEY: MOD_RES
```

<222> LOCATION: (3)..(4)
<223> OTHER INFORMATION: D-Trp
<220> FEATURE:
<223> OTHER INFORMATION: C-terminus amidated

<400> SEQUENCE: 74

Lys Tyr Trp Trp Phe
1               5

<210> SEQ ID NO 75
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-terminus acetylated
<220> FEATURE:
<221> NAME/KEY: MOD_RES
<222> LOCATION: (1)..(1)
<223> OTHER INFORMATION: D-Lys
<220> FEATURE:
<221> NAME/KEY: MOD_RES
<222> LOCATION: (3)..(4)
<223> OTHER INFORMATION: D-Trp
<220> FEATURE:
<223> OTHER INFORMATION: C-terminus amidated

<400> SEQUENCE: 75

Lys Tyr Trp Trp Phe
1               5

<210> SEQ ID NO 76
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: D-Trp
<220> FEATURE:
<221> NAME/KEY: misc_feature
<222> LOCATION: (7)..(8)
<223> OTHER INFORMATION: Cyclic

<400> SEQUENCE: 76

Arg Trp Leu Tyr Trp Pro Arg Pro
1               5

<210> SEQ ID NO 77
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-terminus acetylated
<220> FEATURE:
<221> NAME/KEY: MOD_RES
<222> LOCATION: (1)..(1)
<223> OTHER INFORMATION: D-Beta-Nal
<220> FEATURE:
<221> NAME/KEY: MOD_RES
<222> LOCATION: (2)..(2)
<223> OTHER INFORMATION: PicLys
<220> FEATURE:
<221> NAME/KEY: MOD_RES
<222> LOCATION: (3)..(3)

```
<223> OTHER INFORMATION: Lys(iPr)
<220> FEATURE:
<221> NAME/KEY: MOD_RES
<222> LOCATION: (4)..(4)
<223> OTHER INFORMATION: D-Phe
<220> FEATURE:
<223> OTHER INFORMATION: C-terminus amidated

<400> SEQUENCE: 77

Xaa Lys Lys Phe
1

<210> SEQ ID NO 78
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Pal
<220> FEATURE:
<221> NAME/KEY: MOD_RES
<222> LOCATION: (3)..(3)
<223> OTHER INFORMATION: D-Trp
<220> FEATURE:
<223> OTHER INFORMATION: C-terminus amidated

<400> SEQUENCE: 78

Xaa Phe Trp Phe Met
1               5

<210> SEQ ID NO 79
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Phe
<220> FEATURE:
<221> NAME/KEY: MOD_RES
<222> LOCATION: (3)..(3)
<223> OTHER INFORMATION: D-Phe
<220> FEATURE:
<223> OTHER INFORMATION: C-terminus amidated

<400> SEQUENCE: 79

Phe Trp Phe Phe Met
1               5

<210> SEQ ID NO 80
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Pal
<220> FEATURE:
<221> NAME/KEY: MOD_RES
<222> LOCATION: (3)..(3)
<223> OTHER INFORMATION: D-Phe
<220> FEATURE:
<223> OTHER INFORMATION: C-terminus amidated
```

```
<400> SEQUENCE: 80

Xaa Trp Phe Phe Met
1               5

<210> SEQ ID NO 81
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Beta-Ala
<220> FEATURE:
<221> NAME/KEY: MOD_RES
<222> LOCATION: (2)..(2)
<223> OTHER INFORMATION: Pal
<220> FEATURE:
<221> NAME/KEY: MOD_RES
<222> LOCATION: (3)..(4)
<223> OTHER INFORMATION: D-Trp
<220> FEATURE:
<221> NAME/KEY: MOD_RES
<222> LOCATION: (5)..(5)
<223> OTHER INFORMATION: Orn
<220> FEATURE:
<223> OTHER INFORMATION: C-terminus amidated

<400> SEQUENCE: 81

Ala Xaa Trp Trp Xaa
1               5

<210> SEQ ID NO 82
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Alpha-Gamma-Abu
<220> FEATURE:
<221> NAME/KEY: MOD_RES
<222> LOCATION: (3)..(4)
<223> OTHER INFORMATION: D-Trp
<220> FEATURE:
<221> NAME/KEY: MOD_RES
<222> LOCATION: (5)..(5)
<223> OTHER INFORMATION: Orn
<220> FEATURE:
<223> OTHER INFORMATION: C-terminus amidated

<400> SEQUENCE: 82

Xaa Trp Trp Trp Xaa
1               5

<210> SEQ ID NO 83
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Beta-Ala
<220> FEATURE:
```

```
<221> NAME/KEY: MOD_RES
<222> LOCATION: (3)..(4)
<223> OTHER INFORMATION: D-Trp
<220> FEATURE:
<223> OTHER INFORMATION: C-terminus amidated

<400> SEQUENCE: 83

Ala Trp Trp Trp Lys
1               5

<210> SEQ ID NO 84
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Gamma-Abu
<220> FEATURE:
<221> NAME/KEY: MOD_RES
<222> LOCATION: (3)..(4)
<223> OTHER INFORMATION: D-Trp
<220> FEATURE:
<221> NAME/KEY: MOD_RES
<222> LOCATION: (5)..(5)
<223> OTHER INFORMATION: Orn
<220> FEATURE:
<223> OTHER INFORMATION: C-terminus amidated

<400> SEQUENCE: 84

Xaa Trp Trp Trp Xaa
1               5

<210> SEQ ID NO 85
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Ava
<220> FEATURE:
<221> NAME/KEY: MOD_RES
<222> LOCATION: (3)..(4)
<223> OTHER INFORMATION: D-Trp
<220> FEATURE:
<221> NAME/KEY: MOD_RES
<222> LOCATION: (5)..(5)
<223> OTHER INFORMATION: Orn
<220> FEATURE:
<223> OTHER INFORMATION: C-terminus amidated

<400> SEQUENCE: 85

Xaa Trp Trp Trp Xaa
1               5

<210> SEQ ID NO 86
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Lys
```

```
<220> FEATURE:
<221> NAME/KEY: MOD_RES
<222> LOCATION: (3)..(3)
<223> OTHER INFORMATION: D-Trp
<220> FEATURE:
<221> NAME/KEY: MOD_RES
<222> LOCATION: (6)..(6)
<223> OTHER INFORMATION: D-Phe
<220> FEATURE:
<223> OTHER INFORMATION: C-terminus amidated

<400> SEQUENCE: 86

Lys Tyr Trp Ala Trp Phe
1               5

<210> SEQ ID NO 87
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: D-Trp
<220> FEATURE:
<221> NAME/KEY: MOD_RES
<222> LOCATION: (3)..(3)
<223> OTHER INFORMATION: D-Arg
<220> FEATURE:
<221> NAME/KEY: MOD_RES
<222> LOCATION: (5)..(5)
<223> OTHER INFORMATION: D-Phe
<220> FEATURE:
<223> OTHER INFORMATION: C-terminus amidated

<400> SEQUENCE: 87

His Trp Arg Trp Phe
1               5

<210> SEQ ID NO 88
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pyroglutamic acid
<220> FEATURE:
<221> NAME/KEY: MOD_RES
<222> LOCATION: (4)..(4)
<223> OTHER INFORMATION: D-Ser
<220> FEATURE:
<221> NAME/KEY: MOD_RES
<222> LOCATION: (5)..(5)
<223> OTHER INFORMATION: D-Arg
<220> FEATURE:
<223> OTHER INFORMATION: C-terminus amidated

<400> SEQUENCE: 88

Glu His Trp Ser Arg
1               5

<210> SEQ ID NO 89
<211> LENGTH: 5
<212> TYPE: PRT
<213> ORGANISM: Artificial Sequence
<220> FEATURE:
<223> OTHER INFORMATION: Description of Artificial Sequence: Synthetic
```

```
            peptide
<220> FEATURE:
<221> NAME/KEY: MOD_RES
<222> LOCATION: (1)..(2)
<223> OTHER INFORMATION: D-Phe
<220> FEATURE:
<221> NAME/KEY: MOD_RES
<222> LOCATION: (3)..(3)
<223> OTHER INFORMATION: D-Trp
<220> FEATURE:
<221> NAME/KEY: MOD_RES
<222> LOCATION: (5)..(5)
<223> OTHER INFORMATION: D-Lys
<220> FEATURE:
<223> OTHER INFORMATION: C-terminus amidated

<400> SEQUENCE: 89

Phe Phe Trp Met Lys
1               5

<210> SEQ ID NO 90
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-His
<220> FEATURE:
<221> NAME/KEY: MOD_RES
<222> LOCATION: (2)..(2)
<223> OTHER INFORMATION: D-Trp
<220> FEATURE:
<221> NAME/KEY: MOD_RES
<222> LOCATION: (3)..(3)
<223> OTHER INFORMATION: D-Pro
<220> FEATURE:
<221> NAME/KEY: MOD_RES
<222> LOCATION: (4)..(4)
<223> OTHER INFORMATION: D-Ile
<220> FEATURE:
<223> OTHER INFORMATION: C-terminus amidated

<400> SEQUENCE: 90

His Trp Pro Ile
1

<210> SEQ ID NO 91
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-His
<220> FEATURE:
<221> NAME/KEY: MOD_RES
<222> LOCATION: (2)..(2)
<223> OTHER INFORMATION: D-Trp
<220> FEATURE:
<221> NAME/KEY: MOD_RES
<222> LOCATION: (3)..(3)
<223> OTHER INFORMATION: D-Pro
<220> FEATURE:
<221> NAME/KEY: MOD_RES
<222> LOCATION: (4)..(4)
<223> OTHER INFORMATION: D-Arg
<220> FEATURE:
<223> OTHER INFORMATION: C-terminus amidated
```

```
<400> SEQUENCE: 91

His Trp Pro Arg
1

<210> SEQ ID NO 92
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Beta-Nal
<220> FEATURE:
<221> NAME/KEY: MOD_RES
<222> LOCATION: (2)..(2)
<223> OTHER INFORMATION: D-Trp
<220> FEATURE:
<221> NAME/KEY: MOD_RES
<222> LOCATION: (3)..(3)
<223> OTHER INFORMATION: D-Pro
<220> FEATURE:
<221> NAME/KEY: MOD_RES
<222> LOCATION: (4)..(4)
<223> OTHER INFORMATION: D-Arg
<220> FEATURE:
<223> OTHER INFORMATION: C-terminus amidated

<400> SEQUENCE: 92

Xaa Trp Pro Arg
1

<210> SEQ ID NO 93
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(3)
<223> OTHER INFORMATION: Any amino acid or absent
<220> FEATURE:
<221> NAME/KEY: MOD_RES
<222> LOCATION: (6)..(6)
<223> OTHER INFORMATION: Ser or diaminopropionic acid
<220> FEATURE:
<221> NAME/KEY: MOD_RES
<222> LOCATION: (9)..(12)
<223> OTHER INFORMATION: Any amino acid or absent
<220> FEATURE:
<223> OTHER INFORMATION: see specification as filed for detailed
      description of substitutions and preferred embodiments

<400> SEQUENCE: 93

Xaa Xaa Xaa Gly Ser Xaa Phe Leu Xaa Xaa Xaa Xaa
1               5                   10

<210> SEQ ID NO 94
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Ser(Oct)
```

```
<220> FEATURE:
<223> OTHER INFORMATION: C-terminus amidated

<400> SEQUENCE: 94

Gly Ser Ser Phe Leu
1               5

<210> SEQ ID NO 95
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Dap(Oct)
<220> FEATURE:
<223> OTHER INFORMATION: C-terminus amidated

<400> SEQUENCE: 95

Gly Ser Xaa Phe Leu
1               5

<210> SEQ ID NO 96
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: D-Trp
<220> FEATURE:
<221> NAME/KEY: MOD_RES
<222> LOCATION: (5)..(5)
<223> OTHER INFORMATION: D-Phe
<220> FEATURE:
<223> OTHER INFORMATION: C-terminus amidated

<400> SEQUENCE: 96

His Trp Ala Trp Phe Lys
1               5

<210> SEQ ID NO 97
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Ala
<220> FEATURE:
<221> NAME/KEY: MOD_RES
<222> LOCATION: (2)..(2)
<223> OTHER INFORMATION: D-Beta-Nal
<220> FEATURE:
<221> NAME/KEY: MOD_RES
<222> LOCATION: (5)..(5)
<223> OTHER INFORMATION: D-Phe
<220> FEATURE:
<223> OTHER INFORMATION: C-terminus amidated

<400> SEQUENCE: 97

Ala Xaa Ala Trp Phe Lys
1               5
```

```
<210> SEQ ID NO 98
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: D-Trp
<220> FEATURE:
<221> NAME/KEY: MOD_RES
<222> LOCATION: (5)..(5)
<223> OTHER INFORMATION: D-Phe
<220> FEATURE:
<223> OTHER INFORMATION: C-terminus amidated

<400> SEQUENCE: 98

Tyr Trp Ala Trp Phe
1               5
```

METHODS OF INHIBITING THE GHRELIN/GROWTH HORMONE SECRETATOGUE RECEPTOR PATHWAY AND USES THEREOF

CROSS REFERENCE TO RELATED APPLICATIONS

This application is a 35 U.S.C. §371 National Phase Entry Application of International Application No. PCT/US2010/034570, filed May 12, 2010, which designates the United States, and which claims the benefit under 35 U.S.C. §119(e) of the U.S. Provisional Application No. 61/177,400, filed May 12, 2009, the content of which is herein incorporated by reference in its entirety.

FIELD OF INVENTION

This invention relates to novel methods for treatment, management and prevention of a range of medical conditions that are associated with the activation of the ghrelin/growth hormone receptor pathway. The medical conditions include but are not limited to, obesity and obesity-associated disorders, diabetes, metabolic and/or endocrine disorders, gastrointestinal disorders, cardiovascular disorders, central nervous system disorders, genetic disorders, and hyperproliferative disorders. Methods of modulating of the ghrelin/growth hormone receptor pathway include simultaneously inhibiting the synthesis of active ghrelin and inhibiting ghrelin receptor pathway activation. Inhibition of the synthesis of active ghrelin is achieved by a ghrelin O-acyltransferase (GOAT) inhibitor. Inhibition of ghrelin receptor activation is achieved by ghrelin receptor antagonists or inverse agonist.

BACKGROUND OF THE INVENTION

In America, there is a dramatic raise in the number of people who are overweight. About 66% of U.S. adults age 20 or older are overweight. About 31% of American adults are obese today compared to 24% in 1994. Childhood obesity is also fast increasing. The prevalence of overweight has steadily increased over the years among both genders, all ages, racial and ethnic groups, educational levels, and smoking levels. Accompanying overweight and obesity are a host of life threatening diseases-diabetes, heart disease, stroke, high blood pressure and certain cancers—which greatly decrease the quality of life and shorten the life expectancy of an overweight/obese person. Every year, tens of thousands of severely obese individuals undergo some sort of bariatric surgery to control their eating and weight problem. Weight loss and exercise programs are multi-million dollar industry in America. Millions are also spent on treating the overweight and obesity-related diseases. Therefore, additional new approaches to addressing the overweight and obesity issue are useful and urgently needed in our modern society.

The growth hormone (GH) secretatogue receptor (GHS-R) (also known as the ghrelin receptor) pathway is a powerful stimulator of pulsatile GH secretion and the pathway exhibits intricate interactions with several primary hypothalamic GH regulators. The elevation of growth hormone (GH) levels in animals, e.g., mammals including humans, upon administration of GH-releasing compounds can lead to enhanced body weight and metabolic diseases/disorders such as obesity and diabetes mellitus. Examples of GH-releasing compounds include ghrelin, an endogenous ligand for GHS-R, growth hormone releasing peptides (GHRPs) and growth hormone secretatogues (GHSs), all of which are potent orexigenic peptides. Orexigenic compounds stimulate appetite. In the absence of the ghrelin receptor, transgenic female and male mice fed a high fat diet eat less food, less of the consumed calories are stored, fat is more of the energy substrate, and body weight and body fat are less in these mice than control mice. When the ghrelin receptor was absent and mice were fed a normal diet, body weight and body fat were decreased in female but not in male mice. In the absence of the ghrelin peptide, transgenic male mice (female mice not studied) had less rapid body weight gain on a high fat diet. This was associated with increased energy expenditure and increased locomotive activity as well as decreased adiposity. These studies indicate the ghrelin pathway is involved in body weight control especially when consuming a high caloric type of obese inducing diet. In the absence of the ghrelin receptor (GHS-R 1a), ghrelin no longer increased food intake. Thus, the singularity of this receptor for mediating ghrelin induced food intake is indicated. Also, hyperphagia is an established risk factor in diabetes mellitus in humans and evidence indicates that sub-threshold doses of ghrelin increases food intake in streptozotocin treated rats. Experimental studies in rats revealed interrelationships of ghrelin, somatostatin and GHRH on function of the GH axis.

Plasma levels of ghrelin rise precipitously in the blood before meals, when the stomach is empty, and fall after or during food consumption. Since intracadiac venous (i.v.) or intracerebroventricular (i.c.v) administration of ghrelin increases food intake, it appears that the physiological role of ghrelin is a link or messenger between the stomach and the hypothalamus and the pituitary. One hypothesis is that when an organism is getting ready for a meal, the CNS sends signals to the GI tract telling that a meal is about to be consumed in order to obtain information back about the status of the digestive process, state of distension etc. from the various chemical and mechanical sensors in the gut. Here, ghrelin could be an important hormonal messenger, which is sent back to the central nervous system (CNS) as a signal telling that there is no food in the stomach and that the gastrointestinal (GI) tract is ready for a new meal. In such a paradigm it is clear that a blocker of the ghrelin receptor would be a very efficient anti-obesity agent, as it would block the meal initiating, appetite signal from the GI tract.

The ghrelin receptor, GHS-R 1a, belongs to a relatively small family of 7 transmembrane G-protein coupled receptors. A number of findings demonstrate how the ghrelin receptor uniquely play a role in mediating the action on GH release and food intake. This includes ghrelin receptor genetics, mutations, structure, intracellular signaling, high constitutive activity, enhancement of the number of hypothalamic ghrelin receptors during starvation, etc. A spectrum of growth and metabolic changes occur in mice as a result of knockout of the ghrelin molecule as well as the ghrelin receptor. Adiposity in mice followed over expression of the ghrelin receptor in hypothalamic growth hormone releasing hormone (GHRH) arcuate neurons. Over time, select biological effects of ghrelin/GHSs, especially non-endocrine effects, have been revealed which presumably occur via subtypes receptors of ghrelin or perhaps ghrelin receptors with select mutations. Evidence indicates binding and activation of the multifunctional CD36 receptor by GHSs. Another noteworthy finding of the ghrelin receptor was that under pathophysiological conditions the density of this receptor was reported to be five times greater in atherosclerotic coronary arteries.

Peptide antagonists that inhibited the binding activity of GHSs in hypothalamic tissue in vitro have been reported. This included the substance P ("Sub P") analog, [DArg$^1$ DPhe$^5$ DTrp$^{7,9}$ Leu$^{11}$]-Substance P, that subsequently was demonstrated by Hoist et al (J. Biol. Chem. 282, 15799 (2007)) to have both inverse agonist and ghrelin-R antagonist activity.

The ghrelin receptor, GHS-R 1a is a constitutively active receptor, i.e. there is spontaneous, ligand-independent signaling from this receptor. This constitutive activity can be inhibited by [DArg$^1$,DPhe$^5$, DTrp$^{7,9}$ Leu$^{11}$]-substance P analog which has been previously characterized both in vitro and in vivo as a weak competitive receptor antagonist to acute and chronic actions of GHRP-2 and ghrelin. This Sub P analog has 2 types of ghrelin receptor inhibiting activities. At a low dose (5 nM, IC$_{50}$), this Sub P analog is a potent inverse receptor agonist since it decreases elevated intracellular IP3 levels in the absence of ghrelin but also it is a weak ghrelin GHRP-6 competitive receptor antagonist since high dosages (630 nM, IC$_{50}$) inhibited receptor binding of both peptides. Continuous i.c.v 7 day infusion of a very low dose of the Sub P ghrelin receptor inverse agonist inhibited body weight gain of male rats. This was a dose that would be too low to function as a competitive ghrelin receptor antagonist and thus it was considered to be due to the inverse agonist activity of the Sub P analog. In vitro evidence supports GHS-R antagonists with only inverse agonist or only ghrelin/GHS-R activity or a combination of the two.

It is proposed that the high constitutive activity of the ghrelin receptor plays a key functional role at CNS sites at which the receptor is expressed within the blood brain barrier and thus does not have immediate access to circulating ghrelin. This is in contrast to the ghrelin receptor located in the arcuate nucleus and dorsal vagal complex role. Thus it is possible that select GHSs, because of their different chemistry, may have ready access to brain sites inaccessible to ghrelin. If this occurs, GHSs' actions at these sites may alter the CNS ghrelin constitutive activity via receptor number and/or activity.

Accordingly, methods that inhibit and/or disrupt the activity of the GHS-R signaling pathway are useful in regulating GH secretion, appetite, and body weight. Furthermore, since metabolic diseases and disorders such as obesity, diabetes mellitus, and inhibition of growth hormone secreted from tumors such as pituitary, prostate, osteoblast, pancreatic and hepatoma are directly and indirectly associated with activities of the GH axis, new strategies that inhibit/disrupt this pathway's activation, particularly at the level of the CNS, are useful in the treatment of these metabolic diseases and disorders and cancers.

SUMMARY OF THE INVENTION

The present invention provides novel strategies for inhibiting and/or disrupting the activities of ghrelin and/or the ghrelin/GHS-R 1a signaling pathway in vivo for the treatment of metabolic diseases and disorders such as obesity, overeating, diabetes mellitus, unregulated cell proliferation and for the inhibition of growth hormone secreted from tumors such as pituitary, prostate, medullary thyroid carcinomas, osteoblast, pancreatic and hepatoma. The strategy is to simultaneously inhibiting the synthesis of active ghrelin and inhibiting ghrelin receptor activation, and thus the ghrelin/GHS-R 1a signaling pathway. In some embodiments, the strategy comprises inhibiting the synthesis of active ghrelin only. Inhibition of the synthesis of active ghrelin is achieved by a ghrelin O-acyltransferase (GOAT) inhibitor. Inhibition of ghrelin receptor activation is achieved by a ghrelin receptor antagonist or inverse agonist. Examples of GOAT inhibitors and ghrelin receptor antagonists and inverse agonist are described herein.

Accordingly, provided herein is a method for inhibiting and/or disrupting the GHS-R signaling pathway in a subject in need thereof, the method comprising administering an effective amount of a ghrelin O-acyltransferase (GOAT) inhibitor and an effective amount of a ghrelin receptor antagonist and/or inverse agonist. In one embodiment, provided herein is a method for inhibiting and/or disrupting the GHS-R signaling pathway in a subject in need thereof, the method comprising administering an effective amount of a GOAT inhibitor. In another embodiment, provided herein is a method for inhibiting and/or disrupting the GHS-R signaling pathway in a subject in need thereof, the method comprising administering an effective amount of ghrelin receptor antagonist and/or inverse agonist. Such individuals can be one with overeating disorder, obesity, obesity related disease or disorder, diabetes mellitus, metabolic syndrome and cancer. It is also contemplated that a plurality of GOAT inhibitors and/or ghrelin receptor antagonists and/or inverse agonists are administered.

Accordingly, provided herein is a method for treatment, prevention or management of obesity in a subject in need thereof, the method comprising the step of administering an effective amount of a ghrelin O-acyltransferase (GOAT) inhibitor and an effective amount of a ghrelin receptor antagonist and/or inverse agonist.

In another embodiment, the invention provides a method for treatment, prevention or management of obesity related disease or disorder in a subject in need thereof, the method comprising the step of administering an effective amount of a ghrelin O-acyltransferase (GOAT) inhibitor and an effective amount of a ghrelin receptor antagonist and/or inverse agonist. Obesity related disease or disorder can include but are not limited to diabetes, hypertension, and metabolic syndrome.

In one embodiment, the method for treatment, prevention or management of obesity and obesity related disease or disorder in a subject in need thereof further comprises an anti-obesity treatment. In one embodiment, the anti-obesity treatment is a combination of dietary restriction therapy with a 5HT (serotonin) transporter inhibitor, a NE (norepinephrine) transporter inhibitor, a CB-1 (cannabinoid-1) antagonist/inverse agonist, a H3 (histamine H3) antagonist/inverse agonist, a MCH1R (melanin concentrating hormone 1R) antagonist, a MCH2R agonist/antagonist, a NPY1 antagonist, a leptin, a leptin derivative, a leptin analog, PYY(3-36), PYY (1-36), an opioid antagonist, an orexin antagonist, a BRS3 (bombesin receptor subtype 3) agonist, a CCK-A (cholecystokinin-A) agonist, a CNTF (Ciliary neurotrophic factor), a CNTF derivative, or a lipase drug inhibitor administered simultaneously, concurrently or sequentially. In another embodiment, the anti-obesity treatment is bariatric surgery. In another embodiment, the anti-obesity treatment is a physical exercise program.

In one embodiment, the invention provides a method for treatment, prevention or management of diabetes mellitus in a subject in need thereof, the method comprising the step of administering an effective amount of a GOAT inhibitor and/or an effective amount of a ghrelin receptor antagonist and/or inverse agonist. The diabetes mellitus can be type I or II.

In another embodiment, the invention provides a method for the modulation of ghrelin receptor in a subject in need thereof, the method comprising the step of administering an effective amount of a GOAT inhibitor and an effective amount of a ghrelin receptor antagonist and/or inverse agonist. In one embodiment, the invention provides a method for the modulation of ghrelin receptor in a subject in need thereof, the method comprising administering an effective amount of a GOAT inhibitor. In another embodiment, the invention provides a method for the modulation of ghrelin receptor in a subject in need thereof, the method comprising administering an effective amount of a ghrelin receptor antagonist and/or inverse agonist.

In another embodiment, the invention provides a method for treatment, prevention, or management of metabolic syndrome in a subject in need thereof, the method comprising the step of administering an effective amount of a GOAT inhibitor and an effective amount of a ghrelin receptor antagonist and/or inverse agonist.

In another embodiment, the invention provides a method for treatment, prevention, or management of cancer in a subject in need thereof, the method comprising the step of administering an effective amount of a GOAT inhibitor and an effective amount of a ghrelin receptor antagonist and/or inverse agonist. In one embodiment, the invention provides a method for treatment, prevention, or management of cancer in a subject in need thereof, the method comprising administering an effective amount of a GOAT inhibitor. In another embodiment, the invention provides a method for treatment, prevention, or management of cancer in a subject in need thereof, the method comprising administering an effective amount of a ghrelin receptor antagonist and/or inverse agonist.

In one embodiment, the GOAT inhibitor comprises an octanoylated peptide and the octanoylation is at position three of the peptide. In another embodiment, the GOAT inhibitor comprises an octanoylated pentapeptide and wherein the octanoylation is at position three of the pentapeptide. In one embodiment, the octanoylated ghrelin pentapeptide is Gly-Ser-Ser(Oct)-Phe-Leu (SEQ ID NO: 1), or Gly-Ser-Dap(Oct)-Phe-Leu (SEQ ID NO: 2). Ser(Oct) and Dap(Oct) represent octanoylated serine and octanoylated diaminopropionic acid respectively.

In one embodiment, the ghrelin receptor antagonist is selected from the group consisting of Tyr-DTrp-DLys-Trp-DPhe-NH$_2$ (SEQ ID NO: 11), Tyr-DTrp-Lys-Trp-DPhe-NH$_2$ (SEQ ID NO: 12), His-DTrp-DLys-Trp-DPhe-NH$_2$ (SEQ ID NO: 13), His-DTrp-DLys-Phe-DTrp-NH$_2$ (SEQ ID NO: 14), His-DTrp-DArg-Trp-DPhe-NH$_2$ (SEQ ID NO: 15), His-DTrp-DLys-Trp-DPhe-Lys-NH$_2$ (SEQ ID NO: 16), DesaminoTyr-DTrp-Ala-Trp-DPhe-NH$_2$ (SEQ ID NO: 17), DesaminoTyr-DTrp-DLys-Trp-DPhe-NH$_2$ (SEQ ID NO: 18), DeaminoTyr-DTrp-Ser-Trp-DPhe-Lys-NH$_2$ (SEQ ID NO: 19), DesaminoTyr-DTrp-Ser-Trp-DPhe-NH$_2$ (SEQ ID NO: 20), His-DTrp-DTrp-Phe-Met-NH$_2$ (SEQ ID NO: 21), Tyr-DTrp-DTrp-Phe-Phe-NH$_2$ (SEQ ID NO: 22), Glyψ[CH$_2$NH]-DβNal-Ala-Trp-DPhe-Lys-NH$_2$ (SEQ ID NO: 23), Glyψ[CH$_2$NH]-DβNal-DLys-Trp-DPhe-Lys-NH$_2$ (SEQ ID NO: 24), DAla-DβNal-DLys-DTrp-Phe-Lys-NH$_2$ (SEQ ID NO: 25), His-DβNal-DLys-Trp-DPhe-Lys-NH$_2$ (SEQ ID NO: 26), Ala-His-DTrp-DLys-Trp-DPhe-Lys-NH$_2$ (SEQ ID NO: 27), Alaψ[CH$_2$NH]-DβNal-Ala-Trp-DPhe-Lys-NH$_2$ (SEQ ID NO: 28), DβNal-Ala-Trp-DPhe-Ala-NH$_2$ (SEQ ID NO: 29), DAla-DcyclohexylAla-Ala-Phe-DPhe-Nle-NH$_2$ (SEQ ID NO: 30), DcyclohexylAla-Ala-Phe-DTrp-Lys-NH$_2$ (SEQ ID NO: 31), DAla-DβNal-Ala-Thr-DThr-Lys-NH$_2$ (SEQ ID NO: 32), DcyclohexylAla-Ala-Trp-DPhe-NH$_2$ (SEQ ID NO: 33), DAla-DβNal-Ala-Ala-DAla-Lys-NH$_2$ (SEQ ID NO: 34), DβNal-Ala-Trp-DPhe-Leu-NH$_2$ (SEQ ID NO: 35), His-DTrp-Phe-Trp-DPhe-Lys-NH$_2$ (SEQ ID NO: 36), DAla-DβNal-DAla-DTrp-Phe-Lys-NH$_2$ (SEQ ID NO: 37), βAla-Trp-DAla-DTrp-Phe-NH$_2$ (SEQ ID NO: 38), His-Trp-DAla-DTrp-Phe-LysNH$_2$ (SEQ ID NO: 39), DLys-Dβ-Nal-Ala-Trp-DPhe-Lys-NH$_2$ (SEQ ID NO: 40), DAla-Dβ-Nal-DLys-DTrp-Phe-Lys-NH$_2$ (SEQ ID NO: 41), Tyr-DAla-Phe-Aib-NH$_2$ (SEQ ID NO: 42), Tyr-DAla-Sar-NMePhe-NH$_2$ (SEQ ID NO: 43), αγAbu-DTrp-DTrp-Ser-NH$_2$ (SEQ ID NO: 44), αγAbu-DTrp-DTrp-Lys-NH$_2$ (SEQ ID NO: 45), αγAbu-DTrp-DTrp-Orn-NH$_2$ (SEQ ID NO: 46), αAbu-DTrp-DTrp-Orn-NH$_2$ (SEQ ID NO: 47), DThr-DαNal-DTrp-DPro-Arg-NH$_2$ (SEQ ID NO: 48), DAla-Ala-DAla-DTrp-Phe-Lys-NH$_2$ (SEQ ID NO: 49), Alaψ[CH$_2$NH]His-DTrp-Ala-Trp-DPhe-Lys-NH$_2$ (SEQ ID NO: 50), Lys-DHis-DTrp-Phe-NH$_2$ (SEQ ID NO: 51), γAbu-DTrp-DTrp-Orn-NH$_2$ (SEQ ID NO: 52), inip-Trp-Trp-Phe-NH$_2$ (SEQ ID NO: 53), Ac-DTrp-Phe-DTrp-Leu-NH$_2$ (SEQ ID NO: 54), Ac-DTrp-Phe-DTrp-Lys-NH$_2$ (SEQ ID NO: 55), Ac-DTrp-DTrp-Lys-NH$_2$ (SEQ ID NO: 56), DLys-Tyr-DTrp-DTrp-Phe-Lys-NH$_2$ (SEQ ID NO: 57), Ac-DβNal-Leu-Pro-NH$_2$ (SEQ ID NO: 58), βAla-Trp-DTrp-DTrp-Orn-NH$_2$ (SEQ ID NO: 59), DVal-DαNal-DTrp-Phe-Arg-NH$_2$ (SEQ ID NO: 60), DLeu-DαNal-DTrp-Phe-Arg-NH$_2$ (SEQ ID NO: 61), CyclohexylAla-DαNal-DTrp-Phe-Arg-NH$_2$ (SEQ ID NO: 62), DTrp-DαNal-DTrp-Phe-Arg-NH$_2$ (SEQ ID NO: 63), DAla-DβNal-DPro-Phe-Arg-NH$_2$ (SEQ ID NO: 64), Ac-Dα-Nal-DTrp-Phe-Arg-NH$_2$ (SEQ ID NO: 65), DαNal-DTrp-Phe-Arg-NH$_2$ (SEQ ID NO: 66), His-DTrp-DTrp-Lys-NH$_2$ (SEQ ID NO: 67), Ac-DβNal-DTrp-NH$_2$ (SEQ ID NO: 68), αAib-DTrp-DcyclohexylAla-NH$_2$ (SEQ ID NO: 69), αAib-DTrp-DAla-cyclohexylAla-NH$_2$ (SEQ ID NO: 70), DAla-DcyclohexylAla-Ala-Ala-Phe-DPhe-Nle-NH$_2$ (SEQ ID NO: 71), DPhe-Ala-Phe-DPal—NH$_2$ (SEQ ID NO: 72), DPhe-Ala-Phe-DPhe-Lys-NH$_2$ (SEQ ID NO: 73), DLys-Tyr-DTrp-DTrp-Phe-NH$_2$ (SEQ ID NO: 74), Ac-DLys-Tyr-DTrp-DTrp-Phe-NH$_2$ (SEQ ID NO: 75), Arg-DTrp-Leu-Tyr-Trp-Pro (cyclic Arg-Pro) (SEQ ID NO: 76), Ac-DβNal-PicLys-ILys-DPhe-NH$_2$ (SEQ ID NO: 77), DPal-Phe-DTrp-Phe-Met-NH$_2$ (SEQ ID NO: 78), DPhe-Trp-DPhe-Phe-Met-NH$_2$ (SEQ ID NO: 79), DPal-Trp-DPhe-Phe-Met-NH$_2$ (SEQ ID NO: 80), βAla-Pal-DTrp-DTrp-Orn-NH$_2$ (SEQ ID NO: 81), αγAbu-Trp-DTrp-DTrp-Orn-NH$_2$ (SEQ ID NO: 82), βAla-Trp-DTrp-DTrp-Lys-NH$_2$ (SEQ ID NO: 83), γAbu-Trp-DTrp-DTrp-Orn-NH$_2$ (SEQ ID NO: 84), Ava-Trp-DTrp-DTrp-Orn-NH$_2$ (SEQ ID NO: 85), DLys-Tyr-DTrp-Ala-Trp-DPhe-NH$_2$ (SEQ ID NO: 86), His-DTrp-DArg-Trp-DPhe-NH$_2$ (SEQ ID NO: 87), <Glu-His-Trp-DSer-DArg-NH$_2$ (SEQ ID NO: 88), DPhe-DPhe-DTrp-Met-DLys-NH$_2$ (SEQ ID NO: 89), Gly-Met-Ala-Gly-Ser-(Dap-Oct)-Phe-Leu-Ser-Pro-Glu-His-NH$_2$ (SEQ ID NO: 3), Gly-Met-Ala-Gly-Ser-(Dap-palmityl)-Phe-Leu-Ser-Pro-Glu-His-NH$_2$ (SEQ ID NO: 4), O-(2-methylallyl)benzophenone oxime, (R)-2-amino-3-(1H-indol-3-yl)-1-(4-phenylpiperidin-1-yl)propan-1-one, N—((R)-1-((R)-1-((S)-3-(1H-indol-3-yl)-1-oxo-1-(4-phenylpiperidin-1-yl)propan-2-ylamino)-6-amino-1-oxohexan-2-ylamino)-3-hydroxy-1-oxopropan-2-yl)benzamide, (S)—N—((S)-3-(1H-indol-3-yl)-1-oxo-1-(4-phenylpiperidin-1-yl)propan-2-yl)-6-acetamido-2-((S)-2-amino-3-(benzyloxy)propanamido)hexanamide, (S)—N—((R)-3-(1H-indol-3-yl)-1-oxo-1-(4-phenylpiperidin-1-yl)propan-2-yl)-2-((S)-2-acetamido-3-(benzyloxy)propanamido)-6-aminohexanamide, (R)—N-(3-(1H-indol-3-yl)-1-(4-(2-methoxyphenyl)piperidin-1-yl)-1-oxopropan-2-yl)-4-aminobutanamide, (R)—N-(3-(1H-indol-3-yl)-1-(4-(2-methoxyphenyl)piperidin-1-yl)-1-oxopropan-2-yl)-2-amino-2-methylpropanamide, methyl 3-(p-tolylcarbamoyl)-2-naphthoate, ethyl 3-(4-(2-methoxyphenyl)piperidine-1-carbonyl)-2-naphthoate, 3-(2-methoxyphenylcarbamoyl)-2-naphthoate, (S)-2,4-diamino-N—((R)-3-(naphthalen-2-ylmethoxy)-1-oxo-1-(4-phenylpiperidin-1-yl)propan-2-yl)butanamide, naphthalene-2,3-diylbis((4-(2-methoxyphenyl)piperazin-1-yl)methanone), (R)-2-amino-N-(3-(benzyloxy)-1-oxo-1-(4-phenylpiperazin-1-yl)propan-2-yl)-2- methylpropanamide, or (R)-2-amino-3-(benzyloxy)-1-(4-phenylpiperazin-1-yl)propan-1-one, and pharmaceutically acceptable salts, prodrugs, or active metabolites thereof.

In some embodiments, the ghrelin receptor antagonist is Gly-Met-Ala-Gly-Ser-(Dap-Oct)-Phe-Leu-Ser-Pro-Glu-His-NH$_2$ (SEQ ID NO: 3).

BRIEF DESCRIPTION OF THE FIGURES

FIG. 10 discloses "GMAGS" as residues 1-5 of SEQ ID NOS 3 and 4.

FIG. 11 discloses "GMAGS" as residues 1-5 of SEQ ID NOS 3 and 4.

DETAILED DESCRIPTION OF THE INVENTION

Figure 1A:
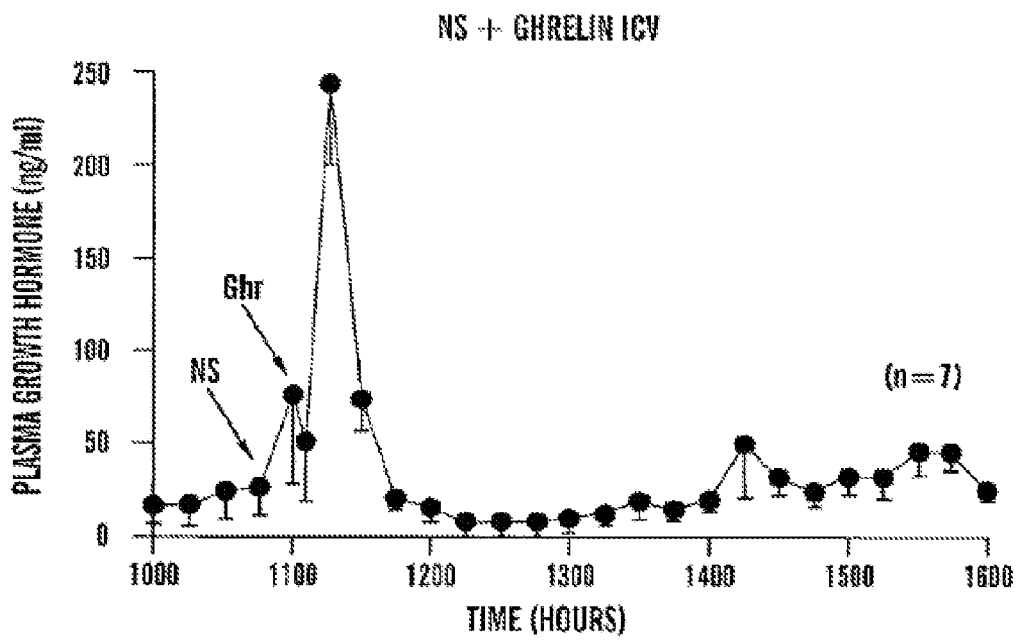
FIGS. 1A and 1B show mean plasma GH responses to 500 ng ghrelin administered icy 15 min after the icy injection of 5 μg GHS-A (FIG. 1B) or normal saline (FIG. 1A). Central pretreatment with GHS-A abolished the stimulatory action of ghrelin on GH release compared with normal saline i.c.v. pretreated controls. Values are the mean±SE. The number of animals in each group is shown in parentheses. Arrows indicate the times of i.c.v. injections.

The present invention provides novel strategies for inhibiting and/or disrupting the GHS-R 1a signaling pathway for regulating GH secretion, appetite, and body weight, and for the treatment of metabolic diseases and disorders such as obesity, overeating, diabetes mellitus, unregulated cell proliferation, and for the inhibition of growth hormone secreted from tumors such as pituitary, prostate, medullary thyroid carcinomas, osteoblast, pancreatic and hepatoma. The inhibition and/or disruption of the GHS-R signaling pathway can be approached in several ways: (1) inhibiting of synthesis of the active form of ghrelin, an endogenous peptide ligand of the pathway and (2) disrupting the constitutively active GHS-R 1a signaling pathway using antagonists and/or inverse agonists. These approaches can be applied individually or together.

Ghrelin, a 28 amino acid, octanoylated, appetite-stimulating peptide hormone, is secreted by the food-deprived stomach. It is the endogenous ligand for GHS-R 1a and therefore, the activator ligand of the GHS-R 1a signaling pathway. Ghrelin is synthesized as a preprohormone, then proteolytically processed to yield a 28-amino acid peptide. An interesting and unique modification is then imposed on the 28-amino acid peptide hormone during synthesis. This peptide hormone requires acylation with an eight-carbon fatty acid, octanoate, at amino acid residue serine-3 (Bednarek M A. et al., 2000, J Med. Chem., 43:4370-6; Kojima et al., 1999, Nature, 402:656-60, content of both of which is herein incorporated by reference). This modification is necessary for biologic activity, i.e. activation of intracellular signaling that is mediated through the seven transmembrane G (7TMG) protein coupled ghrelin receptor (GHS-R 1a)—both in vitro and in vivo (Kojima et al., 1999, Nature, 402:656-60; Nakazato et al., 2001, Nature, 409:194-8.; Tschop et al., 2000, Nature, 407:908-13, content of all of which is herein incorporated by reference). Ghrelin that is deleted of the octanoate, known as desoctanoylated ghrelin, is biologically inactive.

Recently, the membrane bound acyltransferase that catalyses the addition of octanoate to serine-3 was identified. The enzyme is named ghrelin O-acyltransferase (GOAT). GOAT was shown to also transfer octanoyl to a pentapeptide containing only the N-terminal five amino acids of proghrelin, the 94 amino acid protein precursor of ghrelin (Yang J, et. al., 2008, Proc. Natl. Acad. Sci. USA. 105:10750-5, content of which is herein incorporated by reference). Yang, et, al. showed that GOAT activity could be inhibited by an octanoylated ghrelin pentapeptide, and its potency was enhanced 45-fold when the octanoylated serine-3 was replaced by octanoylated diaminopropionic acid.

Accordingly, strategies for inhibiting the GHS-R 1a signaling pathway encompass preventing the synthesis of an active form of ghrelin via inhibiting the activity of GOAT with an octanoylated ghrelin pentapeptide or octanoylated diaminopropionic peptides and the likes.

Synthesis of ghrelin occurs predominantly in P/D1 epithelial cells lining the fundus of the stomach and epsilon cells of the pancreas that stimulates appetite. Ghrelin levels increase before meals and decrease after meals. Smaller amounts of ghrelin is produced in the placenta, kidney, pituitary and hypothalamus. In addition, certain tumors and cancers have been shown to express ghrelin although the normal tissue do not: islet cell tumors, medullary thyroid carcinomas, pituitary adenoma, thyroid tumor, and pancreatic and gastrointestinal endocrine tumors (Korbonits M, et. al. 2001, J. Clin. Endocrinol. Metab. 86:881-887; Papotti M, et. al., 2001, J. Clin. Endocrinol. Metab. 86:5052-5059; Kanamoto N, et. al., 2001, J. Clin. Endocrinol. Metab. 86:4984-4990; Korbonits M, et. al., 2001, Endocrine 14:101-104; Volante M, et. al. 2002, J. Clin. Endocrinol. Metab. 87:1300-1308, content of all of which is herein incorporated by reference).

The ghrelin receptor, GHS-R 1a, is found in cells within the anterior pituitary which when activated, potently stimulates secretion of growth hormone. Ghrelin receptors are present on the cells in the pituitary that secrete growth hormone, and also have been identified in the hypothalamus, heart and adipose tissue.

Interaction of the active octanoylated peptide hormone with its receptor, the ghrelin receptor, GHS-R 1a, leads to the release of growth hormone and the positive activation of the GH axis. The ghrelin/GHS-R 1a signaling pathway is also involved in the regulation of energy balance in the body. Regulation of energy balance comprises ghrelin functions to increase hunger though its action on hypothalamic feeding centers, suppress fat utilization in adipose tissue, stimulating gastric emptying and having a variety of positive effects on cardiovascular function (e.g. increased cardiac output). The ultimate effect of ghrelin is the stimulation of appetite, intake of food and the secretion of growth hormone. Thus, any strategies for inhibiting and/or disrupting the ghrelin/GHS-R 1a signaling pathway which includes reducing the amount of circulating ghrelin can be more effective in the treatment of metabolic diseases and disorders associated with abnormal appetite and intake of food, energy balance and regulation, and/or ectopic release of growth hormone and/or ghrelin such as induction by tumors.

In one embodiment, the method for inhibiting and/or disrupting the ghrelin/GHS-R 1a signaling pathway comprises inhibiting the synthesis of an active octanoylated ghrelin comprising inhibiting a ghrelin O-acyltransferase (GOAT).

In one embodiment, the method for inhibiting and/or disrupting the ghrelin/GHS-R 1a signaling pathway comprises inhibiting the constitutive ghrelin/GHS-R 1a signaling pathway with an inverse agonist.

In one embodiment, the method for inhibiting and/or disrupting the ghrelin/GHS-R 1a signaling pathway comprises inhibiting the constitutive ghrelin/GHS-R 1a signaling pathway comprising inhibiting the interaction of GHS-R 1a and its ligand, e.g. ghrelin, with an antagonist.

In one embodiment, the method for inhibiting and/or disrupting the ghrelin/GHS-R 1a signaling pathway comprises simultaneously inhibiting the synthesis of active octanoylated ghrelin and inhibiting the interaction of the active octanoylated hormone with its receptor, the ghrelin receptor, GHS-R 1a and/or the constitutive GHS-R 1a signaling pathway. For example, by administering an effective amount of a ghrelin O-acyltransferase (GOAT) inhibitor and an effective amount of a ghrelin receptor antagonist and/or inverse agonist. While not wishing to be bound by theory, inhibiting the synthesis of active octanoylated ghrelin serves to reduce the amount of circulating ghrelin that is available for binding to and activating the ghrelin receptor, GHS-R 1a, and the associated signaling pathway. Inhibiting the interaction of the active octanoylated ghrelin with GHS-R 1a serves to inhibit the ghrelin/GHS-R 1a signaling pathway. The inverse agonist serves to reduce the amount of constitutive signaling from the pathway. The combined inhibition strategy work synergistically to attenuates GH pulses and reduces food intake in mammals.

The serine-3 of ghrelin is acylated with an eight-carbon fatty acid, octanoate, which is required for its endocrine actions. Ghrelin that is deleted of the octanoate, known as desoctanoylated ghrelin is biologically inactive. The membrane bound acyltransferase that catalyses the addition of octanoate to Serine-3 (Yang, et, al. 2008,) named ghrelin O-acyltransferase (GOAT). GOAT was shown to also transfer octanoyl to a pentapeptide containing only the N-terminal five amino acids of proghrelin, the 94 amino acid protein precursor of ghrelin (Yang, et, al. 2008). Yang, et, al. 2008 showed that GOAT activity could be inhibited by an octanoylated ghrelin pentapeptide, and its potency was enhanced 45-fold when the octanoylated serine-3 was replaced by octanoylated diaminopropionic acid. Accordingly, the synthesis of active octanoylated ghrelin can be inhibited with an octanoylated ghrelin pentapeptide or modified versions thereof, such as an octanoylated diaminopropionic peptide.

The interaction of the active octanoylated hormone with its receptor, the ghrelin receptor, GHS-R 1a, can be inhibited with a ghrelin receptor antagonist and/or a growth hormone secretatogue antagonist and/or inverse agonist.

In one embodiment, provided herein is a method of treatment, prevention or management of obesity in a subject, the method comprising administering an effective amount of a ghrelin O-acyltransferase (GOAT) inhibitor and an effective amount of a ghrelin receptor antagonist and/or a growth hormone secretatogue antagonist and/or inverse agonist.

In one embodiment, provided herein is a method of treatment, prevention or management of diabetes mellitus in a subject, the method comprising administering an effective amount of a ghrelin O-acyltransferase (GOAT) inhibitor and an effective amount of a ghrelin receptor antagonist and/or a growth hormone secretatogue antagonist and/or inverse agonist.

In one embodiment, provided herein is a method of treatment, prevention or management of metabolic syndrome in a subject, the method comprising administering an effective amount of a ghrelin O-acyltransferase (GOAT) inhibitor and an effective amount of a ghrelin receptor antagonist and/or a growth hormone secretatogue antagonist and/or inverse agonist.

In one embodiment, provided herein is a method of treatment, prevention or management of cancer in a subject, the method comprising administering an effective amount of a ghrelin O-acyltransferase (GOAT) inhibitor and an effective amount of a ghrelin receptor antagonist and/or a growth hormone secretatogue antagonist and/or inverse agonist. In one embodiment, the method for treatment, prevention, or management of cancer in a subject in need thereof comprises administering an effective amount of a GOAT inhibitor. In another embodiment, the method for treatment, prevention, or management of cancer in a subject in need thereof comprises administering an effective amount of a ghrelin receptor antagonist and/or inverse agonist and/or a growth hormone secretatogue antagonist.

In some embodiments, the methods of treatment, prevention or management of obesity, diabetes mellitus, metabolic syndrome, or cancer in a subject in need hereof comprise administering an effective amount of a ghrelin O-acyltransferase (GOAT) inhibitor.

In other embodiments, the methods of treatment, prevention or management of obesity, diabetes mellitus, metabolic syndrome, or cancer in a subject in need hereof comprise administering an effective amount of a ghrelin receptor antagonist and/or a growth hormone secretatogue antagonist and/or inverse agonist.

In one embodiment, provided herein is a method of modulating a ghrelin receptor in a subject, the method comprising administering an effective amount of a ghrelin O-acyltransferase (GOAT) inhibitor and an effective amount of a ghrelin receptor antagonist and/or a growth hormone secretatogue antagonist. In another embodiment, provided herein is a method of modulating a ghrelin receptor in a subject, the method comprising administering an effective amount of a ghrelin O-acyltransferase (GOAT) inhibitor. In yet another embodiment, provided herein is a method of modulating a ghrelin receptor in a subject, the method comprising administering an effective amount of a ghrelin receptor antagonist and/or inverse agonist.

As used herein, the term "modulation" specifically refers to the inhibition of ghrelin receptor activity such as ghrelin ligand binding, message transduction, increased intracellular inositol 1,4,5-trisphosphate (IP3) levels and any activity associated with the activation and generation of intracellular signals in the ghrelin/ghrelin receptor signaling pathway. Methods of receptor-ligand binding and determining levels of IP3 are well known in the art, e.g., as described by AR Prasad, et al., 1993, Circulation Research, 72:827-836, content of which is herein incorporated by reference.

In one embodiment, provided herein is a method of reducing a desire of a human subject to consume calories following gastric banding or gastric bypass surgery, the method comprising administering an effective amount of a ghrelin O-acyltransferase (GOAT) inhibitor and an effective amount of a ghrelin receptor antagonist and/or a growth hormone secretatogue antagonist and/or inverse agonist. In another embodiment, the method of reducing a desire of a human subject to consume calories following gastric banding or gastric bypass surgery comprises administering an effective amount of a ghrelin O-acyltransferase (GOAT) inhibitor. In another embodiment, the method of reducing a desire of a human subject to consume calories following gastric banding or gastric bypass surgery comprises administering an effective amount of a ghrelin receptor antagonist and/or a growth hormone secretatogue antagonist and/or inverse agonist.

In one embodiment, provided herein is a method of treating hormonally functional endocrine or non-endocrine tumors in a subject, the method comprising administering an effective amount of a ghrelin O-acyltransferase (GOAT) inhibitor and an effective amount of a ghrelin receptor antagonist and/or a growth hormone secretatogue antagonist and/or inverse agonist. Such as, but not limited to, pituitary tumors, including ACTH-secreting pituitary tumors, in a mammal. In another embodiment, the method of treating hormonally functional endocrine or non-endocrine tumors in a subject comprises administering an effective amount of a ghrelin O-acyltransferase (GOAT) inhibitor. In another embodiment, the method of treating hormonally functional endocrine or non-endocrine tumors in a subject comprises administering an effective amount of a ghrelin receptor antagonist and/or a growth hormone secretatogue antagonist and/or inverse agonist. The inventive methods involve administering to the mammal having or at risk for developing a pituitary tumor a therapeutically effective amount of a ghrelin O-acyltransferase (GOAT) inhibitor and/or an effective amount of a ghrelin receptor antagonist and/or a growth hormone secretatogue antagonist. In one embodiment, the ghrelin receptor antagonist and/or GOAT inhibitor are administered in combination with other compounds useful in the treatment of pituitary tumor such as, for example, PPARγ ligands. PPARγ ligands include thiazolidinediones (TZDs), such as troglitazone, pioglitazone, and rosiglitazone.

In one embodiment, provided herein is a method for the treatment of tumors that produce prolactin in a subject, the method comprising administering an effective amount of a ghrelin O-acyltransferase (GOAT) inhibitor and an effective amount of a ghrelin receptor antagonist and/or a growth hormone secretatogue antagonist and/or inverse agonist. In another embodiment, the method for the treatment of tumors that produce prolactin in a subject comprises administering an effective amount of a ghrelin O-acyltransferase (GOAT) inhibitor. In another embodiment, the method for the treatment of tumors that produce prolactin in a subject comprises administering an effective amount of a ghrelin receptor antagonist and/or a growth hormone secretatogue antagonist and/or inverse agonist. Such tumors include, but are not limited to, breast, pituitary, and prostate cancer. A therapeutically effective amount of a GOAT inhibitor and/or an effective amount of a ghrelin receptor antagonist and/or a growth hormone secretatogue antagonist are administered to a subject with or at risk for developing a tumor that produces prolactin.

In one embodiment, provided herein is a method of inhibiting adrenacorticotropic hormone in a subject in need thereof, the method comprising administering an effective amount of a ghrelin O-acyltransferase (GOAT) inhibitor and an effective amount of a ghrelin receptor antagonist and/or a growth hormone secretatogue antagonist and/or inverse agonist. In another embodiment, the method of inhibiting adrenacorticotropic hormone in a subject in need thereof comprises administering an effective amount of a ghrelin O-acyltransferase (GOAT) inhibitor. In another embodiment, the method of inhibiting adrenacorticotropic hormone in a subject in need thereof comprises administering an effective amount of a ghrelin receptor antagonist and/or a growth hormone secretatogue antagonist and/or inverse agonist. A subject in need of inhibiting adrenacorticotropic hormone is one with too much adrenacorticotropic hormone. Excessive adrenacorticotropic hormone (ACTH) results in Cushing's disease. Physical symptoms of the disease include but are not limited to widened face with acne and flushing, fatty deposits over back of neck, stretch marks, easy bruising, hair growth, diabetes mellitus, muscle loss and fatigue, and depression and psychosis. A routine blood test that is well known to one skilled in the art can be used to determine the level of the hormone in the individual. Adrenacorticotropic hormone are produced by neuroendocrine tumors, carcinoid, pituitary and pancreatic tumors. Accordingly, in another embodiment, provided herein is a method of treating ectopic neuroendocrine tumors, the method comprising administering an effective amount of a ghrelin O-acyltransferase (GOAT) inhibitor, and/or an effective amount of a ghrelin receptor antagonist and/or a growth hormone secretatogue antagonist and/or inverse agonist.

In one embodiment, provided herein is a method of inhibiting signaling via subtype receptor of ghrelin in addition to GHS-type 1 receptor in a subject in need thereof, the method comprising administering an effective amount of a ghrelin O-acyltransferase (GOAT) inhibitor and an effective amount of a ghrelin receptor antagonist and/or a growth hormone secretatogue antagonist and/or inverse agonist. In another embodiment, the method of inhibiting signaling via subtype receptor of ghrelin in addition to GHS-type 1 receptor in a subject in need thereof comprises administering an effective amount of a ghrelin O-acyltransferase (GOAT) inhibitor. In another embodiment, the method of inhibiting signaling via subtype receptor of ghrelin in addition to GHS-type 1 receptor in a subject in need thereof comprises administering an effective amount of a ghrelin receptor antagonist and/or a growth hormone secretatogue antagonist and/or inverse agonist. Skilled artisan is well aware of diseases and disorders associated with these subtype receptors, e.g. subtype 1b receptor. For example, a review of the subtype receptors is found in J. P. Camiña, 2005, J. Neuroendocrin., 18: 65-76, content of which is herein incorporated by reference. Certain cancers such as prostate cancer, osteoblast cancer, pancreatic cancer, adenocarcinomas and hepatoma cells are associated with different subtype of GHS-type 1 receptor. Accordingly, in another embodiment, provided herein is a method of treating diseases and disorders associated with ghrelin subtype receptors in a subject in need thereof, the method comprising administering an effective amount of a ghrelin O-acyltransferase (GOAT) inhibitor and an effective amount of a ghrelin receptor antagonist and/or a growth hormone secretatogue antagonist and/or inverse agonist. In one embodiment, the method of treating diseases and disorders associated with ghrelin subtype receptors in a subject in need thereof comprises administering an effective amount of a ghrelin O-acyltransferase (GOAT) inhibitor. In one embodiment, the method of treating diseases and disorders associated with ghrelin subtype receptors in a subject in need thereof comprises administering an effective amount of a ghrelin receptor antagonist and/or a growth hormone secretatogue antagonist and/or inverse agonist.

In one embodiment, provided herein is a method of treatment, prevention or management of obesity related diseases and disorders in a subject, the method comprising administering an effective amount of a ghrelin O-acyltransferase (GOAT) inhibitor and an effective amount of a ghrelin receptor antagonist and/or a growth hormone secretatogue antagonist and/or inverse agonist. In one embodiment, the method of treatment, prevention or management of obesity related diseases and disorders in a subject comprises administering an effective amount of a ghrelin O-acyltransferase (GOAT) inhibitor. In another embodiment, the method of treatment, prevention or management of obesity related diseases and disorders in a subject comprises administering an effective amount of a ghrelin receptor antagonist and/or a growth hormone secretatogue antagonist and/or inverse agonist. Obesity related diseases and disorders include, but not limited to overeating, diabetes mellitus, metabolic syndrome, hypertension, elevated plasma insulin concentrations, insulin resistance, dyslipidemias, and hyperlipidemia.

In some embodiments, the methods of treatment, prevention or management of obesity, or obesity related diseases and disorders in a subject further comprises administering an anti-obesity treatment. In some embodiment, the anti-obesity treatment is a combination of dietary restriction therapy with a 5HT (serotonin) transporter inhibitor, a NE (norepinephrine) transporter inhibitor, a CB-1 (cannabinoid-1) antagonist/inverse agonist, a H3 (histamine H3) antagonist/inverse agonist, a MCH1R (melanin concentrating hormone 1R) antagonist, a MCH2R agonist/antagonist, a NPY1 antagonist, a leptin, a leptin derivative, a leptin analog, PYY(1-36), PYY (3-36), an opioid antagonist, an orexin antagonist, a BRS3 (bombesin receptor subtype 3) agonist, a CCK-A (cholecystokinin-A) agonist, a CNTF (Ciliary neurotrophic factor), a CNTF derivative, a lipase drug inhibitor, an inhibitor of food intake, an incretin, an incretin agonist, an incretin analog or an incretin mimic administered simultaneously, concurrently or sequentially.

Examples of the inhibitor of food intake include but are not limited to gastrointestinal hormone glucagon-like-peptide (Glip-1/Glip-2) and the intestinal preproghrelin derived peptide hormone oxyntomodulin and their analogs, derivatives, mimics. Examples of incretins and its agonists, analogs, derivatives, or mimics capable of inducing a decrease in food intake, include but are not limited to GLP-1 receptor agonists exenatide (synthetic mimetic of exendin-4), liraglutide, or enzyme glucagon-like peptide-1(GLP-1) inhibitors of the dipeptidyl peptidase DPP-4 type, i.e., sitagliptin, vildagliptin, saxagliptin, which slow degradation of GLP-1 and prolong the actions of GLP-1.

The incretin hormones GLP-1 (glucagon-like peptide-1) and GIP are produced by the endocrine cells of the intestine following ingestion of food. GLP-1 and GIP stimulate insulin secretion from the beta cells of the islets of Langerhans in the pancreas. Only GLP-1 causes insulin secretion in the diabetic state. Exenatide, a synthetic version of exendin-4, a hormone found in the saliva of the Gila monster, bears a 50% amino acid homology to GLP-1 and displays biological properties similar to human glucagon-like peptide-1 (GLP-1). It has a longer half-life in vivo. exenatide enhances glucose-dependent insulin secretion by the pancreatic beta-cell, suppresses inappropriately elevated glucagon secretion, and slows gastric emptying.

Accordingly, any treatment intervention that increases the GLP-1 and/or GIP stimulated activities in vivo is contemplated, e.g. GLP-1 analogs, derivatives, mimics and also inhibitors to slow GLP-1 degradation and prolong the actions of GLP-1.

Leptin is a 16 kDa protein hormone that plays a key role in regulating energy intake and energy expenditure, including appetite and metabolism. Leptin is produced in white adipose tissue—the major source—brown adipose tissue, placenta (syncytiotrophoblasts), ovaries, skeletal muscle, stomach (lower part of fundic glands), mammary epithelial cells, bone marrow, pituitary and liver. Leptin circulates at levels proportional to body fat. It enters the central nervous system (CNS) in proportion to its plasma concentration. Its receptors are found in brain neurons involved in regulating energy intake and expenditure. Leptin signals to the brain that the body has had enough to eat, or satiety, thus reducing appetite.

Leptin can be recombinantly produced as described in e.g., WO 96/05309; U.S. Pat. No. 5,552,522; U.S. Pat. No. 5,552, 523; and U.S. Pat. No. 5,552,524, the content of all of which is herein incorporated by reference. Biologically active derivatives or analogs of leptin can also be referred as leptin peptide mimetics. These mimetics can be designed and produced by techniques known to those of skill in the art. (See e.g., U.S. Pat. Nos. 4,612,132; 5,643,873, 5,654,276 and 5,866,547, content of all of which is herein incorporated by reference).

Peptide YY (PYY) is a short (36 amino acid) protein released by cells in the ileum and colon in response to feeding. A small amount of PYY about 1-10 percent in esophagus, stomach, duodenum and jejunum. It is also known as PYY, peptide tyrosine tyrosine, or pancreatic peptide YY(3-36). There are two major forms of Peptide YY: PYY(1-36) and PYY(3-36). In humans it reduce appetites. PYY concentration in the circulation increases postprandially (after food ingestion) and decreases by fasting.

In other embodiments, the methods of treatment, prevention or management of obesity, or obesity related diseases and disorders in a subject further comprises a surgical or mechanical procedure used for the treatment of obesity. Such procedures include but not limited to bariactric surgeries such as gastric stapling or gastroplasty, and gastric bypass.

In some embodiments of the treatment, prevention or management of diabetes mellitus or metabolic syndrome described herein, the ghrelin secretory receptor inhibitors, e.g. ghrelin receptor antagonist or inverse agonist can be administered alone, sequentially, or concomitantly with a biguanide (Metformin), a peroxisome proliferator activator-receptor alpha (PPAR-alpha) ligand or PPAR-gamma ligand such as pioglitazone or rosiglitazone which increase circulating adiponectin levels and/or regulate/augment phosphorylation of adenosine monophosphate protein kinase (AMP-kinase), a key intracellular regulator of energy balance, and agents that lower peripheral circulating glucose levels primarily but not exclusively in Type 2 patients with diabetes mellitus. Biguanides are well known oral antihyperglycemic drugs used for diabetes mellitus or prediabetes treatment.

In some embodiments, the ghrelin O-acyltransferase (GOAT) inhibitor in any of the methods described herein comprises an octanoylated ghrelin pentapeptide, and wherein the octanoylation is at position three of the pentapeptide. Preferably, the octanoylation is at the side chain of the residue at position three. In some embodiments, the octanoylated ghrelin pentapeptide is Gly-Ser-Ser(Oct)-Phe-Leu (SEQ ID NO: 1).

In some embodiments, the octanoylated ghrelin pentapeptide is Gly-Ser-Dap(Oct)-Phe-Leu (SEQ ID NO: 2).

Other GOAT inhibitors amenable to the present invention are described, for example, in U.S. Pat. Pub. No.: 2010/0086955 and Int. Pat. Pub. No.: WO2010/039461, content of both of which is herein incorporated by reference.

In some embodiment, a mixture of GOAT inhibitors is used in the methods described herein.

In some embodiments, the ghrelin receptor antagonist is of formula (I): $A_1$-$A_2$-$A_3$-$A_4$-$A_5$-$A_6$, wherein: $A_1$ is His, Tyr, desamino-Tyr, D- or L-Ala, β-Ala, CyclohexylAla (Cyclohexylalanine), D-Arg, Ava (aminovaleric acid), Gly, <Glu (pyroglutaminic acid), α-Aib (alpha-aminoisobutyric acid), γ-Abu (gamma-aminobutyric acid), α-Abu, α,γ-Abu, D-Val, D-phe, D-Thr, D-Pal (pyridylalanine), D-Lys, AcD-Lys, D-Leu, D-Trp, D,α-naphthylalanine, D,β-naphthylalanine, or Ac-D,β-naphthylalanine; $A_2$ is D-α-naphthylalanine, D-β-naphthylalanine; Ac-D-β-naphthylalanine, D- or L-Trp, D- or L-Phe, Ala, His, PicLys (N$^\epsilon$-picoloyl-lysine), D-Cyclohexylalanine, or an amino acid that is methylated at the terminal nitrogen of the α carbon atom of the $A_2$ residue; $A_3$ is D- or L-Lys, lysine analogs and derivatives, Arg, arginine analogs and derivatives, Orn, Phe, Trp, Leu, Pro, Ala, Ser, Pal, or α,γ-Abu; $A_4$ is D- or L-Trp, D- or L-Phe, Ala, Ser, Tyr, Met, Pro, Thr, ILys, or CyclohexylAla; $A_5$ is D- or L-Trp, D- or L-Phe, Ala, Lys, Arg, Orn, Thr, Leu, or D-CyclohexylAla; $A_6$ is Lys, Arg, Orn, D- or L-Phe, Pro(cyclic Arg-Pro), Nle (norleucine), α,γ-Abu amide, or a free acid carboxyl group; and prodrugs, metabolite, or pharmaceutically acceptable salts thereof.

In some embodiments of compounds of formula (I), there can be a normal or reduced psi peptide linkage at position 1. Reduced psi-peptide linkage refers to the peptide linkage (—C(O)NH—) that has been replace by —CH$_2$NH—; therefore, reduced psi peptide linkage at position 1 means the —C(O)NH— bond between first and second amino acid is replaced by —CH$_2$NH—. A reduced psi peptide linkage is indicated as ψ[CH$_2$NH] herein.

In some embodiments, the $A_1$ is methylated at the terminal nitrogen of the alpha carbon atom of the $A_1$ residue.

In some embodiments, the $A_2$ has an extended aromatic chain. Exemplary $A_2$ with extended aromatic chains include, but are not limited to, D-4-halo-Phe, D-4-pyrolidylalanine, and homologues or analogues thereof.

In some embodiments, the ghrelin receptor antagonist of formula (I) is His-DβNal-DLys-Trp-DPhe-Lys-NH$_2$ (SEQ ID NO: 26) or analogues, prodrug, metabolite, or pharmaceutical salts thereof. In another embodiment, the ghrelin receptor antagonist of formula (I) excludes His-DβNal-DLys-Trp-DPhe-Lys-NH$_2$ (SEQ ID NO: 26).

In another embodiment, the ghrelin receptor antagonist of formula (I) is His-DTrp-DLys-Trp-DPhe-Lys-NH$_2$ (SEQ ID NO: 16)

In some embodiments, the ghrelin receptor antagonist is of formula (II): $A_7$-$A_8$-$A_9$-$A_{10}$, wherein: $A_7$ is D-α-Nal, D-β-Nal, Ac-D-β-Nal, Ac-D-α-Nal, D- or L-Tyr, Ac-D-Tyr, Lys, D-Phe, His, α-Abu, α,γ-Abu, γ-Abu, DcyclohexylAla, or isonipecotic carboxylic acid (inip); $A_8$ is D- or L-Trp, Ala, His, Phe, or Leu; $A_9$ is D- or L-Trp, Ala, CyclohexylAla, Phe, Pro, Lys, Sarcosine (Sar, N-methylglycine), or a free acid carboxyl group; $A_{10}$ is D- or L-Arg, Phe, CyclohexylAla, Lys, Ser, NMePhe, DPal, Aib, or Orn; and prodrugs, metabolite, or pharmaceutically acceptable salts thereof.

In some embodiments, the ghrelin receptor antagonist of formula (II) is α,γAbu-DTrp-DTrp-Ser-NH$_2$ (SEQ ID NO: 44), α,γAbu-DTrp-DTrp-Lys-NH$_2$ (SEQ ID NO: 45), α,γAbu-DTrp-DTrp-Orn-NH$_2$ (SEQ ID NO: 46), Tyr-DAla-Phe-Aib-NH$_2$ (SEQ ID NO: 42), Tyr-DAla-Sar-NMePhe-NH$_2$ (SEQ ID NO: 43), Lys-DHis-DTrp-Phe-NH$_2$ (SEQ ID NO: 51), γAbu-DTrp-DTrp-Orn-NH$_2$ (SEQ ID NO: 52), inip-Trp-Trp-Phe-NH$_2$ (SEQ ID NO: 53), Ac-DTrp-Phe-DTrp-Leu-NH$_2$ (SEQ ID NO: 54), Ac-DTrp-DTrp-Lys-NH$_2$ (SEQ ID NO: 56), or Ac-DβNal-Leu-Pro-NH$_2$ (SEQ ID NO: 58).

In some other embodiments, the ghrelin receptor antagonist of formula (II) is not α,γAbu-DTrp-DTrp-Ser-NH$_2$ (SEQ ID NO: 44); α,γAbu-DTrp-DTrp-Lys-NH (SEQ ID NO: 45); or α,γAbu-DTrp-DTrp-Orn-NH$_2$ (SEQ ID NO: 46).

In some embodiments, the ghrelin receptor antagonist is of formula (III):

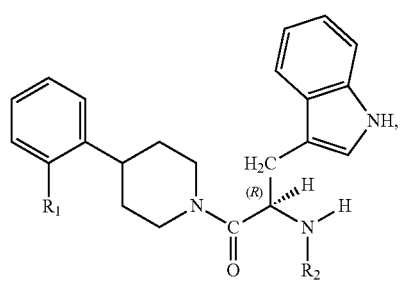

Formula (III)

wherein: $R_1$ is OH; $R_2$ is H, —C(O)—(CH$_2$)$_3$—NH$_2$, —C(O)—C(CH$_3$)$_2$—NH$_2$, —C(O)—CH((CH$_2$)$_4$—NHR$_5$)—NH—C(O)—CH(NHR$_3$)CH$_2$OR$_4$; $R_3$ is H, —C(O)-phenyl, or —C(O)CH$_3$; $R_4$ is H, or —CH$_2$-phenyl; $R_5$ is H, or —C(O)CH$_3$; and isomers, derivatives, prodrugs, metabolite, or pharmaceutically acceptable salts thereof.

Exemplary compounds of formula (III) include, but are not limited to, (R)-2-amino-3-(1H-indol-3-yl)-1-(4-phenylpiperidin-1-yl)propan-1-one; N—((R)-1-((R)-1-((S)-3-(1H-indol-3-yl)-1-oxo-1-(4-phenylpiperidin-1-yl)propan-2-ylamino)-6-amino-1-oxohexan-2-ylamino)-3-hydroxy-1-oxopropan-2-yl)-benzamide; (S)—N—((S)-3-(1H-indol-3-yl)-1-oxo-1-(4-phenylpiperidin-1-yl)propan-2-yl)-6-acetamido-2-((S)-2-amino-3-(benzyloxy)propanamido)-hexanamide; (S)—N—((R)-3-(1H-indol-3-yl)-1-oxo-1-(4-phenylpiperidin-1-yl)propan-2-yl)-2-((S)-2-acetamido-3-(benzyloxy)propanamido)-6-aminohexanamide; (R)—N-(3-(1H-indol-3-yl)-1-(4-(2-methoxyphenyl)piperidin-1-yl)-1-oxopropan-2-yl)-4-aminobutanamide; (R)-2-amino-N-(3-(benzyloxy)-1-oxo-1-(4-phenylpiperazin-1-yl)propan-2-yl)-2-methylpropanamide; and isomers and derivatives thereof.

In some embodiments, the ghrelin receptor antagonist is of formula (IV):

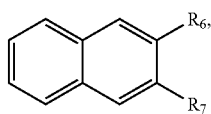

Formula (IV)

wherein: $R_6$ is —C(O)OCH$_2$CH$_3$, —C(O)OCH$_3$,

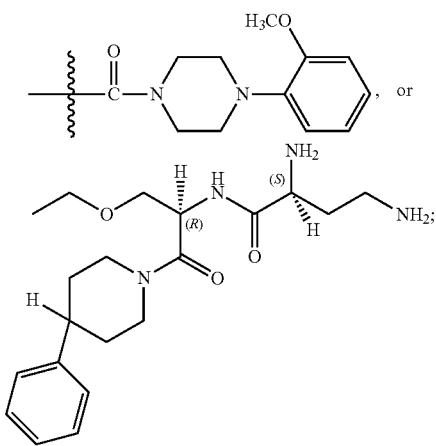

or $R_7$ is —H,

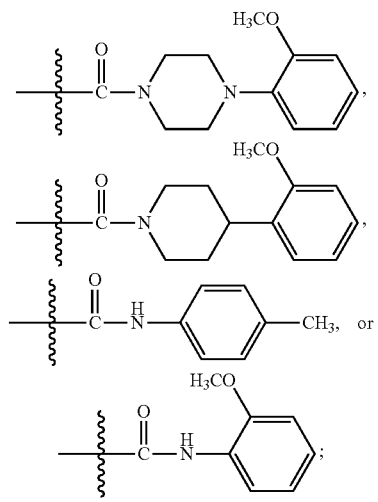

and isomers, derivatives, prodrugs, metabolite, or pharmaceutically acceptable salts thereof.

Exemplary compounds of formula (IV) include, but are not limited to, naphthalene-2,3-diylbis((4-(2-methoxyphenyl) piperazin-1-yl)-methanone); 3-(2-methoxyphenylcarbamoyl)-2-naphthoate; (S)-2,4-diamino-N—((R)-3-(naphthalen-2-ylmethoxy)-1-oxo-1-(4-phenylpiperidin-1-yl)propan-2-yl)-butanamide; ethyl 3-(4-(2-methoxyphenyl)-piperidine-1-carbonyl)-2-naphthoate; methyl 3-(p-tolylcarbamoyl)-2-naphthoate; and isomers and derivatives thereof.

In some embodiments, the ghrelin receptor antagonist is of formula (V):

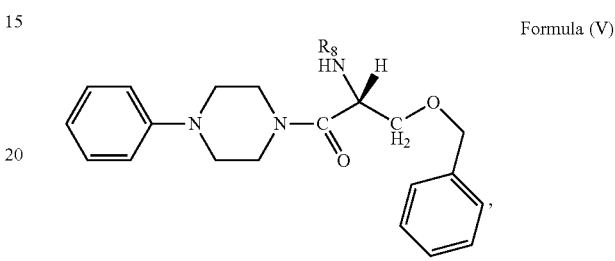

Formula (V)

wherein: $R_8$ is H, or —C(O)C(CH$_3$)$_2$—NH$_2$; and isomers, derivatives, prodrugs, metabolite, or pharmaceutically acceptable salts thereof.

Exemplary compounds of formula (V) include, but are not limited to, (R)-2-amino-N-(3-(benzyloxy)-1-oxo-1-(4-phenylpiperazin-1-yl)propan-2-yl)-2-methylpropanamide; (R)-2-amino-3-(benzyloxy)-1-(4-phenylpiperazin-1-yl)propan-1-one; and isomers and derivatives thereof.

In some embodiments, the ghrelin receptor antagonist is of formula (VI): $S^1B^1S^2B^2S^3$, wherein: $S^1$ is H, CO$_2$H, $R^{11}$, $R^{11}R^{12}$, or $R^{11}R^{12}R^{13}$; is des-Amino, H, CO$_2$H, $R^{11}$, $R^{11}R^{12}$, or $R^{11}R^{12}R^{13}$; $S^3$ is H, CO$_2$H, NH$_2$, $R^{11}$, $R^{11}$, $R^{12}$, or $R^{11}R^{12}R^{13}$; $R^{11}$, $R^{12}$, and $R^{13}$ are independently selected from the group consisting of L-amino acids, Pal (3-pyridyl alanine), cyclo-Ala, Aib, Nle, inip, Abu, βNal, αNal, Orn, carboxylic acid, and their respective D isomers; $B^1$ is selected from the group consisting of Trp, βNal, αNal, Leu, Lys, cyclohexylAla, and their respective D isomers; $B^2$ is any natural L-amino acid, Pal (3-pyridyl alanine), cycloAla, Aib, Nle, inip, Abu, βNal, αNal, Orn, and their respective D isomers; and isomers, derivatives, prodrugs, metabolite, or pharmaceutically acceptable salts thereof.

The compounds of formulae (I)-(VI) are described in the U.S. Provisional Patent App. No. 60/795,960, filed Apr. 28, 2007 and Int. Pat. App. Pub. No.: PCT/US2007/010389, contents of both of which are herein incorporated by reference.

In some embodiments, the ghrelin receptor antagonist is a peptide comprising the amino acid sequence of formula (VII): $A^{11}$-$A^{12}$-$A^{13}$-Gly-Ser-$A^{14}$-Phe-Leu-$A^{15}$-$A^{16}$-$A^{17}$-$A^{18}$ (SEQ ID NO: 93), wherein each of $A^{11}$, $A^{12}$, and $A^{13}$, is absent, an amino acid, or an amino protecting group; $A^{15}$, $A^{16}$, $A^{17}$, and $A^{18}$ is independently absent or an amino acid; $A^{14}$ is a serine conjugated with a —C(O)C$_1$-C$_{20}$alky group on the side chain OH of said serine or a diaminopropionic acid conjugated with a —C(O)C$_1$-C$_{20}$alky group on one of the amino group diaminopropionic acid, provided at least one of $A^{11}$, $A^{12}$, or $A^{13}$ is present.

In some embodiments, each of $A^{11}$, $A^{12}$, $A^{13}$, $A^{15}$; $A^{16}$, $A^{17}$, and $A^{18}$ is independently selected from the group consisting of alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, valine, homocysteine, phosphoserine, phosphothreonine, phosphotyrosine, hydroxyproline, gamma-carboxyglutamate; hippuric acid, octahydroindole-2-carboxylic acid, statine, 1,2,3,4,-tetrahydroisoquinoline-3-carboxylic acid, penicillamine (3-mercapto-D-valine), ornithine, citruline, alpha-methylalanine, para-benzoylphenylalanine, para-aminophenylalanine, p-fluorophenylalanine, phenylglycine, propargylglycine, sarcosine, and tert-butylglycine), diaminobutyric acid, 7-hydroxy-tetrahydroisoquinoline carboxylic acid, naphthylalanine, biphenylalanine, cyclohexylalanine, amino-isobutyric acid, norvaline, norleucine, tert-leucine, tetrahydroisoquinoline carboxylic acid, pipecolic acid, phenylglycine, homophenylalanine, cyclohexylglycine, dehydroleucine, 2,2-diethylglycine, 1-amino-1-cyclopentanecarboxylic acid, 1-amino-1-cyclohexanecarboxylic acid, amino-benzoic acid, amino-naphthoic acid, gamma-aminobutyric acid, difluorophenylalanine, nipecotic acid, alpha-amino butyric acid, thienyl-alanine, t-butylglycine, desamino-Tyr, aminovaleric acid, pyroglutaminic acid, alpha-aminoisobutyric acid, gamma-aminobutyric acid, alpha-aminobutyric acid, alpha, gamma-aminobutyric acid, pyridylalanine, α-naphthylalanine, β-naphthylalanine, Ac-β-naphthylalanine, N$^ε$-picoloyl-lysine, 4-halo-Phenyl, 4-pyrolidylalanine, isonipecotic acid, and isomers, analogs and derivatives thereof. One of skill in the art would know that this definition includes, D- and L-amino acids, alpha- and beta-amino acids, chemically modified amino acids, naturally occurring non-proteogenic amino acids, rare amino acids, and chemically synthesized compounds that have properties known in the art to be characteristic of an amino acid. Furthermore, as used herein, the term "amino acid" includes compounds which depart from the structure of the naturally occurring amino acids, but which have substantially the structure of an amino acid, such that they can be substituted within a peptide which retains is activity, e.g., biological activity. Thus, for example, in some embodiments amino acids can also include amino acids having side chain modifications or substitutions, and also include related organic acids, amides or the like. Without limitation, an amino acid can be a proteogenic or non-proteogenic amino acid. As used herein, the term "proteogenic" indicates that the amino acid can be incorporated into a protein in a cell through well-known metabolic pathways.

The term "alkyl" refers to saturated non-aromatic hydrocarbon chains that may be a straight chain or branched chain, containing the indicated number of carbon atoms (these include without limitation propyl, allyl, or propargyl), which may be optionally inserted with N, O, or S. For example, $C_1$-$C_6$ indicates that the group may have from 1 to 6 (inclusive) carbon atoms in it. As used herein, the alkyl can also comprise 1, 2, or 3 double and/or triple bonds.

Exemplary amino-protecting groups include, but are not limited to, carbamate protecting groups, such as 2-trimethylsilylethoxycarbonyl (Teoc), 1-methyl-1-(4-biphenylyl) ethoxycarbonyl (Bpoc), t-butoxycarbonyl (BOC), allyloxycarbonyl (Alloc), 9-fluorenylmethyloxycarbonyl (Fmoc), and benzyloxycarbonyl (Cbz); amide protecting groups, such as formyl, acetyl, trihaloacetyl, benzoyl, and nitrophenylacetyl; sulfonamide protecting groups, such as 2-nitrobenzenesulfonyl; and imine and cyclic imide protecting groups, such as phthalimido and dithiasuccinoyl. Further amino protecting groups, as well as other representative protecting groups, are disclosed in Greene and Wuts, *Protective Groups in Organic Synthesis*, Chapter 2, 2d ed., John Wiley & Sons, New York, 1991, and *Oligonucleotides And Analogues A Practical Approach*, Ekstein, F. Ed., IRL Press, N.Y, 1991.

In some embodiments of compounds of formula (VII), the alkyl is a $C_1$-$C_{16}$alkyl.

In some embodiments of compounds of formula (VII), the alkyl is methyl, ethyl, butyl, pentyl, hexyl, heptyl, octyl, nonyl, decyl, undecyl, or dodecyl.

Without wishing to be bound by theory, addition of at least one of $A^{11}$, $A^{12}$, or $A^{13}$ on the N-terminus of the peptides of formula (VII) block the N-terminal glycine of the ghrelin pentapeptide which is necessary for ghrelin activity.

In some embodiments, $A^5$ is octanoylated serine. In some embodiments, $A^5$ is an octyanolyatd diaminopropionic acid. In some embodiments, $A^5$ is not palmitolyted diaminopropionic acid, i.e., a diaminopropionic acid conjugated with —C(O)$C_{17}$-alkyl on one of the amino groups of the diaminopropionic acid.

In some embodiments, the peptide of formula (VII) comprises at least one (e.g., 1, 2, 3, 4, 5, 6, 7, 8, 9, 10 or more) D-amino acid. In some embodiments, at least one (e.g., 1, 2, 3, 4, 5, 6, or 7) of $A^{11}$, $A^{12}$, $A^{13}$, $A^{15}$, $A^{16}$, $A^{17}$, and $A^{18}$ is a D-amino acid or derivative thereof. The D-amino acid can be present at any position in the peptide of formula (VII), for example reading from the N-terminal at position 1, 2, 3, 4, 5, 6, 7, 8, 9, 10, 11, or 12. When more than one D-amino acids are present, they can be positioned next to or not next to each other.

In some embodiments, the peptide of formula (VII) comprises at least one beta-amino acid. In some embodiments, at least one (e.g., 1, 2, 3, 4, 5, 6, or 7) of $A^{11}$, $A_{12}$, $A^{13}$, $A^{15}$, $A^{16}$, $A^{17}$, and $A^{18}$ is a beta-amino acid. The beta-amino acid can be present at any position in the peptide of formula (VII), for example reading from the N-terminal at position 1, 2, 3, 4, 5, 6, 7, 8, 9, 10, 11, or 12. When more than one beta-amino acids are present, they can be positioned next to or not next to each other.

In some embodiments, the peptide of formula (VII) comprises at least one (e.g., 1, 2, 3, 4, 5, 6, 7, 8, 9, 10, or 11) peptide bond replaced by a linkage selected from the group consisting of reduced psi peptide bond, urea, thiourea, carbamate, sulfonyl urea, trifluoroethylamine, ortho-(aminoalkyl)-phenylacetic acid, para-(aminoalkyl)-phenylacetic acid, meta-(aminoalkyl)-phenylacetic acid, thioamide, tetrazole, boronic ester, and olefinic group. The peptide replacement linkage can be present at any position in the peptide of formula (VII), for example reading from the N-terminal at position 1, 2, 3, 4, 5, 6, 7, 8, 9, 10, or 11. When more than peptide replacement linkages are present, they can be positioned next to (e.g., on both sides of a given amino acid) or not next to each other (e.g., only one side of a given amino acid is linked via a peptide replacement linkage to the next amino acid).

In some embodiments, the peptide of formula (VII) is Gly-Met-Ala-Gly-Ser-(Dap-Oct)-Phe-Leu-Ser-Pro-Glu-His-NH$_2$ (SEQ ID NO: 3).

In some embodiments, the peptide of formula (VII) is Gly-Met-Ala-Gly-Ser-(Dap-Palmityl)-Phe-Leu-Ser-Pro-Glu-His-NH$_2$ (SEQ ID NO: 4).

In some embodiments, the peptide of formula (VII) is not Gly-Met-Ala-Gly-Ser-(Dap-Palmityl)-Phe-Leu-Ser-Pro-Glu-His-NH$_2$ (SEQ ID NO: 4).

Without wishing to be bound by theory, the ghrelin receptor antagonist can be a dipeptide, a tripeptide, and/or a tetrapeptide. Examples of such peptides include, but are not limited to, the following embodiments.

In some embodiments, the ghrelin receptor antagonist comprises a tetrapeptide core of DTrp-Ala-Trp-DPhe. In some embodiments of this, the position 1 of the tetrapeptide core comprise an amino acid selected from the group consisting of D-Trp, D-β-Nal, D-α-Nal, D-Phe, and D-cyclohexylAla, while the position 2 of the tetrapeptide core comprise L- or D-natural, unnatural, or derivatized amino acid residues including, but not limited to, D-Lys, D-Orn, Ser, D-Pal, D-Leu, and Phe. In some embodiments, the tetrapeptide core comprises 1, 2, 3, 4, or 5 additional amino acids at the N-terminus, C-terminus, or both the N- and C-termini of the tetrapeptide core. Without limitation, the N-terminus additions may comprise any of L- or D-amino acids, such as, but not limited to, Tyr, His, desamino Tyr, GlΨ, AlaΨ, D-Ala, β-Ala, α-Abu, γ-Abu, αγ-Abu, D-Lys, <Glu, D-Arg, D-Orn, carboxylic acid, or mono, di tripeptides or longer peptides such as His-Lys, His-DLys, and DHis-Lys. Without limitation, the C-terminus additions may comprise of any L- or D-natural or unnatural amino acid residues with terminal amidation or carboxylation including mono, di, tripeptides or longer peptides such as Lys, Arg, Lys-Gln, and Lys-Gln-Gly. Examples of tetrapeptide core containing antagonist are DHis-DTrp-DPro-DIleNH$_2$ (SEQ ID NO: 90), DHis-DTrp-DPro-DArgNH$_2$ (SEQ ID NO: 91), and DβNal-DTrp-DPro-DArgNH$_2$ (SEQ ID NO: 92).

In some embodiments, the ghrelin receptor antagonist comprises a tripeptide core of DAla-DTrp-Phe. The positions 1 and 2 of this tripeptide core can be substituted with any amino acids selected from D-amino acid residues or unnatural amino acid residues. The residue at position 3 can be substituted with an amino acid selected from the group consisting of Trp, Leu, Val, Ile, Pro, Phe, cyclohexylAla and cyclopentylAla. In some embodiments, the tetrapeptide core comprises 1, 2, 3, 4, or 5 additional amino acids at the N-terminus, C-terminus, or both the N- and C-termini of the tripeptide core. Without limitation, the N terminus additions can comprise any L- or D-natural, unnatural amino acid residue, organic carboxylic acids, or dipeptides or longer peptides with L- or D-natural or unnatural amino acid residues in various combinations and/or sequences. Some exemplary N-terminus additions include, but are not limited to, DAla-DβNal, DAla-DαNal, βAla-Trp, His-Trp, DHis-Trp, DHis-DTrp, His-DTrp. Similarly, the C terminus additions can comprise, without limitation, any L- or D-natural or unnatural amino acid residues with terminal amidation or carboxylation including. Exemplary C-terminus additions include, but are not limited to, mono, di, tripeptides, or longer peptides such as Lys, Arg, Lys-Gln, Lys-Gln-Gly or carboxylic acid. Examples of tripeptide core containing antagonist are αAib-DTrp-cyclohexylDAlaNH$_2$ (SEQ ID NO: 69), AcDTrp-DTrpLysNH$_2$ (SEQ ID NO: 56) and AcDβNal-Leu-ProNH$_2$ (SEQ ID NO: 58).

In some embodiments, the ghrelin receptor antagonist comprises the tripeptide core of DTrp-Phe-DTrp. The positions 1 and 3 of this core may be substituted with amino acids selected from DβNal, DαNal, DPhe, and DcyclohexylAla, and the position 2 of the tripeptide core may be substituted with amino acids selected from Trp βNal, αNal, Leu, DLeu, and DLys. In one embodiment, there may be additional amino acids at the N-terminus alone, C-terminus alone, or at both N- and C-terminus of the tripeptide core. N terminus additions may comprise a L or D natural or unnatural amino acid residues or organic carboxylic acid. N terminus additions may comprise a dipeptides, tripeptide, or tetrapeptides comprising L or D natural or unnatural amino acid residues in various combinations and/or sequences, for example DAla-DβNal, DAla-DαNal, βAla-Trp, His-Trp, DHis-Trp, DHis-DTrp, His-DTrp. C terminus additions may comprise an amino acid residue selected from Leu, Lys, and Arg. C terminus additions may also comprise a dipeptide or tripeptide comprising the amino acids Leu, Lys, Arg, and combinations thereof. Examples of C terminus additions are Leu, Leu-Leu, Leu-Lys, Leu-Arg, Leu-Leu-Lys.

In yet another embodiment, the ghrelin receptor antagonist has at least a dipeptide core of DTrp-DTrp wherein the core amino acids may be substituted with D natural and/or derivatized amino acid residues of Trp, βNal, αNal, Phe, and various combinations thereof. In one embodiment, there may be additional amino acids at the N-terminus alone, C-terminus alone, or at both the N- and C-terminus of the dipeptide core. N terminus additions may comprise L or D natural or derivatized amino acid residues and/or organic carboxylic acid. Additionally, N terminus additions may also comprise a dipeptide or tripeptide or tetrapeptide or pentapeptide comprising amino aicd residues selected from Tyr, His, desamino Tyr, Lys, Glyψ, Alaψ, DAla, αγAbu, αAbu, γAbu, Lys, DLys, isonipecotic carboxylic acid (inip), βAla, DAla, DLys, DThr, DVal, DLeu, cyclohexylAla, cyclopentylAla, DTrp, iPrLys, and diethyl guanidinoArg. Examples of N-terminus additions include His-Trp, DLys-Tyr, βAla-Trp, N-AcDLys-Tyr, βAla-Pal, αγAbu-Trp, γAbu-Trp, Ava-Trp, αAbu-Trp, His-DLys, Lys-DHis, DLys-Tyr-DHis. C terminus additions may comprise L- or D-natural or derivatized amino acid residues or organic carboxylic acids. C terminus additions may also comprise a dipeptide or tripeptide or tetrapeptide or pentapeptide comprising amino acids residues selected from Phe, DPro, Leu, Met, Ser, Lys, Orn, Arg, cyclohexylAla, and cyclopentylAla. examples of the C-terminus additions are Phe-Lys, DPro-Lys, Phe-DPro-Lys, DPro-Arg, Phe-Met, Phe-Ala, Phe-Ser. Examples of dipeptide core containing antagonist are AcDβNal-DTrpNH$_2$ (SEQ ID NO: 68) and DThr-DαNal-DTrp-DPro-ArgNH$_2$ (SEQ ID NO: 48).

In some embodiments, the ghrelin receptor antagonist and/or growth hormone secretatogue antagonist in any of the methods described herein comprises a compound having a formula I, II, III, IV, V, or VI described herein. In other embodiments, the ghrelin receptor antagonist and/or growth hormone secretatogue antagonist in any of the methods described herein comprises analogues, prodrug, metabolite, or pharmaceutical salts thereof of formula I, II, III, IV, V, or VI.

In one embodiment, the ghrelin receptor antagonist is His-DβNalDLysTrpDPheLysNH$_2$ (SEQ ID NO: 26), or analogues, prodrug, metabolite, or pharmaceutical salts thereof.

In one embodiment, the ghrelin receptor antagonist is His-DTrpDLysTrpDPheLys NH$_2$ (SEQ ID NO: 16).

In another embodiment, the compounds of the formula (I), excludes HisDβNalDLysTrpDPheLysNH$_2$ (SEQ ID NO: 26).

In one embodiment, D-Arg1,D-Phe5,D-Trp-7,9,Leu11 substance P functions as a low-potency antagonist but a high-potency full inverse agonist on the ghrelin receptor.

In some embodiments, the ghrelin receptor antagonists described herein, either alone or in combination with a GOAT inhibitor, inhibit GH secretion in a subject. The GH secretion can be inhibited by at least 5%, at least 10%, at least 20%, at least 30%, at least 40%, at least 50%, at least 60%, at least 70%, at least 80%, at least 90%, at least 95% or complete inhibition relative to an untreated control. Skilled artisan is well aware of the methods for measuring GH secretion in vivo, for example the methods described in the Examples section.

In some embodiments, the ghrelin receptor antagonists described herein, either alone or in combination with a GOAT inhibitor, decrease or inhibit food intake in a subject by at least 5%, at least 10%, at least 20%, at least 30%, at least 40%, at least 50%, at least 60%, at least 70%, at least 80%, at least 90%, at least 95% or complete inhibition relative to an untreated control. As used herein, food intake refers to caloric intake by a subject. In some cases, food intake also refers to weight of food consumed by a subject.

In one embodiment, the ghrelin receptor antagonist and/or growth hormone secretatogue antagonist in any of the methods described herein comprises compositions of compounds having formulae I, II, III, IV, V, VI, VII, or combinations thereof. For example, compositions of compounds having formulae I, II, III, IV, V, VI, VII, or combinations thereof are used for the treatment of obesity or obesity related diseases and disorders in a subject, and can be combined with a surgical or mechanical procedure used to treat obesity or other obesity treatment. Such procedures include but are not limited to gastric bypass surgery and gastric banding.

In one embodiment, the ghrelin receptor antagonist and/or growth hormone secretatogue antagonist in any of the methods described herein consists essentially of compositions of compounds having formulae I, II, III, IV, V, VI, VII, or combinations thereof.

In one embodiment, the ghrelin receptor antagonist and/or growth hormone secretatogue antagonist in any of the methods described herein consists of compositions of compounds having formulae I, II, III, IV, V, VI, VII, or combinations thereof.

In one embodiment, compositions of compounds having formulae I, II, III, IV, V, VI, VII, or combinations thereof can be used in combination for the treatment of various diseases and disorders described herein, e.g. cancer treatment, obesity treatment, metabolic syndrome and diabetes treatment. These treatments are well known to physicians skilled in the art.

The experimental data regarding the effect of the compounds of this invention has been produced in well known animal models that are typically used for the effects of anti-obesity treatments at the first stage and are thus likely to be applicable to human obesity.

In some embodiments, the individual is obese or overweight. Typically, an overweigh individual is considered to have a body mass index (BMI) of over 25 but under 30 and an obese individual is considered to have a BMI of over 30.

In one embodiment, the methods and uses of the present invention are applicable for both sexes and all age groups including children and teenagers.

In some embodiments, the GOAT inhibitor and/or ghrelin receptor antagonist described herein are administered to a subject in need of such treatment for any of the disease or disorders or associated disorders discussed and described herein, e.g. obesity, overeating, diabetes mellitus, metabolic syndrome, hypertension, elevated plasma insulin concentrations, insulin resistance, dyslipidemias, and hyperlipidemia, unregulated cellular proliferation, and cancer such as hormonally functional endocrine or non-endocrine tumors, breast and prostate cancer, ectopic neuroendocrine tumors, carcinoid and pancreatic tumors, and prostate cancer, osteoblast cancer, pancreatic cancer, adenocarcinomas and hepatoma. In one embodiment, a subject who is in need of treatment is one who has been clinically diagnosed with a disease, disorders or associated disorders described herein by methods well known to one skilled in the art, e.g. a physician. In another embodiment, a subject who is in need of treatment is one who is at risk of developing the disease, disorders or associated disorders described herein. For example, a subject who has had a sudden gain of weight in a short period of time, e.g. gaining 5 kilograms, 10 kilograms, 20 kilograms, 30 kilograms, 40 kilograms, or 50 kilogram within a period of 1 month, 2 months, 3 months, or four months. Without wishing to be bound by theorym, such a subject is at high risk for developing diabetes mellitus, metabolic syndrome, hypertension, elevated plasma insulin concentrations, insulin resistance, dyslipidemias, and hyperlipidemia and other obesity related disorders.

As used herein, a "subject" means a human or animal. Usually the animal is a vertebrate such as a primate, rodent, domestic animal or game animal. Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. Patient or subject includes any subset of the foregoing, e.g., all of the above, but excluding one or more groups or species such as humans, primates or rodents. In certain embodiments, the subject is a mammal, e.g., a primate, e.g., a human. The terms, "patient" and "subject" are used interchangeably herein.

In some embodiments of the methods described herein, the method further comprising selecting a subject identified as being in need of treatment by a GOAT inhibitor and a ghrelin antagonit. A subject suffering from a disease or disorder can be selected based on the symptoms presented as described herein.

In some embodiments, the subject is a mammal. In other embodiments, the subject is an animal, e.g. a cat, a dog, a horse. In one preferred embodiment, the subject is a human.

Definitions

Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. The definitions are provided to aid in describing particular embodiments, and are not intended to limit the claimed invention, because the scope of the invention is limited only by the claims. Further, unless otherwise required by context, singular terms shall include pluralities and plural terms shall include the singular.

As used herein the term "comprising" or "comprises" is used in reference to compositions, methods, and respective component(s) thereof, that are essential to the invention, yet open to the inclusion of unspecified elements, whether essential or not.

As used herein the term "consisting essentially of" refers to those elements required for a given embodiment. The term permits the presence of additional elements that do not materially affect the basic and novel or functional characteristic(s) of that embodiment of the invention.

The term "consisting of" refers to compositions, methods, and respective components thereof as described herein, which are exclusive of any element not recited in that description of the embodiment.

The singular terms "a," "an," and "the" include plural referents unless context clearly indicates otherwise. Similarly, the word "or" is intended to include "and" unless the context clearly indicates otherwise.

Although methods and materials similar or equivalent to those described herein can be used in the practice or testing of this disclosure, suitable methods and materials are described below. The term "comprises" means "includes." The abbreviation, "e.g." is derived from the Latin exempli gratia, and is used herein to indicate a non-limiting example. Thus, the abbreviation "e.g." is synonymous with the term "for example."

The terms "decrease", "reduced", "reduction", "decrease" or "inhibit" are all used herein generally to mean a decrease by a statistically significant amount. However, for avoidance of doubt, ""reduced", "reduction" or "decrease" or "inhibit" means a decrease by at least 10% as compared to a reference level, for example a decrease by at least about 20%, or at least about 30%, or at least about 40%, or at least about 50%, or at least about 60%, or at least about 70%, or at least about 80%, or at least about 90% or up to and including a 100% decrease (e.g. absent level as compared to a reference sample), or any decrease between 10-100% as compared to a reference level.

The terms "increased", "increase" or "enhance" or "activate" are all used herein to generally mean an increase by a statically significant amount; for the avoidance of any doubt, the terms "increased", "increase" or "enhance" or "activate" means an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level.

The term "statistically significant" or "significantly" refers to statistical significance and generally means a two standard deviation (2SD) below normal, or lower, concentration of the marker. The term refers to statistical evidence that there is a difference. It is defined as the probability of making a decision to reject the null hypothesis when the null hypothesis is actually true. The decision is often made us Unless otherwise noted, the abbreviations for the residues of amino acids used herein are in agreement with the standard nomenclature; and are as follows: Gly: Glycine; Tyr: Tyrosine; Ile: Isoleucine; Glu: Glutamic Acid; Thr: Threonine; Phe: Phenylalanine; Ala: Alanine; Lys: Lysine; Asp: Aspartic Acid; Cys: Cysteine; Arg: Arginine; Gln: Glutamine; Pro: Proline; Leu: Leucine; Met: Methionine; Ser: Serine; Asn: Asparagine; His: Histidine; Trp: Tryptophan; Val: Valine; Orn: Ornithine; Desamino-Tyr: Desamino Tyrosine; Desamino-His: Desamino Histidine; Desamino-alpha-Aib: Desamino-alpha-aminoisobutyric acid; Desamino-alpha-Abu: Desamin-alpha-aminobutyric acid; Desamino-alpha-gamma-Abu (Desamino-α,γ-Abu): Desamino-alpha-gamma-aminobutyric acid.

Moreover, all of the three letter-abbreviations of the amino acids preceded by a "D" indicates the dextro-isomer of the amino acid residue. Glycine is considered to be included in the term naturally occurring L-amino acids. Other abbreviations used herein include: Aib: aminoisobutyric acid; inip: isonipecotyl; Abu—aminobutyric acid; alpha-Nal: alpha-naphthylalanine; beta-Na: beta-naphthylalanine; D-alpha Nal: alpha-naphthyl-D-alanine; D-beta-Nal: beta-naphthyl-D-alanine; Pal: 3-pyridyl alanine; CHx: cyclohexyl; CHxAla: L-cyclohexylalanine; Ava: Aminovaleric acid; IMA: N-alpha-imidazole acetic acid; imc: imidazole carboxylic acid; beta-Ala: beta-Alanine; ILys: Lysine (iPr) which is isopropyl-α-N$^\epsilon$lysine; α,γ-Abu: alpha-gamma-diaminobutyric acid; Nle: norleucine; PicLys: N$^\epsilon$-picoloyl-lysine); inip: isonipecotoc carboxylic acid; NMePhe: N-methylated phenylalanine; Sar: sarcosine (N-methylglycine); <Glu: pyroglutamic acid; Ac-D-β-Nal: acetylated D-beta-naphthylalanine; Ac-D-α-Nal: acetylated D-alpha-naphthylalanine; and N-Ac-D-beta-Nal: N-acetyl D-β-Naphthylalanine.

The terms "administration of" and or "administering" a compound should be understood to mean providing a ghrelin receptor antagonist compound of the invention, a prodrug or an active metabolite of a compound of the invention to a subject in need of treatment. As such, the term "administer" refers to the placement of a composition into a subject by a method or route which results in at least partial localization of the composition at a desired site such that GOAT is inhibited and/or ghrelin receptor is antagonized. Compounds described herein can be administered by any appropriate route known in the art including, but not limited to oral or parenteral routes, including intravenous, intramuscular, subcutaneous, transdermal, airway (aerosol), pulmonary, nasal, rectal, and topical (including buccal and sublingual) administration.

Exemplary modes of administration include, but are not limited to, injection, infusion, instillation, inhalation, or ingestion. "Injection" includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebro spinal, and intrasternal injection and infusion. In preferred embodiments, the compositions are administered by intravenous infusion or injection.

The term "ghrelin receptor" as used herein includes growth hormone secretagogue receptor, GHS-R1a and subtypes, isoforms and variants thereof.

The term "diabetes," as used herein, includes both insulin-dependent diabetes mellitus (i.e., IDDM, also known as type I diabetes) and non-insulin-dependent diabetes mellitus (i.e., NIDDM, also known as Type II diabetes). Type I diabetes, or insulin-dependent diabetes, is the result of an absolute deficiency of insulin, the hormone which regulates glucose utilization. Type II diabetes, or insulin-independent diabetes (i.e., non-insulin-dependent diabetes mellitus), often occurs in the face of normal, or even elevated levels of insulin and appears to be the result of the inability of tissues to respond appropriately to insulin. Most of the Type II diabetics are also obese. The compositions of the present invention are useful for treating both Type I and Type II diabetes. The compositions are especially effective for treating Type II diabetes. The compounds or combinations of the present invention are also useful for treating and/or preventing gestational diabetes mellitus.

There are two forms of Diabetes mellitus: (1) insulin dependent or Type 1 Diabetes (a.k.a., Juvenile Diabetes, Brittle Diabetes, Insulin Dependent Diabetes Mellitus (IDDM)) and (2) non-insulin-dependent or Type II Diabetes (a.k.a., NIDDM). Type 1 Diabetes develops most often in young people but can appear in adults. Type 2 Diabetes develops most often in middle aged and older adults, but can appear in young people. Diabetes is a disease derived from multiple causative factors and characterized by elevated levels of plasma glucose (hyperglycemia) in the fasting state or after administration of glucose during an oral glucose tolerance test. A decrease in β-cell mass occurs in both Type 1 and Type 2 Diabetes.

The terms "diabetes" and "diabetes mellitus" are used interchangeably herein. The World Health Organization defines the diagnostic value of fasting plasma glucose concentration to 7.0 mmol/l (126 mg/dl) and above for Diabetes Mellitus (whole blood 6.1 mmol/l or 110 mg/dl), or 2-hour glucose level 11.1 mmol/L (≥200 mg/dL). Other values suggestive of or indicating high risk for Diabetes Mellitus include elevated arterial pressure 140/90 mm Hg; elevated plasma triglycerides (≥1.7 mmol/L; 150 mg/dL) and/or low HDL-cholesterol (<0.9 mmol/L, 35 mg/dl for men; <1.0 mmol/L, 39 mg/dL women); central obesity (males: waist to hip ratio >0.90; females: waist to hip ratio >0.85) and/or body mass index exceeding 30 kg/m², microalbuminuria, where the urinary albumin excretion rate ≥20 μg/min or albumin:creatinine ratio ≥30 mg/g).

A "pre-diabetic condition" refers to a metabolic state that is intermediate between normal glucose homeostasis, metabolism, and states seen in Diabetes Mellitus. Pre-diabetic conditions include, without limitation, Metabolic Syndrome ("Syndrome X"), Impaired Glucose Tolerance (IGT), and Impaired Fasting Glycemia (IFG). IGT refers to post-prandial abnormalities of glucose regulation, while IFG refers to abnormalities that are measured in a fasting state. The World Health Organization defines values for IFG as a fasting plasma glucose concentration of 6.1 mmol/L (100 mg/dL) or greater (whole blood 5.6 mmol/L; 100 mg/dL), but less than 7.0 mmol/L (126 mg/dL) (whole blood 6.1 mmol/L; 110 mg/dL). Metabolic Syndrome according to National Cholesterol Education Program (NCEP) criteria are defined as having at least three of the following: blood pressure ≥130/85 mm Hg; fasting plasma glucose ≥6.1 mmol/L; waist circumference >102 cm (men) or >88 cm (women); triglycerides ≥1.7 mmol/L; and HDL cholesterol <1.0 mmol/L (men) or 1.3 mmol/L (women).

"Impaired glucose tolerance" (IGT) is defined as having a blood glucose level that is higher than normal, but not high enough to be classified as Diabetes Mellitus. A subject with IGT will have two-hour glucose levels of 140 to 199 mg/dL (7.8 to 11.0 mmol) on the 75 g oral glucose tolerance test. These glucose levels are above normal but below the level that is diagnostic for Diabetes. Subjects with impaired glucose tolerance or impaired fasting glucose have a significant risk of developing Diabetes and thus are an important target group for primary prevention.

"Normal glucose levels" is used interchangeably with the term "normoglycemic" and refers to a fasting venous plasma glucose concentration of less than 6.1 mmol/L (110 mg/dL). Although this amount is arbitrary, such values have been observed in subjects with proven normal glucose tolerance, although some may have IGT as measured by oral glucose tolerance test (OGTT). A baseline value, index value, or reference value in the context of the present invention and defined herein can comprise, for example, "normal glucose levels."

In general, treatment of Diabetes is determined by standard medical methods. A goal of Diabetes treatment is to bring sugar levels down to as close to normal as is safely possible. Commonly set goals are 80-120 milligrams per deciliter (mg/dl) before meals and 100-140 mg/dl at bedtime. A particular physician may set different targets for the patent, depending on other factors, such as how often the patient has low blood sugar reactions. Useful medical tests include tests on the patient's blood and urine to determine blood sugar level, tests for glycosylated hemoglobin level (HbA1c; a measure of average blood glucose levels over the past 2-3 months, normal range being 4-6%), tests for cholesterol and fat levels, and tests for urine protein level. Such tests are standard tests known to those of skill in the art (see, for example, American Diabetes Association, 1998). A successful treatment program can also be determined by having fewer patients in the program with complications relating to Diabetes, such as diseases of the eye, kidney disease, or nerve disease.

Type 1 Diabetes is an autoimmune disease that results in destruction of insulin-producing beta cells of the pancreas. Lack of insulin causes an increase of fasting blood glucose (around 70-120 mg/dL in nondiabetic people) that begins to appear in the urine above the renal threshold (about 190-200 mg/dl in most people). Type 1 Diabetes can be diagnosed using a variety of diagnostic tests that include, but are not limited to, the following: (1) glycated hemoglobin (A1C) test, (2) random blood glucose test and/or (3) fasting blood glucose test.

The Glycated hemoglobin (A1C) test is a blood test that reflects the average blood glucose level of a subject over the preceding two to three months. The test measures the percentage of blood glucose attached to hemoglobin, which correlates with blood glucose levels (e.g., the higher the blood glucose levels, the more hemoglobin is glycosylated). An A1C level of 6.5 percent or higher on two separate tests is indicative of Diabetes. A result between 6 and 6.5 percent is considered prediabetic, which indicates a high risk of developing Diabetes.

The Random Blood Glucose Test comprises obtaining a blood sample at a random time point from a subject suspected of having Diabetes. Blood glucose values can be expressed in milligrams per deciliter (mg/dL) or millimoles per liter (mmol/L). A random blood glucose level of 200 mg/dL (11.1 mmol/L) or higher indicates the subject likely has Diabetes, especially when coupled with any of the signs and symptoms of Diabetes, such as frequent urination and extreme thirst.

For the fasting blood glucose test, a blood sample is obtained after an overnight fast. A fasting blood glucose level less than 100 mg/dL (5.6 mmol/L) is considered normal. A fasting blood glucose level from 100 to 125 mg/dL (5.6 to 6.9 mmol/L) is considered prediabetic, while a level of 126 mg/dL (7 mmol/L) or higher on two separate tests is indicative of Diabetes.

Type 1 Diabetes can also be distinguished from type 2 Diabetes using a C-peptide assay, which is a measure of endogenous insulin production. The presence of anti-islet antibodies (to Glutamic Acid Decarboxylase, Insulinoma Associated Peptide-2 or insulin), or lack of insulin resistance, determined by a glucose tolerance test, is also indicative of type 1, as many type 2 diabetics continue to produce insulin internally, and all have some degree of insulin resistance.

Testing for GAD 65 antibodies has been proposed as an improved test for differentiating between type 1 and type 2 Diabetes as it appears that the immune system is involved in Type 1 Diabetes etiology.

The non-obese diabetic (NOD) mouse provides an animal model for the spontaneous development of Type 1 Diabetes. NOD mice develop insulitis as a result of leukocyte infiltration into the pancreatic islet, which in turn leads to the destruction of pancreatic islets and a Type 1 diabetic phenotype (Makino S, et al., (1980) *Jikken Dobutsu* 29 (1): 1-13; Kikutani H, and Makino S (1992) *Adv. Immunol.* 51: 285-322).

The methods described herein are also useful for treating Type 1 Diabetes in a subject.

In the context of type 1 Diabetes, "treating" or "treatment" refers to partial or total inhibition, delay or prevention of the progression of type 1 Diabetes, pre-diabetic conditions, and complications associated with type 1 Diabetes or pre-diabetic conditions; inhibition, delay or prevention of the recurrence of type 2 Diabetes, pre-diabetic conditions, or complications associated with type 1 Diabetes or pre-diabetic conditions; or the prevention of the onset or development of type 1 Diabetes, pre-diabetic conditions, or complications associated with type 1 Diabetes or pre-diabetic conditions (chemoprevention) in a subject.

In the context of Type 1 Diabetes, "therapeutically effective amount" refers to an amount of GOAT inhibitor and/or ghrelin antagonist administered to a subject that is sufficient to produce a statistically significant, measurable change in at least one symptom of Type 1 Diabetes, such as glycosylated hemoglobin level, fasting blood glucose level, hypoinsulinemia, etc. . . . . Efficacy of treatment with a peptide can be assessed by measuring changes in blood glucose and/or insulin levels or as described below.

The efficacy of a given treatment for Type 1 Diabetes can be determined by the skilled clinician. However, a treatment is considered "effective treatment," as the term is used herein, if any one or all of the signs or symptoms of Type 1 Diabetes, for example, hyperglycemia are altered in a beneficial manner, other clinically accepted symptoms or markers of disease are improved, or even ameliorated, e.g., by at least 10% following treatment with a peptide as described herein. Efficacy can also be measured by a failure of an individual to worsen as assessed by hospitalization or need for medical interventions (i.e., progression of the disease is halted or at least slowed). Methods of measuring these indicators are known to those of skill in the art and/or described herein. Treatment includes any treatment of a disease in an individual or an animal (some non-limiting examples include a human, or a mammal) and includes: (1) inhibiting the disease, e.g., arresting, or slowing the loss of beta cells; or (2) relieving the disease, e.g., causing regression of symptoms, increasing pancreatic beta cell mass; and (3) preventing or reducing the likelihood of the development of a complication of Type 1 Diabetes, e.g., diabetic retinopathy.

As used herein, the term "delaying the onset of Type 1 Diabetes" in a subject refers to a delay of onset of at least one symptom of Type 1 Diabetes (e.g., hyperglycemia and/or hypoinsulinemia) of at least one week, at least 2 weeks, at least 1 month, at least 2 months, at least 6 months, at least 1 year, at least 2 years, at least 5 years, at least 10 years, at least 20 years, at least 30 years, at least 40 years or more, and can include the entire lifespan of the subject.

Type 2 Diabetes results from a combination of insulin resistance and impaired insulin secretion but ultimately many people with Type 2 Diabetes show markedly reduced pancreatic β-cell mass and function which, in turn, causes Type 2 diabetic persons to have a "relative" deficiency of insulin because pancreatic β-cells are producing some insulin, but the insulin is either too little or isn't working properly to adequately allow glucose into cells to produce energy. Recent autopsy studies have shown clear evidence of ongoing β-cell death (apoptosis) in people with Type 2 Diabetes. Therefore, therapeutic approaches to provide more β-cells could provide a significant treatment for reversing or curing Type 2 Diabetes.

Uncontrolled Type 2 Diabetes leads to excess glucose in the blood, resulting in hyperglycemia, or high blood sugar. A person with Type 2 Diabetes experiences fatigue, increased thirst, frequent urination, dry, itchy skin, blurred vision, slow healing cuts or sores, more infections than usual, numbness and tingling in feet. Without treatment, a person with Type 2 Diabetes will become dehydrated and develop a dangerously low blood volume. If Type 2 Diabetes remains uncontrolled for a long period of time, more serious symptoms may result, including severe hyperglycemia (blood sugar over 600 mg) lethargy, confusion, shock, and ultimately "hyperosmolar hyperglycemic non-ketotic coma." Persistent or uncontrolled hyperglycemia is associated with increased and premature morbidity and mortality. As such, therapeutic control of glucose homeostasis, lipid metabolism, obesity, and hypertension are critically important in the clinical management and treatment of Diabetes mellitus.

The methods of the invention are useful for treating type 2 Diabetes Mellitus or a pre-diabetic condition in a subject or preventing type 2 Diabetes or pre-diabetic conditions in a subject. Skilled artisan is well aware that type 2 Diabetes Mellitus is also known as non-insulin dependent Diabetes mellitus.

"Complications related to type 2 Diabetes" or "complications related to a pre-diabetic condition" can include, without limitation, diabetic retinopathy, diabetic nephropathy, blindness, memory loss, renal failure, cardiovascular disease (including coronary artery disease, peripheral artery disease, cerebrovascular disease, atherosclerosis, and hypertension), neuropathy, autonomic dysfunction, hyperglycemic hyperosmolar coma, or combinations thereof.

In the context of type 2 Diabetes, "treating" or "treatment" refers to partial or total inhibition, delay or prevention of the progression of type 2 Diabetes, pre-diabetic conditions, and complications associated with type 2 Diabetes or pre-diabetic conditions; inhibition, delay or prevention of the recurrence of type 2 Diabetes, pre-diabetic conditions, or complications associated with type 2 Diabetes or pre-diabetic conditions; or the prevention of the onset or development of type 2 Diabetes, pre-diabetic conditions, or complications associated with type 2 Diabetes or pre-diabetic conditions (chemoprevention) in a subject.

"Obesity" is a condition in which there is an excess of body fat. The operational definition of obesity is based on the Body Mass Index (BMI), which is calculated as body weight per height in meters squared ($kg/m^2$). "Obesity" refers to a condition whereby an otherwise healthy subject has a Body Mass Index (BMI) greater than or equal to $30 \ kg/m^2$, or a condition whereby a subject with at least one co-morbidity has a BMI greater than or equal to $27 \ kg/m^2$. An "obese subject" is an otherwise healthy subject with a Body Mass Index (BMI) greater than or equal to $30 \ kg/m^2$ or a subject with at least one co-morbidity with a BMI greater than or equal to $27 \ kg/m^2$. A "subject at risk of obesity" is an otherwise healthy subject with a BMI of $25 \ kg/m^2$ to less than $30 \ kg/m^2$ or a subject with at least one co-morbidity with a BMI of $25 \ kg/m^2$ to less than $27 \ kg/m^2$.

The term "drug" or "compound" as used herein refers to a chemical entity or biological product, or combination of chemical entities or biological products, administered to a person to treat or prevent or control a disease or condition.

As used herein, the terms "effective" and "effectiveness" includes both pharmacological effectiveness and physiological safety. Pharmacological effectiveness refers to the ability of the treatment to result in a desired biological effect in the patient. Physiological safety refers to the level of toxicity, or other adverse physiological effects at the cellular, organ and/or organism level (often referred to as side-effects) resulting from administration of the treatment. "Less effective" means that the treatment results in a therapeutically significant lower level of pharmacological effectiveness and/or a therapeutically greater level of adverse physiological effects. The ghrelin receptor antagonists described herein are effective in treating obesity and obesity related diseases and disorders including diabetes and various types of cancer.

A "cancer" in an animal refers to the presence of cells possessing characteristics typical of cancer-causing cells, such as uncontrolled proliferation, immortality, metastatic potential, rapid growth and proliferation rate, and certain characteristic morphological features. Often, cancer cells will be in the form of a tumor, but such cells may exist alone within an animal, or may be a non-tumorigenic cancer cell, such as a leukemia cell. In some circumstances, cancer cells will be in the form of a tumor; such cells may exist locally within an animal, or circulate in the blood stream as independent cells, for example, leukemic cells. Examples of cancer include but are not limited to breast cancer, a melanoma, adrenal gland cancer, biliary tract cancer, bladder cancer, brain or central nervous system cancer, bronchus cancer, blastoma, carcinoma, a chondrosarcoma, cancer of the oral cavity or pharynx, cervical cancer, colon cancer, colorectal cancer, esophageal cancer, gastrointestinal cancer, glioblastoma, hepatic carcinoma, hepatoma, kidney cancer, leukemia, liver cancer, lung cancer, lymphoma, non-small cell lung cancer, osteosarcoma, ovarian cancer, pancreas cancer, peripheral nervous system cancer, prostate cancer, sarcoma, salivary gland cancer, small bowel or appendix cancer, small-cell lung cancer, squamous cell cancer, stomach cancer, testis cancer, thyroid cancer, urinary bladder cancer, uterine or endometrial cancer, and vulval cancer.

The term "inverse agonist" as used herein refers to an agent which binds to the same ghrelin receptor binding-site as an agonist for that receptor but exerts the opposite pharmacological effect, decrease intracellular IP3 levels.

The term "antagonist" is used in the broadest sense, and includes any molecule that partially or fully blocks, inhibits, or neutralizes a biological activity of ghrelin.

As used herein, the term "peptide' refers to a short polymer formed from the linking of amino acids. A "peptide" is at least 4, or at least 5 amino acids and no more than to 50 amino acids in length.

As used herein, the term "metabolic syndrome" refer to a group of metabolic risk factors in one person. They include: abdominal obesity (excessive fat tissue in and around the abdomen), atherogenic dyslipidemia (blood fat disorders—high triglycerides, low HDL cholesterol and high LDL cholesterol—that foster plaque buildups in artery walls), elevated blood pressure, insulin resistance or glucose intolerance (the body can't properly use insulin or blood sugar), rrothrombotic state (e.g., high fibrinogen or plasminogen activator inhibitor-1 in the blood), and proinflammatory state (e.g., elevated C-reactive protein in the blood). There are currently no well-accepted criteria for diagnosing the metabolic syndrome. The criteria proposed by the National Cholesterol Education Program (NCEP) Adult Treatment Panel III (ATP III), with minor modifications, are currently recommended and widely used.

Ghrelin O-Acyltransferase (GOAT) Inhibitor

In some embodiments, the methods described herein comprises administering an effective amount of ghrelin O-acyltransferase (GOAT) inhibitor.

In one embodiment, the GOAT inhibitor comprises an octanoylated ghrelin pentapeptide, and wherein the octanoylation is at position three of the pentapeptide.

In one embodiment, the octanoylated ghrelin pentapeptide is Gly-Ser-[Ser-Octanoyl³]-Phe-Leu (SEQ ID NO: 1). In another embodiment, the octanoylated ghrelin pentapeptide is Gly-Ser-[Dap-Octanoyl³]-Phe-Leu (SEQ ID NO: 2).

Ghrelin is a 28 amino acid, appetite-stimulating peptide hormone secreted by the food-deprived stomach. Serine-3 of ghrelin is acylated with an eight-carbon fatty acid, octanoate, which is required for its endocrine actions. Ghrelin that is deleted of the octanoate, known as desoctanoylated ghrelin is biologically inactive. Recently, the membrane bound acyltransferase that catalyses the addition of octanoate to Serine-3 was identified (28). The enzyme is named ghrelin O-acyltransferase (GOAT). GOAT was shown to also transfer octanoyl to a pentapeptide containing only the N-terminal five amino acids of proghrelin, the 94 amino acid protein precursor of ghrelin (29). Yang, et, al. 2008 (29) showed that GOAT activity could be inhibited by an octanoylated ghrelin pentapeptide, and its potency was enhanced 45-fold when the octanoylated serine-3 was replaced by octanoylated diaminopropionic acid.

In some embodiments, the GOAT inhibitors comprises ghrelin pentapeptides or peptidomimetics that have serine at position three and the serine at position 3 is not octanoylated. While not wishing to be bound by theory, such desoctanoylated ghrelin pentapeptides or peptidomimetics inhibits GOAT acylation of ghrelin by serving as decoy substrates to compete with desoctanoylated ghrelin thereby saturating the GOAT substrate binding sites.

Other examples of inhibitors that comprise octanoylated ghrelin pentapeptide include, but not limited to, peptides from Phoenix pharmaceutical Inc., e.g. Octanoylated Ghrelin Pentapeptide/Ghrelin (1-5)-Amide, catalog No. 031-41: Gly-Ser-Ser(Octanoyl)-Phe-Leu-NH$_2$ (SEQ ID NO: 94); Ghrelin (1-5)-Amide [Ser3(Des-Octanoyl)], catalog No. 031-42: Gly-Ser-Ser(Des-Octanoyl)-Phe-Leu-NH$_2$ (SEQ ID NO: 5); Ghrelin [Dap-Octanyol3], catalog No. 031-58: Gly-Ser-Dap(Octanoyl)-Phe-Leu-Ser-Pro-Glu-His-Gln-Arg-Val-Gln-Gln-Arg-Lys-Glu-Ser-Lys-Lys-Pro-Pro-Ala-Lys-Leu-Gln-Pro-Arg-NH$_2$ (SEQ ID NO: 6); [Dap3] Octanoyl-Ghrelin (1-5) Amide, catalog No.: 032-14: Gly-Ser-Dap(Octanoyl)-Phe-Leu-NH$_2$ (SEQ ID NO: 7); Ghrelin (1-4)-Amide, catalog No. 031-67: Gly-Ser-Ser(Des-Octanoyl)-Phe-NH$_2$ (SEQ ID NO: 8); Ghrelin (1-18) [Ser3(Des-Octanoyl)] (Motilin-Related Peptide), catalog No.: 031-47: Gly-Ser-Ser(Des-Octanoyl)-Phe-Leu-Ser-Pro-Glu-His-Gln-Arg-Val-Gln-Gln-Arg-Lys-Glu-Ser-NH$_2$ (SEQ ID NO: 9); and Ghrelin [Tyr29] [Ser3(Des-Octanoyl)], catalog No.: 031-55: Gly-Ser-Ser(Des-Octanoyl)-Phe-Leu-Ser-Pro-Glu-His-Gln-Arg-Val-Gln-Gln-Arg-Lys-Glu-Ser-Lys-Lys-Pro-Pro-Ala-Lys-Leu-Gln-Pro-Arg-Tyr-NH$_2$ (SEQ ID NO: 10).

Ghrelin Receptor Antagonist and/or Growth Hormone Secretatogue Antagonist Compounds Ghrelin receptor antagonist and/or growth hormone secretatogue antagonist compounds useful in the methods described herein are fully described in PCT/US2007/10389 which is incorporated herein by reference in its entirety.

In some embodiments, the ghrelin receptor antagonist compounds useful in the methods described herein includes a compound with the formula Tyr-DTrp-DLys-Trp-DPhe-NH2 (SEQ ID NO: 11), Tyr-DTrp-Lys-Trp-DPhe-NH2 (SEQ ID NO: 12), His-DTrp-DLys-Trp-DPhe-NH2 (SEQ ID NO: 13), His-DTrp-DLys-Phe-DTrp-NH2 (SEQ ID NO: 14), His-DTrp-DArg-Trp-DPhe-NH2 (SEQ ID NO: 15), His-DTrp-DLys-Trp-DPhe-Lys-NH2 (SEQ ID NO: 16), DesaminoTyr-DTrp-Ala-Trp-DPhe-NH2 (SEQ ID NO: 17), DesaminoTyr-DTrp-DLys-Trp-DPhe-NH2 (SEQ ID NO: 18), DesaminoTyr-DTrp-Ser-Trp-DPhe-Lys-NH2 (SEQ ID NO: 19), DesaminoTyr-DTrp-Ser-Trp-DPhe-NH2 (SEQ ID NO: 20), His-DTrp-DTrp-Phe-Met-NH2 (SEQ ID NO: 21), Tyr-DTrp-DTrp-Phe-Phe-NH2 (SEQ ID NO: 22), Glyψ[CH2NH]-Dβ-Nal-Ala-Trp-DPhe-Lys-NH2 (SEQ ID NO: 23), Glyψ[CH$_2$NH]-DβNal-DLys-Trp-DPhe-Lys-NH$_2$ (SEQ ID NO: 24), DAla-DβNal-DLys-DTrp-Phe-Lys-NH2 (SEQ ID NO: 25), His-DβNal-DLys-Trp-DPhe-Lys-NH2 (SEQ ID NO: 26), Ala-His-DTrp-DLys-Trp-DPhe-Lys-NH2 (SEQ ID NO: 27), Alaψ[CH2NH]-DβNal-Ala-Trp-DPhe-Lys-NH2 (SEQ ID NO: 28), DβNal-Ala-Trp-DPhe-Ala-NH2 (SEQ ID NO: 29), DAla-DcyclohexylAla-Ala-Phe-DPhe-Nle-NH2 (SEQ ID NO: 30), DcyclohexylAla-Ala-Phe-DTrp-Lys-NH2 (SEQ ID NO: 31), DAla-DβNal-Ala-Thr-DThr-Lys-NH2 (SEQ ID NO: 32), DcyclohexylAla-Ala-Trp-DPhe-NH2 (SEQ ID NO: 33), DAla-DβNal-Ala-Ala-DAla-Lys-NH2 (SEQ ID NO: 34), DβNal-Ala-Trp-DPhe-Leu-NH2 (SEQ ID NO: 35), His-DTrp-Phe-Trp-DPhe-Lys-NH2 (SEQ ID NO: 36), DAla-Dβ-Nal-DAla-DTrp-Phe-Lys-NH2 (SEQ ID NO: 37), βAla-DAla-DTrp-Phe-NH2 (SEQ ID NO: 38), His-Trp-DAla-DTrp-Phe-LysNH2 (SEQ ID NO: 39), DLys-DβNal-Ala- Trp-DPhe-Lys-NH2 (SEQ ID NO: 40), DAla-DβNal-DLys-DTrp-Phe-Lys-NH2 (SEQ ID NO: 41), Tyr-DAla-Phe-Aib-NH2 (SEQ ID NO: 42), Tyr-DAla-Sar-NMePhe-NH2 (SEQ ID NO: 43), αγAbu-DTrp-DTrp-Ser-NH2 (SEQ ID NO: 44), αγAbu-DTrp-DTrp-Lys-NH2 (SEQ ID NO: 45), αγAbu-DTrp-DTrp-Orn-NH2 (SEQ ID NO: 46), αAbu-DTrp-DTrp-Orn-NH2 (SEQ ID NO: 47), DThr-DαNal-DTrp-DPro-Arg-NH2 (SEQ ID NO: 48), DAla-Ala-DAla-DTrp-Phe-Lys-NH2 (SEQ ID NO: 49), Alaψ[CH2NH]His-DTrp-Ala-Trp-DPhe-Lys-NH2 (SEQ ID NO: 50), Lys-DHis-DTrp-Phe-NH2 (SEQ ID NO: 51), γAbu-DTrp-DTrp-Orn-NH2 (SEQ ID NO: 52), inip-Trp-Trp-Phe-NH2 (SEQ ID NO: 53), Ac-DTrp-Phe-DTrp-Leu-NH2 (SEQ ID NO: 54), Ac-DTrp-Phe-DTrp-Lys-NH2 (SEQ ID NO: 55), Ac-DTrp-DTrp-Lys-NH2 (SEQ ID NO: 56), DLys-Tyr-DTrp-DTrp-Phe-Lys-NH2 (SEQ ID NO: 57), Ac-DβNal-Leu-Pro-NH2 (SEQ ID NO: 58), βAla-Trp-DTrp-DTrp-Orn-NH2 (SEQ ID NO: 59), DVal-DαNal-DTrp-Phe-Arg-NH2 (SEQ ID NO: 60), DLeu-DαNal-DTrp-Phe-Arg-NH2 (SEQ ID NO: 61), CyclohexylAla-DαNal-DTrp-Phe-Arg-NH2 (SEQ ID NO: 62), DTrp-DαNal-DTrp-Phe-Arg-NH2 (SEQ ID NO: 63), DAla-DβNal-DPro-Phe-Arg-NH2 (SEQ ID NO: 64), Ac-DαNal-DTrp-Phe-Arg-NH2 (SEQ ID NO: 65), DαNal-DTrp-Phe-Arg-NH2 (SEQ ID NO: 66), His-DTrp-DTrp-Lys-NH2 (SEQ ID NO: 67), Ac-DβNal-DTrp-NH2 (SEQ ID NO: 68), αAib-DTrp-DcyclohexylAla-NH2 (SEQ ID NO: 69), αAib-DTrp-DAla-cyclohexylAla-NH2 (SEQ ID NO: 70), DAla-DcyclohexylAla-Ala-Ala-Phe-DPhe-Nle-NH2 (SEQ ID NO: 71), DPhe-Ala-Phe-DPal-NH2 (SEQ ID NO: 72), DPhe-Ala-Phe-DPhe-Lys-NH2 (SEQ ID NO: 73), DLys-Tyr-DTrp-DTrp-Phe-NH2 (SEQ ID NO: 74), Ac-DLys-Tyr-DTrp-DTrp-Phe-NH2 (SEQ ID NO: 75), Arg-DTrp-Leu-Tyr-Trp-Pro(cyclic Arg-Pro) (SEQ ID NO: 76), Ac-DβNal-PicLys-ILys-DPhe-NH2 (SEQ ID NO: 77), DPal-Phe-DTrp-Phe-Met-NH2 (SEQ ID NO: 78), DPhe-Trp-DPhe-Phe-Met-NH2 (SEQ ID NO: 79), DPal-Trp-DPhe-Phe-Met-NH2 (SEQ ID NO: 80), βAla-Pal-DTrp-DTrp-Orn-NH2 (SEQ ID NO: 81), αγAbu-Trp-DTrp-DTrp-Orn-NH2 (SEQ ID NO: 82), βAla-Trp-DTrp-DTrp-Lys-NH2 (SEQ ID NO: 83), γAbu-Trp-DTrp-DTrp-Orn-NH2 (SEQ ID NO: 84), Ava-Trp-DTrp-DTrp-Orn-NH2 (SEQ ID NO: 85), DLys-Tyr-DTrp-Ala-Trp-DPhe-NH2 (SEQ ID NO: 86), His-DTrp-DArg-Trp-DPhe-NH2 (SEQ ID NO: 87), <Glu-His-Trp-DSer-DArg-NH2 (SEQ ID NO: 88), DPhe-DPhe-DTrp-Met-DLys-NH2 (SEQ ID NO: 89), O-(2-methylallyl) benzophonone oxime, (R)-2-amino-3-(1H-indol-3-yl)-1-(4-phenylpiperidin-1-yl)propan-1-one, N—((R)-1-((R)-1-((S)-3-(1H-indol-3-yl)-1-oxo-1-(4-phenylpiperidin-1-yl)propan-2-ylamino)-6-amino-1-oxohexan-2-ylamino)-3-hydroxy-1-oxopropan-2-yl)benzamide, (S)—N—((S)-3-(1H-indol-3-yl)-1-oxo-1-(4-phenylpiperidin-1-yl)propan-2-yl)-6-acetamido-2-((S)-2-amino-3-(benzyloxy)propanamido) hexanamide, (S)—N-((R)-3-(1H-indol-3-yl)-1-oxo-1-(4-phenylpiperidin-1-yl)propan-2-yl)-2-4S)-2-acetamido-3-(benzyloxy)propanamido)-6-aminohexanamide, (R)—N-(3-(1H-indol-3-yl)-1-(4-(2-methoxyphenyl)piperidin-1-yl)-1-oxopropan-2-yl)-4-aminobutanamide, (R)—N-(3-(1H-indol-3-yl)-1-(4-(2-methoxyphenyl)piperidin-1-yl)-1-oxopropan-2-yl)-2-amino-2-methylpropanamide, methyl 3-(p-tolylcarbamoyl)-2-naphthoate, ethyl 3-(4-(2-methoxyphenyl)piperidine-1-carbonyl)-2-naphthoate, 3-(2-methoxyphenylcarbamoyl)-2-naphthoate, (S)-2,4-diamino-N—((R)-3-(naphthalen-2-ylmethoxy)-1-oxo-1-(4-phenylpiperidin-1-yl)propan-2-yl)butanamide, naphthalene-2,3-diylbis((4-(2-methoxyphenyl)piperazin-1-yl) methanone), (R)-2-amino-N-(3-(benzyloxy)-1-oxo-1-(4-phenylpiperazin-1-yl)propan-2-yl)-2-methylpropanamide, or (R)-2-amino-3-(benzyloxy)-1-(4-phenylpiperazin-1-yl) propan-1-one, and pharmaceutically acceptable salts, prodrugs, or active metabolites thereof.

The antagonists embodied in the invention can be synthesized according to the usual methods of solution and solid phase peptide chemistry, or by classical methods known in the art. Purification of peptides is well known in the art and can be, for example, HPLC. Methods describing useful peptide synthesis and purification methods can be found, for example, in U.S. Patent Application No. 20060084607.

Synthesis of Peptides

Peptides described herein can be synthetically constructed by suitable known peptide polymerization techniques, such as exclusively solid phase techniques, partial solid-phase techniques, fragment condensation or classical solution couplings. For example, the peptides of the invention can be synthesized by the solid phase method using standard methods based on either t-butyloxycarbonyl (BOC) or 9-fluorenylmethoxy-carbonyl (FMOC) protecting groups. This methodology is described by G. B. Fields et al. in Synthetic Peptides: A User's Guide, W. M. Freeman & Company, New York, N.Y., pp. 77-183 (1992) and in the textbook "Solid-Phase Synthesis", Stewart & Young, Freemen & Company, San Francisco, 1969, and are exemplified by the disclosure of U.S. Pat. No. 4,105,603, issued Aug. 8, 1979. Classical solution synthesis is described in detail in "Methoden der Organischen Chemic (Houben-Weyl): Synthese von Peptiden", E. Wunsch (editor) (1974) Georg Thieme Verlag, Stuttgart West Germany. The fragment condensation method of synthesis is exemplified in U.S. Pat. No. 3,972,859. Other available syntheses are exemplified in U.S. Pat. No. 3,842,067, U.S. Pat. No. 3,872,925, issued Jan. 28, 1975, Merrifield B, Protein Science (1996), 5: 1947-1951; The chemical synthesis of proteins; Mutter M, Int J Pept Protein Res 1979 March; 13 (3): 274-7 Studies on the coupling rates in liquid-phase peptide synthesis using competition experiments; and Solid Phase Peptide Synthesis in the series Methods in Enzymology (Fields, G. B. (1997) Solid-Phase Peptide Synthesis. Academic Press, San Diego. #9830). Contents of all of the foregoing disclosures are incorporated herein by reference.

Methods for preparing peptide mimetics include modifying the N-terminal amino group, the C-terminal carboxyl group, and/or changing one or more of the amino linkages in the peptide to a non-amino linkage. Two or more such modifications can be coupled in one peptide mimetic inhibitor. The following are examples of modifications of peptides to produce peptide mimetics as described in U.S. Pat. Nos. 5,643,873 and 5,654,276, the content of both of which is incorporated herein by reference.

Designing Peptide Mimetics

Methods of designing peptide mimetics and screening of functional peptide mimetics are well known to those skilled in the art. One basic method of designing a molecule which mimics a known protein or peptide is first to identify the active region(s) of the known protein (for example, in the case of an antibody-antigen interaction, one identifies which region(s) of the antibody that permit binding to the antigen), and then searches for a mimetic which emulates the active region. If the active region of a known protein is relatively small, it is anticipated that a mimetic will be smaller (e.g. in molecular weight) than the protein, and correspondingly easier and cheaper to synthesize. Such a mimetic could be used as a convenient substitute for the protein, as an agent for interacting with the target molecule.

For example, Reineke et al. (1999, Nature Biotechnology, 17; 271-275, contents of which is herein incorporated by reference) designed a mimic molecule which mimics a binding site of the interleukin-10 protein using a large library of short synthetic peptides, each of which corresponded to a short section of interleukin 10. The binding of each of these peptides to the target (in this case an antibody against interleukin-10) was then tested individually by an assay technique, to identify potentially relevant peptides. Phage display libraries of peptides and alanine scanning method can be used.

Other methods for designing peptide mimetics to a particular peptide or protein include those described in European Patent EP1206494, the SuperMimic program by Andrean Goede et. al. 2006 BMC Bioinformatics, 7:11; and MIMETIC program by W. Campbell et. al., 2002, Microbiology and Immunology 46:211-215. The SuperMimic program is designed to identify compounds that mimic parts of a protein, or positions in proteins that are suitable for inserting mimetics. The application provides libraries that contain peptidomimetic building blocks on the one hand and protein structures on the other. The search for promising peptidomimetic linkers for a given peptide is based on the superposition of the peptide with several conformers of the mimetic. New synthetic elements or proteins can be imported and used for searching. The MIMETIC computer program, which generates a series of peptides for interaction with a target peptide sequence is taught by W. Campbell et. al., 2002. In depth discussion of the topic is reviewed in "Peptide Mimetic Design with the Aid of Computational Chemistry" by James R. Damewood Jr. in Reviews in Computational Chemistry Reviews in Computational Chemistry, January 2007, Volume 9 Book Series: Reviews in Computational Chemistry, Editor(s): Kenny B. Lipkowitz, Donald B. BoydPrint ISBN: 9780471186397 ISBN: 9780470125861 Published by John Wiley &Sons, Inc.; and in T. Tselios, et. al., Amino Acids, 14: 333-341, 1998. Content of all of the references described in this paragraph is herein incorporated by reference.

Methods for preparing libraries containing diverse populations of peptides, peptoids and peptidomimetics are well known in the art and various libraries are commercially available (see, for example, Ecker and Crooke, Biotechnology 13:351-360 (1995), and Blondelle et al., Trends Anal. Chem. 14:83-92 (1995), and the references cited therein, each of which is incorporated herein by reference; see, also, Goodman and Ro, Peptidomimetics for Drug Design, in "Burger's Medicinal Chemistry and Drug Discovery" Vol. 1 (ed. M. E. Wolff; John Wiley & Sons 1995), pages 803-861, and Gordon et al., J. Med. Chem. 37:1385-1401 (1994), each of which is incorporated herein by reference). One skilled in the art understands that a peptide can be produced in vitro directly or can be expressed from a nucleic acid, which can be produced in vitro. Methods of synthetic peptide and nucleic acid chemistry are well known in the art. Content of all of the references described in this paragraph is herein incorporated by reference.

A library of peptide molecules also can be produced, for example, by constructing a cDNA expression library from mRNA collected from a tissue of interest. Methods for producing such libraries are well known in the art (see, for example, Sambrook et. al., Molecular Cloning: A laboratory manual (Cold Spring Harbor Laboratory Press 1989), which is incorporated herein by reference). Preferably, a peptide encoded by the cDNA is expressed on the surface of a cell or a virus containing the cDNA.

Administration and Formulation of GOAT Inhibitors and Ghrelin Receptor Antagonist Compound Thus, in connection with the administration of a ghrelin receptor antagonist compound of the invention, e.g. a compound which is "effective against" a disease or disorder indicates that administration in a clinically appropriate manner results in a beneficial effect for at least a statistically significant fraction of patients, such as a improvement of symptoms, a cure, a reduction in symptoms or disease load, reduction in tumor mass or cell numbers, extension of life, improvement in quality of life, or other effect generally recognized as positive by medical doctors familiar with treating the particular type of disease or condition.

The therapeutic compositions of GOAT inhibitors and ghrelin receptor antagonist compounds can be administered intravenously (i.v.), as by injection of a unit dose, for example. The term "unit dose" when used in reference to a therapeutic composition of the present invention refers to physically discrete units suitable as unitary dosage for the subject, each unit containing a predetermined quantity of active material calculated to produce the desired therapeutic effect in association with the required diluent; i.e., carrier, or vehicle. Suitable therapeutic vehicle include, but not limited to, sterile saline, buffered phosphate saline, lactated Ringer's saline.

The compositions are administered in a manner compatible with the dosage formulation, and in a therapeutically effective amount. The quantity to be administered and timing depends on the subject to be treated, capacity of the subject's system to utilize the active ingredient, and degree of therapeutic effect desired. Precise amounts of active ingredient required to be administered depend on the judgment of the practitioner and are peculiar to each individual.

The compositions of the invention comprising GOAT inhibitors and/or ghrelin receptor antagonists having the formulae I-VII can be administered in any suitable manner, e.g., topically, parenterally, or by inhalation. The term "parenteral" includes injection, e.g., by subcutaneous, intravenous, or intramuscular routes, also including localized administration, e.g., at a site of disease or injury. Sustained release from implants is also contemplated. One skilled in the pertinent art will recognize that suitable dosages will vary, depending upon such factors as the nature of the disorder to be treated, the patient's body weight, age, and general condition, and the route of administration. Preliminary doses can be determined according to animal tests, and the scaling of dosages for human administration is performed according to art-accepted practices.

The amount of GOAT inhibitor and ghrelin receptor antagonist or combination of compounds of the present invention administered will vary depending on numerous factors, e.g., the particular animal treated, its age and sex, the desired therapeutic affect, the route of administration and which polypeptide or combination of polypeptides are employed. In all instances, however, a dose effective (therapeutically effective amount) to promote inhibition of growth hormone level in the blood of the recipient animal is used. The dose will depend on a combination of factors, i.e., antagonist receptor action(s), potency, efficacy, pharmacokinetics, pharmacodynamics, route of administration, method of administration and clinical disorder and/or metabolic status. Generally, dosage levels of between 0.0001 to 100 mg/kg of body weight daily are administered to patients and mammals in need to obtain effective inhibition of growth hormone in the blood. The preferred amount can readily be determined empirically by the skilled artisan.

In some embodiments, combinations of ghrelin receptor antagonist compounds are used in any of the methods described herein. In other embodiments, combinations of GOAT inhibitors are used in any of the methods described herein. When combinations of ghrelin receptor antagonist compounds and/or combinations of GOAT inhibitors are used, lower amounts of the antagonist can be used in the treatment of diseases and disorders described herein. This occurs when one compound exhibit synergistic effect over the activity of a second compound when used in combination.

The GOAT inhibitors and ghrelin receptor antagonist compounds can be administrated to a subject in combination with another pharmaceutically active agent or treatment modality for a particular indication. Exemplary pharmaceutically active compound include, but are not limited to, those found in *Harrison's Principles of Internal Medicine,* 13$^{th}$ Edition, Eds. T. R. Harrison et al. McGraw-Hill N.Y., NY; Physicians Desk Reference, 50$^{th}$ Edition, 1997, Oradell New Jersey, Medical Economics Co.; Pharmacological Basis of Therapeutics, 8$^{th}$ Edition, Goodman and Gilman, 1990; United States Pharmacopeia, The National Formulary, USP XII NF XVII, 1990; current edition of Goodman and Oilman's *The Pharmacological Basis of Therapeutics*; and current edition of *The Merck Index*, the complete contents of all of which are incorporated herein by reference.

In another embodiment, the GOAT inhibitors and ghrelin receptor antagonist compounds of the inventions can be used in combination with other treatment regime for treating the diseases and disorders associated with obesity, overeating, diabetes, unregulated cellular proliferation, and cancer.

The of GOAT inhibitors and ghrelin receptor antagonist compounds of the present invention can be formulation for sustained or controlled release. The antagonists and/inhibitors of the present invention can be admixed with biologically compatible polymers or matrices which control the release rate of the antagonists into the immediate environment. Controlled or sustained release compositions include formulation in lipophilic depots (e.g., fatty acids, waxes, oils). Also contemplated by the invention are particulate compositions coated with polymers (e.g., poloxamers or poloxamines). Other embodiments of the compositions of the invention incorporate particulate forms, protective coatings, protease inhibitors or permeation enhancers for various routes of administration, including parenteral, pulmonary, nasal and oral.

Controlled release permits dosages to be administered over time, with controlled release kinetics. In some instances, delivery of the therapeutic agent is continuous to the site where treatment is needed, for example, over several weeks. Controlled release over time, for example, over several days or weeks, or longer, permits continuous delivery of the therapeutic agent to obtain optimal treatment. The controlled delivery vehicle is advantageous because it protects the therapeutic agent from degradation in vivo in body fluids and tissue, for example, by proteases.

Controlled release from the pharmaceutical formulation may be designed to occur over time, for example, for greater than about 12 or 24 hours. The time of release may be selected, for example, to occur over a time period of about 12 hours to 24 hours; about 12 hours to 42 hours; or, e.g., about 12 to 72 hours. In another embodiment, release may occur for example on the order of about 2 to 90 days, for example, about 3 to 60 days. In one embodiment, the GOAT inhibitor and/or ghrelin receptor antagonist is delivered locally over a time period of about 7-21 days, or about 3 to 10 days. In other instances, the therapeutic agent is administered over 1, 2, 3 or more weeks in a controlled dosage. The controlled release time may be selected based on the condition treated.

"Controlled release" also encompasses patterned delivery (e.g., intermittent delivery over a period of time that is interrupted by regular or irregular time intervals). Without limitation, the intermittent delivery can be interrupted by a period of at least 30 minutes, at least 1 hour, at least 2 hours, at least 3 hours, at least 4 hours, at least 5 hours, at least 6 hours, at least 12, at least 24 hours, at least 1 day, at least 2 days, at least 3 days, at least 4 days, at least 5 days, at least 6 days, at least 1 week, at least one month or more As used herein, the terms "pharmaceutically acceptable", "physiologically tolerable" and grammatical variations thereof, as they refer to compositions, carriers, diluents and reagents, are used interchangeably and represent that the materials are capable of administration to or upon a mammal without the production of undesirable physiological effects.

Compositions comprising an effective amount of a ghrelin receptor antagonist and GOAT inhibitor, in combination with other components, such as a physiologically acceptable diluent, carrier, or excipient, are provided herein. The antagonists/inhibitor can be formulated according to known methods used to prepare pharmaceutically useful compositions. They can be combined in admixture, either as the sole active material or with other known materials suitable for a given indication, with pharmaceutically acceptable diluents (e.g., saline, Tris-HCl, acetate, and phosphate buffered solutions), preservatives (e.g., thimerosal, benzyl alcohol, parabens), emulsifiers, solubilizers, adjuvants and/or carriers. Suitable formulations for pharmaceutical compositions include those described in Remington's Pharmaceutical Sciences, 16$^{th}$ ed. 1980, Mack Publishing Company, Easton, Pa., content of which is herein incorporated by reference.

In addition, such compositions can be complexed with polyethylene glycol (PEG), metal ions, or incorporated into polymeric compounds such as polyacetic acid, polyglycolic acid, hydrogels, dextran, etc., or incorporated into liposomes, microemulsions, micelles, unilamellar or multilamellar vesicles, erythrocyte ghosts or spheroblasts. Such compositions will influence the physical state, solubility, stability, rate of in vivo release, and rate of in vivo clearance, and are thus chosen according to the intended application.

Toxicity and therapeutic efficacy can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio D50/ED50. Compositions that exhibit large therapeutic indices, are preferred.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized.

The therapeutically effective dose can be estimated initially from cell culture assays. A dose may be formulated in animal models to achieve a circulating plasma concentration range that includes the IC50 (i.e., the concentration of the therapeutic which achieves a half-maximal inhibition of symptoms) as determined in cell culture. Levels in plasma may be measured, for example, by high performance liquid chromatography. The effects of any particular dosage can be monitored by a suitable bioassay.

The dosage may be determined by a physician and adjusted, as necessary, to suit observed effects of the treatment. Generally, the compositions are administered so that a GOAT inhibitor and/or ghrelin receptor antagonist is given at a dose from 1 μg/kg to 150 mg/kg, 1 μg/kg to 100 mg/kg, 1 μg/kg to 50 mg/kg, 1 μg/kg to 20 mg/kg, 1 μg/kg to 10 mg/kg, 1 μg/kg to 1 mg/kg, 100 μg/kg to 100 mg/kg, 100 μg/kg to 50 mg/kg, 100 μg/kg to 20 mg/kg, 100 μg/kg to 10 mg/kg, 100 μg/kg to 1 mg/kg, 1 mg/kg to 100 mg/kg, 1 mg/kg to 50 mg/kg, 1 mg/kg to 20 mg/kg, 1 mg/kg to 10 mg/kg, 10 mg/kg to 100 mg/kg, 10 mg/kg to 50 mg/kg, or 10 mg/kg to 20 mg/kg. It is to be understood that ranges given here include all intermediate ranges, for example, the range 1 mg/kg to 10 mg/kg includes 1 mg/kg to 2 mg/kg, 1 mg/kg to 3 mg/kg, 1 mg/kg to 4 mg/kg, 1 mg/kg to 5 mg/kg, 1 mg/kg to 6 mg/kg, 1 mg/kg to 7 mg/kg, 1 mg/kg to 8 mg/kg, 1 mg/kg to 9 mg/kg, 2 mg/kg to 10 mg/kg, 3 mg/kg to 10 mg/kg, 4 mg/kg to 10 mg/kg, 5 mg/kg to 10 mg/kg, 6 mg/kg to 10 mg/kg, 7 mg/kg to 10 mg/kg, 8 mg/kg to 10 mg/kg, 9 mg/kg to 10 mg/kg, and the like. It is to be further understood that the ranges intermediate to the given above are also within the scope of this invention, for example, in the range 1 mg/kg to 10 mg/kg, dose ranges such as 2 mg/kg to 8 mg/kg, 3 mg/kg to 7 mg/kg, 4 mg/kg to 6 mg/kg, and the like.

With respect to duration and frequency of treatment, it is typical for skilled clinicians to monitor subjects in order to determine when the treatment is providing therapeutic benefit, and to determine whether to increase or decrease dosage, increase or decrease administration frequency, discontinue treatment, resume treatment or make other alteration to treatment regimen. The dosing schedule can vary from once a week to daily depending on a number of clinical factors, such as the subject's sensitivity to the polypeptides. The desired dose can be administered at one time or divided into subdoses, e.g., 2-4 subdoses and administered over a period of time, e.g., at appropriate intervals through the day or other appropriate schedule. Such sub-doses can be administered as unit dosage forms. In some embodiments, administration is chronic, e.g., one or more doses daily over a period of weeks or months. Examples of dosing schedules are administration daily, twice daily, three times daily or four or more times daily over a period of 1 week, 2 weeks, 3 weeks, 4 weeks, 1 month, 2 months, 3 months, 4 months, 5 months, or 6 months or more.

Treatment of Diseases and Disorders

By "treatment", "prevention" or "amelioration" of a disease or disorder is meant delaying or preventing the onset of such a disease or disorder, reversing, alleviating, ameliorating, inhibiting, slowing down or stopping the progression, aggravation, deterioration or severity of a condition associated with such a disease or disorder. In one embodiment, the symptoms of a disease or disorder are alleviated by at least 5%, at least 10%, at least 20%, at least 30%, at least 40%, or at least 50%. The term "treatment" is intended to encompass also prophylaxis, therapy and cure.

In one embodiment, a method to treat obesity is encompassed. In particular, the present invention comprises methods for regulating food intake in a human subject; for improving a compliance of a human subject to caloric restriction; and for reducing a desire of a human subject to consume an over-abundance of calories and/or fats. This method comprises the administration of an effective amount of ghrelin receptor antagonist and/or an effective amount of ghrelin O-acyltransferase (GOAT) inhibitor as described above.

In some embodiments, the food intake is reduced by at least 5%, at least 10%, at least 20%, at least 30%, at least 40%, at least 50%, at least 60%, at least 70%, at least 80%, at least 90%, at least 95% or more relative to subject that is not undergoing treatment. The amount of food intake can be based on the number of calories or on the weight of food.

The present invention further provides a method for preventing or reducing weight gain in a human subject, by administration of an effective amount of ghrelin receptor antagonist and/or an effective amount of GOAT inhibitor that have a pharmacological half-life that allows an efficient treatment regime thereof.

Also encompassed are methods for reducing a desire of a human subject to consume calories following gastric banding or gastric bypass surgery, by administration of an effective amount of a GOAT inhibitor and/or an effective amount of a ghrelin receptor antagonist.

In addition to the obesity related disorders discussed above, simultaneous administration of ghrelin receptor antagonist compositions and GOAT inhibitors are useful in the treatment or prevention of the following obesity related diseases and/or disorders: overeating; bulimia; hypertension; diabetes, elevated plasma insulin concentrations; insulin resistance; dyslipidemias; hyperlipidemia; endometrial, breast, prostate and colon cancer; osteoarthritis; obstructive sleep apnea; cholelithiasis; gallstones; abnormal heart rhythms; heart arrythymias; myocardial infarction; congestive heart failure; coronary heart disease; sudden death; stroke; polycystic ovarian disease; craniopharyngioma; the Prader-Willi Syndrome; Frohlich's syndrome; GH-deficient subjects; normal variant short stature; Turner's syndrome; and other pathological conditions showing reduced metabolic activity or a decrease in resting energy expenditure as a percentage of total fat-free mass, e.g., children with acute lymphoblastic leukemia.

The present invention also comprise treating of obesity and obesity related diseases and disorders by administering a combination of a ghrelin receptor antagonist and a GOAT inhibitor together with an anti-obesity agent, which can be administered separately or concurrently. In other embodiments, several ghrelin receptor antagonists and GOAT inhibitors are used.

Anti-obesity agents to be used in combination with the gherlin receptor antagonists and GOAT inhibitors of the present invention are known to those of skill in the art and can include, but not limited to, a 5HT (serotonin) transporter inhibitor, a NE (norepinephrine) transporter inhibitor, a CB-1 (cannabinoid-1) antagonist/inverse agonist, a H3 (histamine H3) antagonist/inverse agonist, a MCH1R (melanin concentrating hormone 1R) antagonist, a MCH2R agonist/antagonist, a NPY1 antagonist, a leptin, a leptin derivative, a leptin analog, an opioid antagonist, an orexin antagonist, a BRS3 (bombesin receptor subtype 3) agonist, a CCK-A (cholecystokinin-A) agonist, a CNTF (Ciliary neurotrophic factor), a CNTF derivative, a GHS (growth hormone secretagogue receptor) agonist, a 5HT2C (serotonin receptor 2C) agonist, a Mc4r (melanocortin 4 receptor) agonist, a monoamine reuptake inhibitor, an UCP-1 (uncoupling protein-1), 2, or 3 activator, a P3 (beta adrenergic receptor 3) agonist, a thyroid hormone agonist, a PDE (phosphodiesterase) inhibitor, a FAS (fatty acid synthase) inhibitor, a DGAT1 (diacylglycerol acyltransferase) inhibitor, a DGAT2 inhibitor, an ACC2 (acetyl-CoA carboxylase-2) inhibitor, a glucocorticoid antagonist, an acyl-estrogen, a lipase inhibitor, a fatty acid transporter inhibitor, a dicarboxylate transporter inhibitor, a glucose transporter inhibitor, a serotonin reuptake inhibitors, metformin, and topiramate.

The anti-obesity compound to be used in combination with the ghrelin receptor antagonists of the present invention may act via a mechanism other than ghrelin, thus providing for additive anti-obesity effects.

In one embodiment, the ghrelin receptor antagonists and GOAT inhibitors of the present invention is administered prior to taking a meal, for example, 4 hours, 3 hours, 2 hours, 1 hour, or 0.5 hours prior to expected meal time. Preferably, the ghrelin receptor antagonist and GOAT inhibitor are administered 0.5 hours prior to feeding. Alternatively, the ghrelin receptor antagonist and GOAT inhibitor can be administered continuously, for example, systemically, as a single administration every 6, 5, 4, 3, 2, or 1 month, preferably every 3 months. Here, the ghrelin receptor antagonist and GOAT inhibitor of the present invention can normalize an otherwise dysfunctional endocrine system. The compound can be active in the individual for several months.

In another embodiment of the present invention, a method for treating diabetes is encompassed. Diabetes can include both insulin-dependent diabetes mellitus (i.e., IDDM, also known as type I diabetes) and non-insulin-dependent diabetes mellitus (i.e., NIDDM, also known as Type II diabetes). In this method, individuals with or at risk for developing diabetes are administered the ghrelin receptor antagonists and GOAT inhibitors of the present invention alone or in combination with other diabetes treatments known to those of skill in the art.

"Treatment" (of obesity and obesity-related disorders) refers to the administration of the compounds or combinations of the present invention to reduce or maintain the body weight of an obese subject. One outcome of treatment can be reducing the body weight of an obese subject relative to that subject's body weight immediately before the administration of the compounds or combinations of the present invention. Another outcome of treatment can be preventing body weight regain of body weight previously lost as a result of diet, exercise, or pharmacotherapy. Another outcome of treatment can be decreasing the occurrence of and/or the severity of obesity-related diseases. Another outcome of treatment may be to maintain weight loss. The treatment can suitably result in a reduction in food or calorie intake by the subject, including a reduction in total food intake, or a reduction of intake of specific components of the diet such as carbohydrates or fats; and/or the inhibition of nutrient absorption; and/or the inhibition of the reduction of metabolic rate; and in weight reduction in patients in need thereof. The treatment can also result in an alteration of metabolic rate, such as an increase in metabolic rate, rather than or in addition to an inhibition of the reduction of metabolic rate; and/or in minimization of the metabolic resistance that normally results from weight loss.

"Treatment" (of cancer) refers to the administration of the compounds or combinations of the present invention to reduce, eliminate, ameliorate the symptoms brought about directly or indirectly by the cancer, e.g. the symptoms of Cushing disease as a result of excess ACTH from a pituitary tumor or ectopic acromegaly from excess growth hormones from a metastatic bronchial carcinoid tumor.

In one embodiment, the ghrelin receptor antagonists and GOAT inhibitors of the present invention are used to treat or prevent hormonally functional endocrine or non-endocrine tumors.

In one embodiment, the combined used of the ghrelin receptor antagonists and GOAT inhibitors described herein provides a method to decrease or regulate gastrointestinal motility or acidity in a mammal.

In another embodiment, the combined used of the ghrelin receptor antagonists and GOAT inhibitors described herein provide a method of treatment, prevention or management of psychobehavior related to under and over-nutrition such as hunger, satiety and anxiety.

In yet another embodiment, the combined used of the ghrelin receptor antagonists and GOAT inhibitors described herein provides a method for augmenting the actions of desacyl ghrelin by decreasing the action of acyl ghrelin and its receptor.

In another embodiment, the ghrelin receptor antagonists and GOAT inhibitors described herein are administered, in combination, to a subject for the treatment of pituitary tumor, e.g. to inhibit pituitary tumor producing growth hormone.

In another embodiment, the ghrelin receptor antagonists and GOAT inhibitors described herein are administered in conjunction with methods for the treatment of tumors that produce prolactin. Prolactin ("PRL") is a 23-kDa neuroendocrine hormone which is structurally related to growth hormone. Prolactin secretion has been associated with several types of cancer including, but not limited to breast, pituitary and prostrate. Thus, the present invention relates to methods for inhibiting the cell proliferation-promoting effects of prolactin on its receptor. Conditions which can benefit from the administration of both a ghrelin receptor antagonist and a GOAT inhibitor include both benign and malignant proliferation of cells which express a prolactin receptor. Such conditions include but are not limited to proliferative diseases of the breast, including benign conditions such as breast adenomas and fibrocystic disease, and malignant conditions such as breast cancer, including ductal, scirrhous, medullary, colloid and lobular carcinomas (local or metastatic); and proliferative diseases of the prostate, including benign prostatic hypertrophy and prostate cancer (local or metastatic).

Also encompassed are methods for the treatment of metabolic syndrome. The term "metabolic syndrome", also known as syndrome X, is defined in the Third Report of the National Cholesterol Education Program Expert Panel on Detection, Evaluation and Treatment of High Blood Cholesterol in Adults (ATP-III). E. S. Ford et al., JAMA, vol. 287 (3), Jan. 16, 2002, pp 356-359. Briefly, a person is defined as having metabolic syndrome if the person has three or more of the following symptoms: abdominal obesity, hypertriglyceridemia, low HDL cholesterol, high blood pressure, and high fasting plasma glucose. The criteria for these are defined in ATP-III. Metabolic syndrome is obesity related and thus administration of the novel ghrelin receptor antagonists of the present invention are useful in its treatment.

Furthermore, methods for the diagnosis of obesity and obesity related diseases and disorders, including diabetes are encompassed. In this embodiment, the ghrelin receptor antagonist(s) and GOAT inhibitor(s) are administered to a subject and their response is closely analyzed. A decrease in desire for food immediately following administration of the compounds or a decrease in weight gain or a reduction in weight indicates a propensity to or a current affliction with obesity or an obesity related disease or disorder.

In one embodiment, Ghrelin/GHRP/GHS receptor antagonists can be utilized as a diagnostic agent to assess the role of ghrelin, other ghrelin-like molecules, and ghrelin receptor agonists or its receptor in the regulation of GH secretion, food intake, and gastrointestinal motility. The antagonists can also be used to rule out endogenous pathophysiological activities of ghrelin, assess the role of ghrelin in various physiological and metabolic processes, assess the effects of exogenous ghrelin, GHSs as well as other agents that possibly act via release of endogenous ghrelin or via ghrelin mimics, and determine biological actions of acylated ghrelin over that of desacylated ghrelin.

Specifically, in one embodiment diagnostic indicates/reveals a role of ghrelin and/or its receptor(s) in over, under or dysfunctional secretion in the pathophysiology of GH release. In another embodiment, diagnostic indicates/reveals a role of ghrelin and/or its receptor(s) in the pathophysiology of food intake in over or under nutrition. In yet another embodiment, diagnostic indicates/reveals risk of developing obesity, metabolic syndrome, diabetes and/or success rate of anti-obesity therapy. In yet another embodiment, diagnostic indicates/reveals a role of ghrelin and/or its receptor(s) in cognitive-memory and psychobehavior related to under and/or or nutrition such as hunger, satiety and anxiety. In another embodiment, the diagnostic indicates/reveals role of ghrelin and/or its receptor(s) in the pathophysiology of insulin secretion and/or its actions. In another embodiment, the diagnostic indicates/reveals role of ghrelin and its receptor(s) on the pathophysiology of gastrointestinal (GI) motility, acidity or other GI disorders. In yet another embodiment, the diagnostic method indicates/reveals role of ghrelin and its receptor(s) on endothelial dysfunction in particular related to vasoconstriction and/or insulin actions in particular hypertension, diabetes and metabolic syndrome. In another embodiment, the diagnostic method indicates/reveals role and action of ghrelin and its receptor(s) on hepatic gluconeogenesis and body fat as indicated by effects on circulating glucose, insulin, adipokines, leptin, resistin, adiponectin and plasminogen activator inhibitor. In still another embodiment, the diagnostic indicates/reveals/distinguishs the actions of acylated ghrelin and desacylated ghrelin on selective actions of certain GH secretagogues. In another method, the diagnostic method indicates/reveals a role of ghrelin and its receptor(s) on agents that increase (i.e., anti-depressants, glucocorticoids and other drugs that influence food intake). In still another embodiment, the diagnostic method indicates/reveals a role of ghrelin and its receptor(s) in hormonally functional endocrine and non-endocrine tumors.

In another embodiment, the ghrelin receptor antagonists and GOAT inhibitors described herein are administered separately or concurrently to a subject in need thereof.

In one embodiment, provided herein is a method for treatment, prevention or management of obesity in a subject, the method comprising the step of administering an effective amount of a compound having the formula I, wherein the compound is a ghrelin receptor antagonist.

In another embodiment, the method of for treatment, prevention or management of obesity in a subject further comprises an anti-obesity treatment. In another embodiment, the anti-obesity treatment is a combination of dietary restriction therapy with a 5HT (serotonin) transporter inhibitor, a NE (norepinephrine) transporter inhibitor, a CB-1 (cannabinoid-1) antagonist/inverse agonist, a H3 (histamine H3) antagonist/inverse agonist, a MCH1R (melanin concentrating hormone 1R) antagonist, a MCH2R agonist/antagonist, a NPY1 antagonist, leptin, a leptin derivative, a leptin analog, an opioid antagonist, an orexin antagonist, a BRS3 (bombesin receptor subtype 3) agonist, a CCK-A (cholecystokinin-A) agonist, a CNTF (Ciliary neurotrophic factor), a CNTF derivative, a lipase drug inhibitor, an inhibitor of food intake, an incretin, an incretin agonist, an incretin analog or an incretin mimic administered simultaneously, concurrently or sequentially.

In one embodiment, provided herein is a method for treatment, prevention or management of diabetes mellitus in a subject in need thereof, the method comprising the step of administering an effective amount of a compound having the formulae (I)-(VII), wherein the compound is a ghrelin receptor antagonist.

In one embodiment, provided herein is a method for the modulation of ghrelin receptor in a subject in need thereof, the method comprising the step of administering an effective amount of a GOAT inhibitor.

In one embodiment, provided herein is a method for the modulation of ghrelin receptor in a subject in need thereof, the method comprising the step of administering an effective amount of a compound having the formulae (I)-(VII), wherein the compound is a ghrelin receptor antagonist.

In one embodiment, provided herein is a method for treatment, prevention, or management of metabolic syndrome in a subject in need thereof, the method comprising the step of administering an effective amount of a compound having the formulae (I)-(VII), wherein the compound is a ghrelin receptor antagonist.

In one embodiment, provided herein is a method for treatment, prevention, or management of cancer in a subject in need thereof, the method comprising the step of administering an effective amount of a compound having the formulae (I)-(VII), wherein the compound is a ghrelin receptor antagonist.

The present invention can be defined in any of the following numbered paragraphs:

1. A method for treatment, prevention or management of obesity or obesity related diseas or disorder in a subject in need thereof, said method comprising the step of administering an effective amount of a ghrelin O-acyltransferase (GOAT) inhibitor and an effective amount of a ghrelin receptor antagonist.
2. A method for treatment, prevention or management of obesity or obesity related disease or disorder in a subject in need thereof, said method comprising the step of administering an effective amount of a ghrelin O-acyltransferase (GOAT) inhibitor.
3. The method of paragraph 1 or 2, further comprising an anti-obesity treatment.
4. The method of paragraph 3, wherein the anti-obesity treatment is a combination of dietary restriction therapy with a 5HT (serotonin) transporter inhibitor, a NE (norepinephrine) transporter inhibitor, a CB-1 (cannabinoid-1) antagonist/inverse agonist, a H3 (histamine H3) antagonist/inverse agonist, a MCH1R (melanin concentrating hormone 1R) antagonist, a MCH2R agonist/antagonist, a NPY1 antagonist, a leptin, a leptin derivative, a leptin analog, PYY(1-36), PYY(3-36), an opioid antagonist, an orexin antagonist, a BRS3 (bombesin receptor subtype 3) agonist, a CCK-A (cholecystokinin-A) agonist, a CNTF (Ciliary neurotrophic factor), a CNTF derivative, a lipase drug inhibitor, an inhibitor of food intake, an incretin, an incretin agonist, an incretin analog or an incretin mimic administered simultaneously, concurrently or sequentially.
5. The method of paragraph 4, wherein the inhibitor of food intake is glucagon-like-peptide (Glip-1/Glip-2) or oxyntomodulin or their analogs, derivatives, or mimics.
6. The method of paragraph 3, wherein the anti-obesity treatment is bariatric surgery.
7. A method for the modulation of ghrelin receptor in a subject in need thereof, said method comprising the step of administering an effective amount of a ghrelin receptor antagonist.
8. The method paragraph 7, further comprising administering an effective amount of a GOAT inhibitor.
9. A method for treatment, prevention or management of diabetes mellitus in a subject in need thereof, said method comprising the step of administering an effective amount of a GOAT inhibitor and/or an effective amount of a ghrelin receptor antagonist.
10. The method of paragraph 9, wherein the diabetes mellitus is type I or II.
11. A method for treatment, prevention, or management of metabolic syndrome in a subject in need thereof, said method comprising the step of administering an effective amount of a GOAT inhibitor and/or an effective amount of a ghrelin receptor antagonist.
12. The method of any of paragraphs 9-11, wherein the ghrelin receptor antagonist is administered alone, sequentially, or concomitantly with a biguanide, a peroxisome proliferator activator-receptor alpha (PPAR-alpha) ligand or PPAR-gamma ligand.

13. A method for treatment, prevention, or management of cancer in a subject in need thereof, said method comprising the step of administering an effective amount of a GOAT inhibitor and/or an effective amount of a ghrelin receptor antagonist.
14. The method of any of paragraph 1-13, wherein the subject is obese or at risk of obesity.
15. The method of any of paragraphs 1-14, wherein the subject has a body mass index (BMI) of over 25.
16. The method of any of paragraphs 1-15, wherein the subject has a body mass index (BMI) of between 25 and 30.
17. The method of any of paragraphs 1-16, wherein the subject has a body mass index (BMI) of over 30.
18. The method of any of paragraphs 1-17, wherein GH secretion in the subject is inhibited by at least at least 5%, at least 10%, at least 20%, at least 30%, at least 40%, at least 50%, at least 60%, at least 70%, at least 80%, at least 90%, at least 95% or complete inhibition relative to GH secretion before onset of treatment or relative to an untreated control.
19. The method of any of paragraphs 1-18, wherein food intake by the subject is decreased or inhibited by at least 5%, at least 10%, at least 20%, at least 30%, at least 40%, at least 50%, at least 60%, at least 70%, at least 80%, at least 90%, at least 95% or complete inhibition relative to an untreated control.
20. The method of any of paragraphs 1-19, wherein the GOAT inhibitor and/or the ghrelin receptor antagonist comprises an octanoylated peptide and wherein the octanoylation is at position three of the peptide.
21. The method of any of paragraphs 1-19, wherein the GOAT inhibitor and/or the ghrelin receptor antagonist comprises an octanoylated pentapeptide and wherein the octanoylation is at position three of the pentapeptide.
22. The method of any of paragraphs 1-20, wherein the GOAT inhibitor and/or the ghrelin receptor antagonist comprises an octanoylated pentapeptide and wherein the octanoylation is on the side chain of residue at position three of the pentapeptide
23. The method of any of paragraphs 1-21, wherein the octanoylated ghrelin pentapeptide is Gly-Ser-[Ser-Octanoyl$^3$]-Phe-LeuCO$_2$H (SEQ ID NO: 1), Gly-Ser-[Ser-Octanoyl$^3$]-Phe-LeuNH$_2$ (SEQ ID NO: 94), Gly-Ser-[Ser-Octanoyl$^3$]-Phe-Leu-CO$_2$H (SEQ ID NO: 1), Gly-Ser-[Dap-Octanoyl$^3$]-Phe-LeuCO$_2$H (SEQ ID NO: 2), or Gly-Ser-[Dap-Octanoyl$^3$]-Phe-LeuNH$_2$ (SEQ ID NO: 95).
24. The method of any of paragraphs 1-22, wherein the ghrelin receptor antagonist is of formula (I): $A_1$-$A_2$-$A_3$-$A_4$-$A_5$-$A_6$, wherein: $A_1$ os His, Tyr, desamino-Tyr, D- or L-Ala, β-Ala, CyclohexylAla (Cyclohexylalanine), D-Arg, Ava (aminovaleric acid), Gly, <Glu (pyroglutaminic acid), α-Aib (alpha-aminoisobutyric acid), γ-Abu (gamma-aminobutyric acid), α-Abu, α,γ-Abu, D-Val, D-phe, D-Thr, D-Pal (pyridylalanine), D-Lys, AcD-Lys, D-Leu, D-Trp, D,α-naphthylalanine, D,β-naphthylalanine, or Ac-D,β-naphthylalanine; $A_2$ is D-α-naphthylalanine, D-β-naphthylalanine; Ac-D-β-naphthylalanine, D- or L-Trp, D- or L-Phe, Ala, His, PicLys (N$^ε$-picoloyl-lysine), D-Cyclohexylalanine, or an amino acid that is methylated at the terminal nitrogen of the α carbon atom of the $A_2$ residue; $A_3$ is D- or L-Lys, lysine analogs and derivatives, Arg, arginine analogs and derivatives, Orn, Phe, Trp, Leu, Pro, Ala, Ser, Pal, or α,γ-Abu; $A_4$ is D- or L-Trp, D- or L-Phe, Ala, Ser, Tyr, Met, Pro, Thr, ILys, or CyclohexylAla; $A_5$ is D- or L-Trp, D- or L-Phe, Ala, Lys, Arg, Orn, Thr, Leu, or D-CyclohexylAla; $A_6$ is Lys, Arg, Orn, D- or L-Phe, Pro (cyclic Arg-Pro), Nle (norleucine), α,γ-Abu amide, or a free acid carboxyl group; and prodrugs, metabolite, or pharmaceutically acceptable salts thereof.

25. The method of any of paragraphs 1-23, wherein the ghrelin receptor antagonist is of formula (II): $A_7$-$A_8$-$A_9$-$A_{10}$, wherein: $A_7$ is D-α-Nal, D-β-Nal, Ac-D-β-Nal, Ac-D-α-Nal, D- or L-Tyr, Ac-D-Tyr, Lys, D-Phe, His, α-Abu, α,γ-Abu, γ-Abu, DcyclohexylAla, or isonipecotic carboxylic acid (inip); Ag is D- or L-Trp, Ala, His, Phe, or Leu; $A_9$ is D- or L-Trp, Ala, CyclohexylAla, Phe, Pro, Lys, Sarcosine (Sar, N-methylglycine), or a free acid carboxyl group; $A_{10}$ is D- or L-Arg, Phe, CyclohexylAla, Lys, Ser, NMePhe, DPal, Aib, or Orn; and prodrugs, metabolite, or pharmaceutically acceptable salts thereof.
26. The method of any of paragraphs 1-23, wherein the ghrelin receptor antagonist is of formula (III):

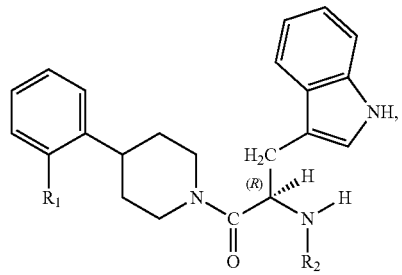

Formula (III)

wherein:
$R_1$ is OH; $R_2$ is H, —C(O)—(CH$_2$)$_3$—NH$_2$, —C(O)—C(CH$_3$)$_2$—NH$_2$, —C(O)—CH((CH$_2$)$_4$—NHR$_5$)—NH—C(O)—CH(NHR$_3$)CH$_2$OR$_4$; $R_3$ is H, —C(O)-phenyl, or —C(O)CH$_3$; $R_4$ is H, or —CH$_2$-phenyl; $R_5$ is H, or —C(O)CH$_3$; and isomers, derivatives, prodrugs, metabolite, or pharmaceutically acceptable salts thereof.

27. The method of any of paragraphs 1-23, wherein the ghrelin receptor antagonist is of formula (IV):

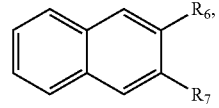

Formula (IV)

wherein:
$R_6$ is —C(O)OCH$_2$CH$_3$, —C(O)OCH$_3$,

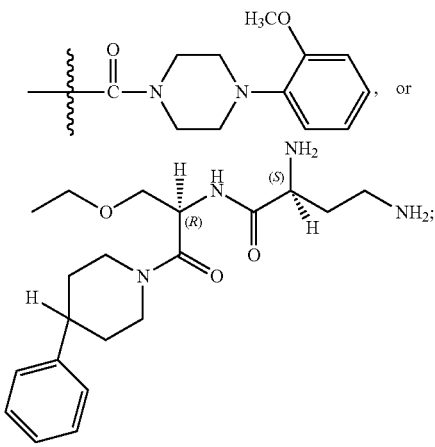

, or

R$_7$ is —H,

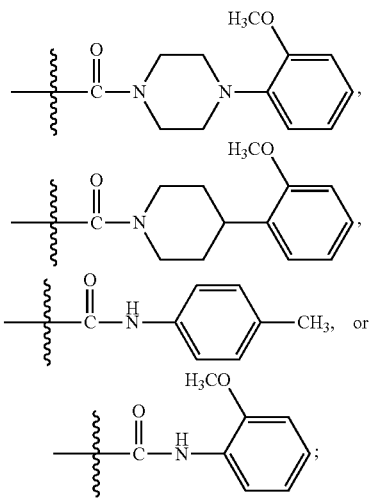

and isomers, derivatives, prodrugs, metabolite, or pharmaceutically acceptable salts thereof.

28. The method of any of paragraphs 1-23, wherein the ghrelin receptor antagonist is of formula (V):

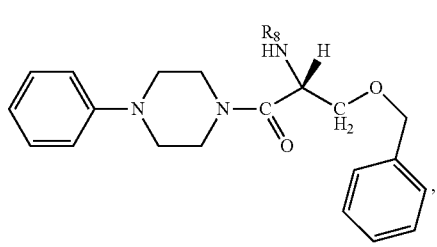

Formula (V)

wherein:
R$_8$ is H, or —C(O)C(CH$_3$)$_2$—NH$_2$; and isomers, derivatives, prodrugs, metabolite, or pharmaceutically acceptable salts thereof.

29. The method of any of paragraphs 1-23, wherein the ghrelin receptor antagonist is of formula (VI): S$^1$B$^1$S$^2$B$^2$S$^3$, wherein: S$^1$ is H, CO$_2$H, R$^{11}$R$^{12}$, or R$^{11}$R$^{12}$R$^{13}$; S$^2$ is des-Amino, H, CO$_2$H, R$^{11}$, R$^{11}$R$^{12}$, or R$^{11}$R$^{12}$R$^{13}$; S$^3$ is H, CO$_2$H, NH$_2$, R$^{11}$, R$^{11}$R$^{12}$, or R$^{11}$R$^{12}$R$^{13}$; R$^{11}$, R$^{12}$, and R$^{13}$ are selected from the group consisting of L-amino acids, Pal (3-pyridyl alanine), cyclo-Ala, Aib, Nle, inip, Abu, βNal, αNal, Orn, carboxylic acid, and their respective D isomers, and can be the same or different; B$^1$ is selected from the group consisting of Trp, βNal, αNal, Leu, Lys, cyclohexylAla, and their respective D isomers; B$^2$ is any natural L-amino acid, Pal (3-pyridyl alanine), cycloAla, Aib, Nle, inip, Abu, βNal, αNal, Orn, and their respective D isomers; and isomers, derivatives, prodrugs, metabolite, or pharmaceutically acceptable salts thereof.

30. The method of any of paragraphs 1-23, wherein the ghrelin receptor antagonist is of formula (VII): A$^{11}$-A$^{12}$-A$^{13}$-Gly-Ser-A$^{14}$-Phe-Leu-A$^{15}$-A$^{16}$-A$^{17}$-A$^{18}$ (SEQ ID NO: 93), wherein each of A$^{11}$, A$^{12}$, and A$^{13}$ is absent, an amino acid or an amino protecting group, and can be the same or different; each of A$^{15}$, A$^{16}$, A$^{17}$, and A$^{18}$ is absent or an amino acid, and can be the same or different; A$^{14}$ is a serine conjugated with a —C(O)C$_1$-C$_{20}$ alky group on the side chain OH of said serine or a diaminopropionic acid conjugated with a —C(O)C$_1$-C$_{20}$ alky group on one of the amino group diaminopropionic acid, provided at least one of A$^{11}$, A$^{12}$, or A$^{13}$ is present.

31. The method of paragraph 30, wherein the amino acid is selected from the group consisting of alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, valine, homocysteine, phosphoserine, phosphothreonine, phosphotyrosine, hydroxyproline, gamma-carboxyglutamate; hippuric acid, octahydroindole-2-carboxylic acid, statine, 1,2,3,4,-tetrahydroisoquinoline-3-carboxylic acid, penicillamine (3-mercapto-D-valine), ornithine, citruline, alpha-methyl-alanine, para-benzoylphenylalanine, para-aminophenylalanine, p-fluorophenylalanine, phenylglycine, propargylglycine, sarcosine, and tert-butylglycine), diaminobutyric acid, 7-hydroxy-tetrahydroisoquinoline carboxylic acid, naphthylalanine, biphenylalanine, cyclohexylalanine, amino-isobutyric acid, norvaline, norleucine, tert-leucine, tetrahydroisoquinoline carboxylic acid, pipecolic acid, phenylglycine, homophenylalanine, cyclohexylglycine, dehydroleucine, 2,2-diethylglycine, 1-amino-1-cyclopentanecarboxylic acid, 1-amino-1-cyclohexanecarboxylic acid, amino-benzoic acid, amino-naphthoic acid, gamma-aminobutyric acid, difluorophenylalanine, nipecotic acid, alpha-amino butyric acid, thienyl-alanine, t-butylglycine, desamino-Tyr, aminovaleric acid, pyroglutaminic acid, alpha-aminoisobutyric acid, gamma-aminobutyric acid, alpha-aminobutyric acid, alpha,gamma-aminobutyric acid, pyridylalanine, α-naphthylalanine, β-naphthylalanine, Ac-β-naphthylalanine, N$^\epsilon$-picoloyl-lysine, 4-halo-Phenyl, 4-pyrolidylalanine, isonipecotic carboxylic acid, and analogs, derivatives, and isomers thereof.

32. The method of any of paragraphs 1-31, wherein the ghrelin receptor antagonist is selected from the group consisting of Tyr-DTrp-DLys-Trp-DPhe-NH$_2$ (SEQ ID NO: 11), Tyr-DTrp-Lys-Trp-DPhe-NH$_2$ (SEQ ID NO: 12), His-DTrp-DLys-Trp-DPhe-NH$_2$ (SEQ ID NO: 13), His-DTrp-DLys-Phe-DTrp-NH$_2$ (SEQ ID NO: 14), His-DTrp-DArg-Trp-DPhe-NH$_2$ (SEQ ID NO: 15), His-DTrp-DLys-Trp-DPhe-Lys-NH$_2$ (SEQ ID NO: 16), DesaminoTyr-DTrp-Ala-Trp-DPhe-NH$_2$ (SEQ ID NO: 17), DesaminoTyr-DTrp-DLys-Trp-DPhe-NH$_2$ (SEQ ID NO: 18), DeaminoTyr-DTrp-Ser-Trp-DPhe-Lys-NH$_2$ (SEQ ID NO: 19), DesaminoTyr-DTrp-Ser-Trp-DPhe-NH$_2$ (SEQ ID NO: 20), His-DTrp-DTrp-Phe-Met-NH$_2$ (SEQ ID NO: 21), Tyr-DTrp-DTrp-Phe-Phe-NH$_2$ (SEQ ID NO: 22), Glyψ[CH$_2$NH]-DβNal-Ala-Trp-DPhe-Lys-NH$_2$ (SEQ ID NO: 23), Glyψ[CH2NH]-DβNal-DLys-Trp-DPhe-Lys-NH$_2$ (SEQ ID NO: 24), DAla-DβNal-DLys-DTrp-Phe-Lys-NH$_2$ (SEQ ID NO: 25), His-DβNal-DLys-Trp-DPhe-Lys-NH$_2$ (SEQ ID NO: 26), Ala-His-DTrp-DLys-Trp-DPhe-Lys-NH$_2$ (SEQ ID NO: 27), Alaψ[CH2NH]-DβNal-Ala-Trp-DPhe-Lys-NH$_2$ (SEQ ID NO: 28), DβNal-Ala-Trp-DPhe-Ala-NH$_2$ (SEQ ID NO: 29), DAla-DcyclohexylAla-Ala-Phe-DPhe-Nle-NH$_2$ (SEQ ID NO: 30), DcyclohexylAla-Ala-Phe-DTrp-Lys-NH$_2$ (SEQ ID NO: 31), DAla-DβNal-Ala-Thr-DThr-Lys-NH$_2$ (SEQ ID NO: 32), DcyclohexylAla-Ala-Trp-DPhe-NH$_2$ (SEQ ID NO: 33), DAla-DβNal-Ala-Ala-DAla-Lys-NH$_2$ (SEQ ID NO: 34), DβNal-Ala-Trp-DPhe-Leu-NH$_2$ (SEQ ID NO: 35), His-DTrp-Phe-Trp-DPhe-Lys-NH$_2$ (SEQ ID NO: 36), DAla-DβNal-DAla-DTrp-Phe-Lys-NH$_2$ (SEQ ID NO: 37), βAla-Trp-DAla-DTrp-Phe-NH$_2$ (SEQ ID NO: 38), His-Trp-DAla-DTrp-Phe-LysNH$_2$ (SEQ ID NO: 39), DLys-DβNal-Ala-Trp-DPhe-Lys-NH₂ (SEQ ID NO: 40), DAla-DβNal-DLys-DTrp-Phe-Lys-NH₂ (SEQ ID NO: 41), Tyr-DAla-Phe-Aib-NH₂ (SEQ ID NO: 42), Tyr-DAla-Sar-NMePhe-NH₂ (SEQ ID NO: 43), αγAbu-DTrp-DTrp-Ser-NH₂ (SEQ ID NO: 44), αγAbu-DTrp-DTrp-Lys-NH₂ (SEQ ID NO: 45), αγAbu-DTrp-DTrp-Orn-NH₂ (SEQ ID NO: 46), αAbu-DTrp-DTrp-Orn-NH₂ (SEQ ID NO: 47), DThr-DαNal-DTrp-DPro-Arg-NH₂ (SEQ ID NO: 48), DAla-Ala-DAla-DTrp-Phe-Lys-NH₂ (SEQ ID NO: 49), Alaψ[CH₂NH]His-DTrp-Ala-Trp-DPhe-Lys-NH₂ (SEQ ID NO: 50), Lys-DHis-DTrp-Phe-NH₂ (SEQ ID NO: 51), γAbu-DTrp-DTrp-Orn-NH₂ (SEQ ID NO: 52), inip-Trp-Trp-Phe-NH₂ (SEQ ID NO: 53), Ac-DTrp-Phe-DTrp-Leu-NH₂ (SEQ ID NO: 54), Ac-DTrp-Phe-DTrp-Lys-NH₂ (SEQ ID NO: 55), Ac-DTrp-DTrp-Lys-NH₂ (SEQ ID NO: 56), DLys-Tyr-DTrp-DTrp-Phe-Lys-NH₂ (SEQ ID NO: 57), Ac-DβNal-Leu-Pro-NH₂ (SEQ ID NO: 58), βAla-Trp-DTrp-DTrp-Orn-NH₂ (SEQ ID NO: 59), DVal-Dα-Nal-DTrp-Phe-Arg-NH₂ (SEQ ID NO: 60), DLeu-DαNal-DTrp-Phe-Arg-NH₂ (SEQ ID NO: 61), CyclohexylAla-DαNal-DTrp-Phe-Arg-NH₂ (SEQ ID NO: 62), DTrp-DαNal-DTrp-Phe-Arg-NH₂ (SEQ ID NO: 63), DAla-DβNal-DPro-Phe-Arg-NH₂ (SEQ ID NO: 64), Ac-DαNal-DTrp-Phe-Arg-NH₂ (SEQ ID NO: 65), DαNal-DTrp-Phe-Arg-NH₂ (SEQ ID NO: 66), His-DTrp-DTrp-Lys-NH₂ (SEQ ID NO: 67), Ac-DβNal-DTrp-NH₂ (SEQ ID NO: 68), αAib-DTrp-DcyclohexylAla-NH₂ (SEQ ID NO: 69), αAib-DTrp-DAla-cyclohexylAla-NH₂ (SEQ ID NO: 70), DAla-DcyclohexylAla-Ala-Ala-Phe-DPhe-Nle-NH₂ (SEQ ID NO: 71), DPhe-Ala-Phe-DPal-NH₂ (SEQ ID NO: 72), DPhe-Ala-Phe-DPhe-Lys-NH₂ (SEQ ID NO: 73), DLys-Tyr-DTrp-DTrp-Phe-NH₂ (SEQ ID NO: 74), Ac-DLys-Tyr-DTrp-DTrp-Phe-NH₂ (SEQ ID NO: 75), Arg-DTrp-Leu-Tyr-Trp-Pro(cyclic Arg-Pro) (SEQ ID NO: 76), Ac-DβNal-PicLys-ILys-DPhe-NH₂ (SEQ ID NO: 77), DPal-Phe-DTrp-Phe-Met-NH₂ (SEQ ID NO: 78), DPhe-Trp-DPhe-Phe-Met-NH₂ (SEQ ID NO: 79), DPal-Trp-DPhe-Phe-Met-NH₂ (SEQ ID NO: 80), βAla-Pal-DTrp-DTrp-Orn-NH₂ (SEQ ID NO: 81), αγAbu-Trp-DTrp-DTrp-Orn-NH₂ (SEQ ID NO: 82), βAla-Trp-DTrp-DTrp-Lys-NH₂ (SEQ ID NO: 83), γAbu-Trp-DTrp-DTrp-Orn-NH₂ (SEQ ID NO: 84), Ava-Trp-DTrp-DTrp-Orn-NH₂ (SEQ ID NO: 85), DLys-Tyr-DTrp-Ala-Trp-DPhe-NH₂ (SEQ ID NO: 86), His-DTrp-DArg-Trp-DPhe-NH₂ (SEQ ID NO: 87), <Glu-His-Trp-DSer-DArg-NH₂ (SEQ ID NO: 88), DPhe-DPhe-DTrp-Met-DLys-NH₂ (SEQ ID NO: 89), Gly-Met-Ala-Gly-Ser-(Dap-Oct)-Phe-Leu-Ser-Pro-Glu-His-NH₂ (SEQ ID NO: 3), O-(2-methylallyl)benzophonone oxime, (R)-2-amino-3-(1H-indol-3-yl)-1-(4-phenylpiperidin-1-yl)propan-1-one, N—((R)-1-((R)-1-((S)-3-(1H-indol-3-yl)-1-oxo-1-(4-phenylpiperidin-1-yl)propan-2-ylamino)-6-amino-1-oxohexan-2-ylamino)-3-hydroxy-1-oxopropan-2-yl)benzamide, (S)—N—((S)-3-(1H-indol-3-yl)-1-oxo-1-(4-phenylpiperidin-1-yl)propan-2-yl)-6-acetamido-2-((S)-2-amino-3-(benzyloxy)propanamido)hexanamide, (S)—N—((R)-3-(1H-indol-3-yl)-1-oxo-1-(4-phenylpiperidin-1-yl)propan-2-yl)-2-4S)-2-acetamido-3-(benzyloxy)propanamido)-6-aminohexanamide, (R)—N-(3-(1H-indol-3-yl)-1-(4-(2-methoxyphenyl)piperidin-1-yl)-1-oxopropan-2-yl)-4-aminobutanamide, (R)—N-(3-(1H-indol-3-yl)-1-(4-(2-methoxyphenyl)piperidin-1-yl)-1-oxopropan-2-yl)-2-amino-2-methylpropanamide, methyl 3-(p-tolylcarbamoyl)-2-naphthoate, ethyl 3-(4-(2-methoxyphenyl)piperidine-1-carbonyl)-2-naphthoate, 3-(2-methoxyphenylcarbamoyl)-2-naphthoate, (S)-2,4-diamino-N—((R)-3-(naphthalen-2-ylmethoxy)-1-oxo-1-(4-phenylpiperidin-1-yl)propan-2-yl)butanamide, naphthalene-2,3-diylbis((4-(2-methoxyphenyl)piperazin-1-yl)methanone), (R)-2-amino-N-(3-(benzyloxy)-1-oxo-1-(4-phenylpiperazin-1-yl)propan-2-yl)-2-methylpropanamide, or (R)-2-amino-3-(benzyloxy)-1-(4-phenylpiperazin-1-yl)propan-1-one, and pharmaceutically acceptable salts, prodrugs, or active metabolites thereof.

33. The method of any of paragraphs 1-32, wherein the subject is a mammal.
34. The method of any of paragraphs 1-33, wherein the subject is non-human.
35. The method of any of paragraphs 1-34, wherein the subject is a mouse or rat.
36. The method of any of paragraphs 1-32, wherein the subject is human.
37. The method of any of paragraphs 1-35, wherein the GOAT inhibitor and/or the ghrelin receptor antagonist is formulated in a pharmaceutically acceptable formulation, wherein the formulation comprises a pharmaceutically acceptable carrier.
38. The method paragraph 35, wherein the formulation is a sustained release formulation.
39. The method of any of paragraphs 1-36, wherein said administration is oral, parenteral, intravenous, intramuscular, subcutaneous, transdermal, airway, pulmonary, nasal, rectal, buccal, sublingual, or depot.
40. The method of any of paragraphs 1-38, wherein the GOAT inhibitor and/or the ghrelin receptor antagonist is delivered continuously to the subject.
41. The method of any of paragraphs 1-38, wherein the GOAT inhibitor and/or the ghrelin receptor antagonist is delivered intermittently to the subject
42. A peptide comprising the amino acid sequence of formula (VII): $A^{11}$-$A^{12}$-$A^{13}$-Gly-Ser-$A^{14}$-Phe-Leu-$A^{15}$-$A^{16}$-$A^{17}$-$A^{18}$ (SEQ ID NO: 93), wherein each of $A^{11}$, $A^{12}$, and $A^{13}$, is absent, an amino acid, or an amino protecting group, and can be the same or different; each of $A^{15}$, $A^{16}$, $A^{17}$, and $A^{18}$ is absent or an amino acid, and can be the same or different; $A^{14}$ is a serine conjugated with a —C(O)C₁-C₂₀ alky group on the side chain OH of said serine or a diaminopropionic acid conjugated with a —C(O)C₁-C₂₀alky group on one of the amino group diaminopropionic acid, provided at least one of $A^{11}$, $A^{12}$, or $A^{13}$ is present.
43. The peptide of paragraph 41, wherein the peptide is a GOAT inhibitor and/or a ghrelin receptor antagonist.
44. The peptide of any of paragraphs 41-42, wherein the amino acid is selected from the group consisting of alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, valine, homocysteine, phosphoserine, phosphothreonine, phosphotyrosine, hydroxyproline, gamma-carboxyglutamate; hippuric acid, octahydroindole-2-carboxylic acid, statine, 1,2,3,4,-tetrahydroisoquinoline-3-carboxylic acid, penicillamine (3-mercapto-D-valine), ornithine, citruline, alpha-methylalanine, para-benzoylphenylalanine, para-aminophenylalanine, p-fluorophenylalanine, phenylglycine, propargylglycine, sarcosine, and tert-butylglycine), diaminobutyric acid, 7-hydroxy-tetrahydroisoquinoline carboxylic acid, naphthylalanine, biphenylalanine, cyclohexylalanine, amino-isobutyric acid, norvaline, norleucine, tert-leucine, tetrahydroisoquinoline carboxylic acid, pipecolic acid, phenylglycine, homophenylalanine, cyclohexylglycine, dehydroleucine, 2,2-diethylglycine, 1-amino-1-cyclopentanecarboxylic acid, 1-amino-1-cyclohexanecarboxylic acid, amino-benzoic acid, amino-naphthoic acid, gamma-aminobutyric acid, difluorophenylalanine, nipecotic acid, alpha-amino butyric acid, thienyl-alanine, t-butylglycine, desamino-Tyr, aminovaleric acid, pyroglutaminic acid, alpha-aminoisobutyric acid, gamma-aminobutyric acid, alpha-aminobutyric acid, alpha,gamma-aminobutyric acid, pyridylalanine, α-naphthylalanine, β-naphthylalanine, Ac-βnaphthylalanine, N-$^\epsilon$-picoloyl-lysine, 4-halo-Phenyl, 4-pyrolidylalanine, isonipecotic carboxylic acid, and isomers, analogs and derivatives thereof.

45. The peptide of any of paragraphs 41-43, wherein the alkyl is a $C_1$-$C_{16}$alkyl.
46. The peptide of any of paragraphs 41-44, wherein $A^5$ is an octanoylated serine or an octyanolyatd diaminopropionic acid.
47. The peptide of any of paragraphs 41-45, wherein the peptide comprises at D-amino acid.
48. The peptide of any of paragraphs 41-46, wherein the peptide comprises at least one beta-amino acid.
49. The peptide of any of paragraphs 41-47, wherein the peptide comprises at least one peptide bond replaced by a linkage selected from the group consisting of reduced psi peptide bond, urea, thiourea, carbamate, sulfonyl urea, trifluoroethylamine, ortho-(aminoalkyl)-phenylacetic acid, para-(aminoalkyl)-phenylacetic acid, meta-(aminoalkyl)-phenylacetic acid, thioamide, tetrazole, boronic ester, and olefinic group.
50. The peptide of any of paragraphs 41-48, wherein the peptide is Gly-Met-Ala-Gly-Ser-(Dap-Oct)-Phe-Leu-Ser-Pro-Glu-His-$NH_2$ (SEQ ID NO: 3).

Unless otherwise defined herein, scientific and technical terms used in connection with the present application shall have the meanings that are commonly understood by those of ordinary skill in the art.

It should be understood that this invention is not limited to the particular methodology, protocols, and reagents, etc., described herein and as such may vary. The terminology used herein is for the purpose of describing particular embodiments only, and is not intended to limit the scope of the present invention, which is defined solely by the claims.

It should be understood that this invention is not limited to the particular methodology, protocols, and reagents, etc., described herein and as such may vary. The terminology used herein is for the purpose of describing particular embodiments only, and is not intended to limit the scope of the present invention, which is defined solely by the claims.

Other than in the operating examples, or where otherwise indicated, all numbers expressing quantities of ingredients or reaction conditions used herein should be understood as modified in all instances by the term "about." The term "about" when used in connection with percentages may mean±1%.

The invention is further illustrated by the following examples which should not be construed as limiting. The contents of all references cited throughout this application, including the U.S. provisional application Ser. No. 60/795,960 filed Apr. 28, 2006 as well as the figures and tables are incorporated herein by reference.

EXAMPLES

Animals and Experimental Procedures

Adult male Sprague Dawley rats (225-260 g) were purchased from Charles River Canada (St. Constant, Canada) and individually housed on a 12-h light, 12-h dark cycle (lights on, 0600-1800 h) in a temperature (22±1° C.)- and humidity-controlled room. Purina rat chow (Ralston Purina Co., St. Louis, Mo.) and tap water were available ad libitum.

Chronic intracerebroventricular (i.c.v.) and intracardiac venous cannulas were implanted under sodium pentobarbital (50 mg/kg, i.p.) anesthesia using previously described techniques in (2) and (11). The placement of the icy cannulae was verified by both a positive drinking response to i.c.v. carbachol (100 ng/10 μl) injection on the day after surgery and methylene blue dye at the time of death. After surgery, the rats were placed directly in isolation test chambers with food and $H_2O$ freely available until body weight returned to preoperative levels (usually within 5-7 d). During this time the rats were handled daily to minimize any stress associated with handling on the day of the experiment. On the test day, food was removed 1.5 h before the start of sampling and was returned at the end.

The efficacy of GHS-A to antagonize ghrelin's stimulatory action on GH at both central and peripheral sites was examined. For the central experiments, free-moving rats were i.c.v. injected with either normal saline or GHS-A (5 μg) at 1045 h and, 15 min later (at 1100 h), were subsequently administered ghrelin i.c.v. (500 ng). Both the human ghrelin peptide (provided by Dr. K. Chang, Phoenix Pharmaceuticals, Inc., Belmont, Calif.) and the GHS-A were diluted in normal saline just before use. Blood samples (0.35 ml) were withdrawn every 15 min over a 6-h sampling period (1000-1600 h) from all animals. To document the rapidity of the GH response to ghrelin, an additional blood sample was obtained 5 min after injection of ghrelin. All blood samples were immediately centrifuged, and plasma was separated and stored at −20° C. for subsequent assay of GH. To avoid hemodynamic disturbance, the red blood cells were resuspended in normal saline and returned to the animal after removal of the next blood sample.

For the peripheral experiments, free-moving rats were iv injected with either normal saline or GHS-A (250 μg) at 1045 h and subsequently with ghrelin i.v. (5 μg) at 1100 h. Blood samples were withdrawn from 1000-1600 h, as described above.

For the study designed to assess the involvement of endogenous ghrelin in the genesis of pulsatile GH secretion, free-moving animals were i.c.v.-injected with either normal saline or GHS-A (5 μg) at two different times in the 6-h sampling period: 1045 h and 1345 h. These time points were chosen because they correspond closely to the time of onset of the spontaneous GH secretory episodes, as previously documented in our laboratory (2, 4). Blood samples were withdrawn from 1000-1600 h, as described above; however, no blood sample was withdrawn 5 min after the injections.

The effects of the GHS-A on both spontaneous and ghrelin-induced food intake and body weight gain were investigated. For the spontaneous experiments, the rats were fasted overnight (1600-1100 h next morning) and were i.c.v.-injected with either normal saline or GHS-A (5 μg) at 1100 h. Food intake was monitored on an hourly basis for 5 h after the initial injection (until 1600 h) and subsequently overnight (1600-0900 h next morning). A measured amount of rat chow pellets was placed in the cage every hour. Spillage was collected by placement of a diaper under the rat cages, and total food consumed for each period was calculated by subtracting uneaten food plus spillage from total given. Body weights were recorded daily at 0900 h. The latency to the onset of the first meal after the injection and the duration of that meal were also monitored.

To examine the effect of GHS-A on ghrelin-stimulated food intake, animals were icy injected with either normal saline or GHS-A (5 μg) at 1045 h and subsequently with ghrelin (500 ng) at 1100 h. Food intake was monitored on an hourly basis as described above. In this experiment, food was removed 1.5 h before the start of the test.

All animal-based procedures were approved by the McGill University Animal Care Committee.

Receptor Binding and Calcium Mobilization Studies

The human ghrelin receptor type 1a (GHS-R1a) was expressed in HEK-293 cells, whose cell membranes were subsequently harvested and used in the binding assay. The receptor concentration (Bmax) used in the assay was 2.3 pmol/mg of protein, resulting in a Kd for ghrelin binding of 0.016 nM. The ability of the antagonist to displace 0.009 nM radiolabelled ghrelin was then tested, at a concentration range of 0.1 nM to 10 µM. The binding affinities (Ki) for ghrelin, GHRP-6 and hexarelin in this system were 0.016 nM, 0.58 nM and 0.59 nM respectively.

The ability of the antagonist to mobilize calcium or to inhibit ghrelin-stimulated calcium mobilization was examined using Euroscreen's AequoScreen platform. This method is based on the co-expression in recombinant cell lines of the GHS-R1a and aequorin, a photoprotein capable of detecting calcium concentrations in the lower micromolar range. The agonistic properties of GHS-A were tested at a concentration range of 1 nM to 3 µM, and its capacity to inhibit the calcium mobilized by 22.15 nM ghrelin was tested at a concentration range of 1 nM to 1.5 µM. In this system, ghrelin was found to have an EC50 of 9.33 nM, EC80 of 22.15 nM, and induced maximal activation at a concentration of 100 nM.

The peptides were synthesized by the solid phase method and purified by HPLC. GH was determined by Radioimmunoassay (RIA).

The In Vitro Cell Culture Method

In vitro GH Release-Female rats of the CD-1 strain were housed in a constant temperature room at 24° C. with 14 h light and 10 h darkness. The rats were fed Purina Rat chow and water at libitum. All studies were started between 0800-1000 hours. Pituitaries of mature female Sprague Dawley rats were rapidly removed after decapitation, neurointermediate lobe discarded and then placed in a pH 7.4 buffer. The pituitaries were cut into ~3-mm pieces and then transferred to a flask containing HEPS buffer with trypsin and incubated at 37° C. Cells were triturated several times during this period. After dispersion, the cells were collected by centrifugation, wash with DMEM and placed into culture well. Cell cultures were maintained for 4 days at 37° with 8% $CO_2$ added to the incubator atmosphere. After 4 days in culture, cells were washed with lactated Ringer's solution adjusted to pH 7.2-7.4 and then vehicle, peptide alone or peptide plus stimulator was added to media. Incubation time was 60-120 minutes after which media was removed from each well for GH determination. The GH RIA reagents were distributed by the NIH. Control data was collected from cell cultures treated with only the corresponding vehicle in the absence of peptide or stimulator. Control stimulated data was collected from cell cultures treated with stimulator alone in the absence of any peptide.

The In Vitro Pituitary Incubation Method

Hormonal activities were obtained from in vitro studies using pituitaries of 20 day old CD-1 strain Sprague Dawley female rats. Two pituitaries were incubated for a total of 4-6 hours. Medium was removed each hour for RIA of GH level and fresh medium was added again. After two one hour pre-incubation periods (P1-P2), the vehicle/peptides were added to two one hour incubations (I3–I4). Peptide activity was calculated as the change in the hormonal level (delta) between I3+I4 and P2. For antagonist activity, the incubation was continued for 2 additional hours (I5–I6) where both the peptide and a stimulator of GH secretion was added and the antagonist activity was calculated as the change in the hormonal level (delta) between I5+I6 and P2. The peptides were assayed in triplicate and the hormone was assayed in duplicate. Each value recorded represents the mean of 6. The GH RIA reagents were distributed by the NIH. Control data was collected from isolated pituitary glands treated with only the corresponding vehicle in the absence of peptide or stimulator. Control stimulated data was collected from isolated pituitary glands treated with stimulator alone in the absence of any peptide.

The In Vivo Assay

For the in vivo assay of GH Release in rat, immature female Sprague Dawley rats were obtained from Charles River from Wilmington, Mass. After arrival they were housed at 25° C. with a 14:10 h light:dark cycle. Water and Purina rat chow were available at libitum. Pups were weaned at 21 days of age.

Immature twenty six day old female Sprague Dawley rats, 3-6 rats per treatment dose, were pretreated with pentobarbital 20 minutes before iv injection of vehicle/peptide or peptide plus stimulator. Injection was made as a 0.1 ml solution. For the non-pentobarbital treated rat assay, peptides were administered iv into the tail vein of conscious rats. All animals were sacrificed by guillotine after iv peptide or vehicle. Trunk blood was collected at +10-15 minutes after decapitation, allowed to clot, centrifuged and serum stored until assayed for GH levels by RIA. The GH RIA reagents were distributed by the NIH. Control data was collected from rats treated with only the corresponding vehicle in the absence of peptide or stimulator. Control stimulated data was collected from rats treated with stimulator alone in the absence of any peptide.

Results

Figure 1B:
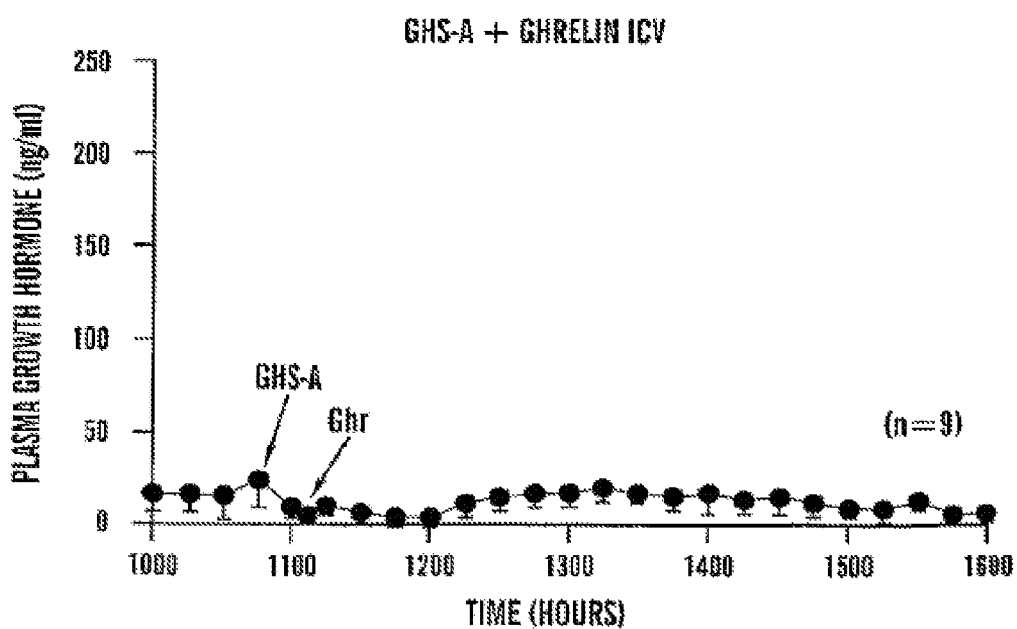
Figure 2A:
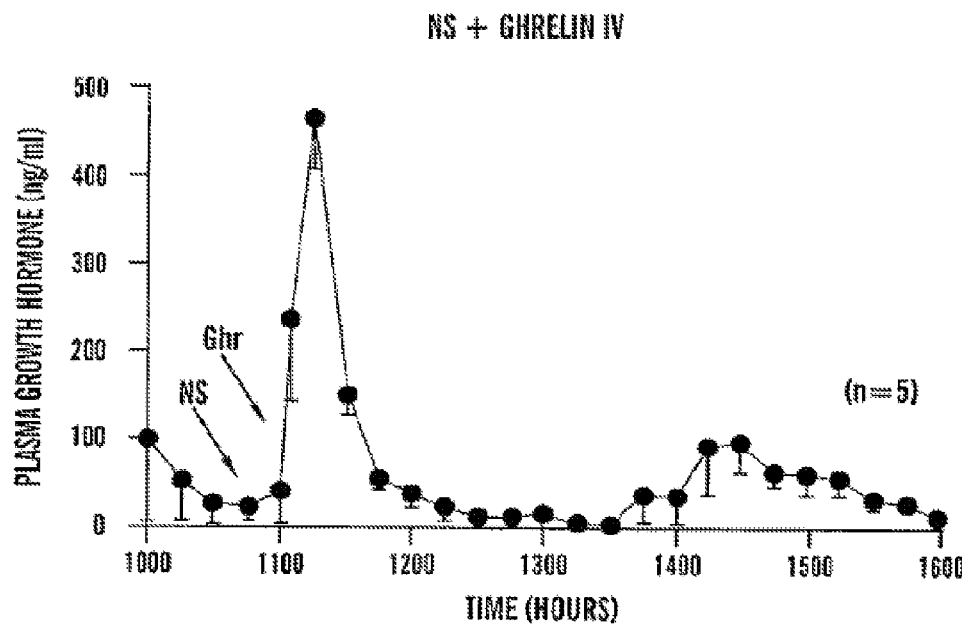
FIGS. 2A and 2B show mean plasma GH responses to 5 μg ghrelin administered iv 15 min after the iv injection of 250 μg GHS-A (FIG. 2B) or normal saline (FIG. 2A). Peripheral administration of GHS-A strongly blocked ghrelin's ability to release GH compared with normal saline-pretreated controls. Values are the mean±SE. The number of animals in each group is shown in parentheses. Arrows indicate the times of i.v. injections.
Figure 2B:
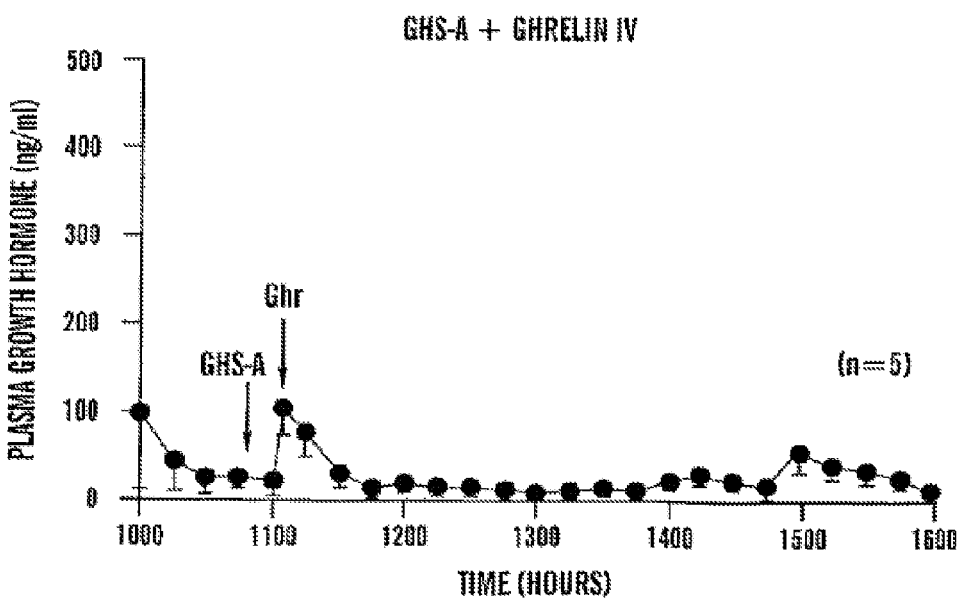
Figure 3:
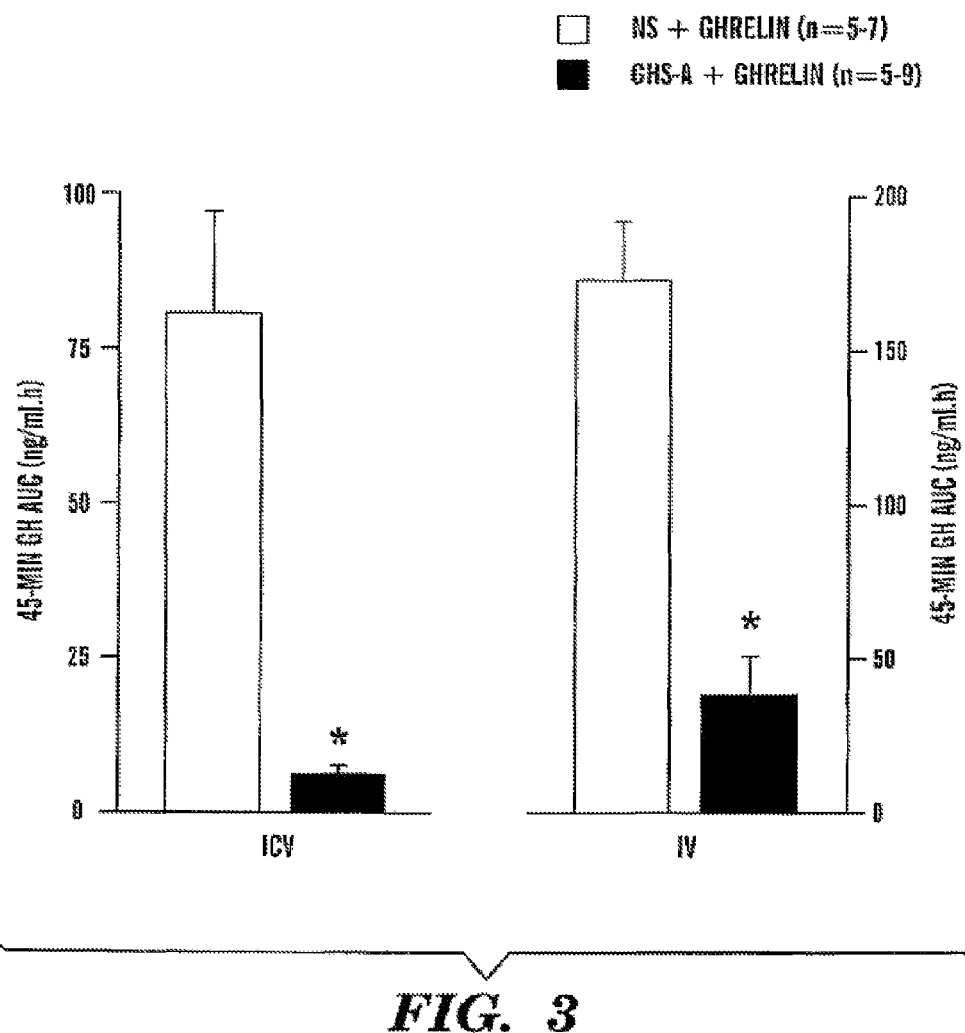
FIG. 3 shows a summary of the effects of GHS-A, given centrally (icy) or peripherally (iv), on ghrelin-induced GH release. The GH AUC following i.c.v. (500 ng) and i.v. (5 μg) ghrelin injection was reduced by 15- and 5-fold, respectively, in the GHS-A pretreated groups compared with their respective normal saline-treated controls. Each bar represents the mean±SE. *, P<0.0003 or less compared with normal saline-pretreated animals.
Figure 4A:
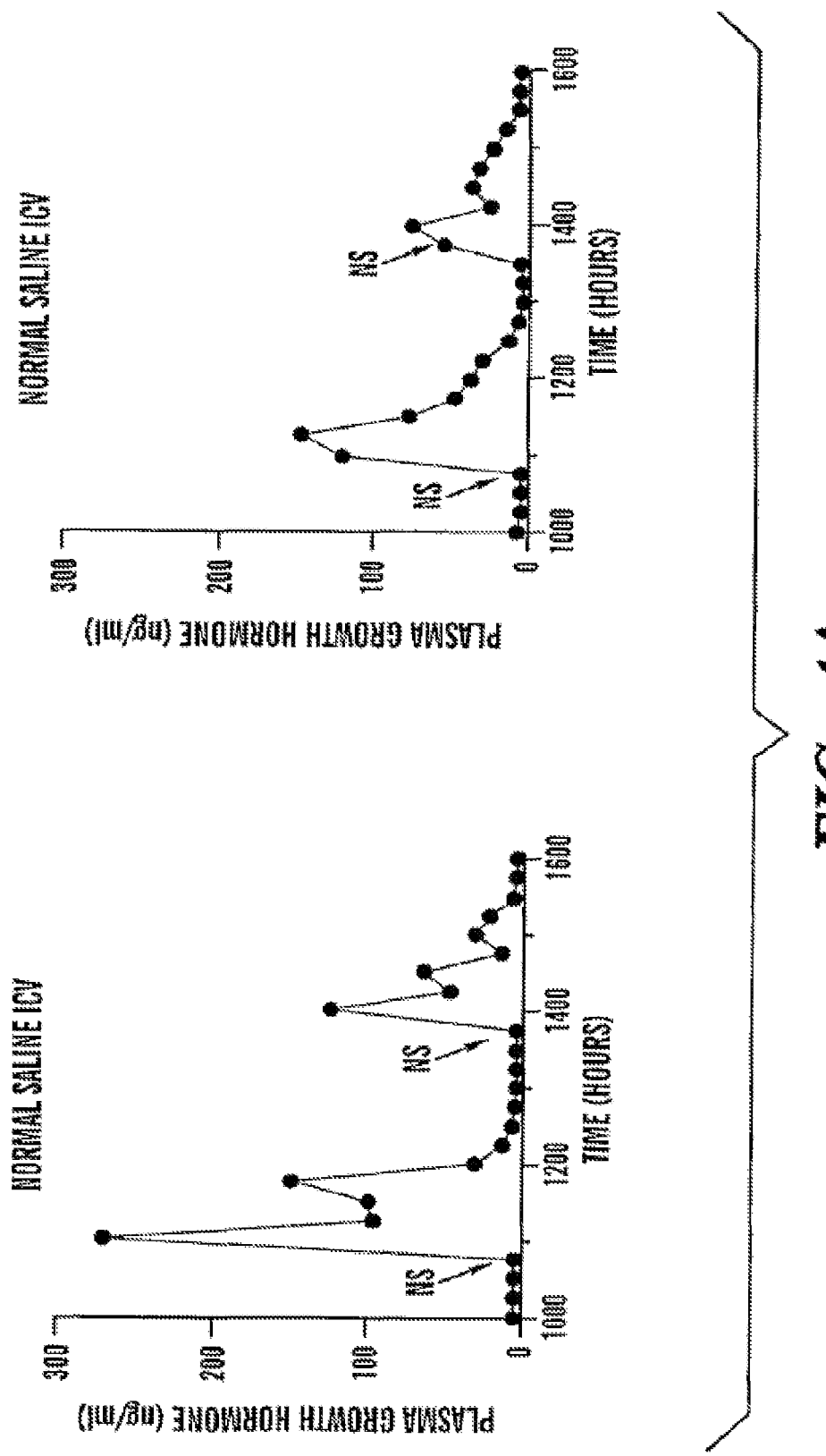
FIGS. 4A and 4B show that Individual representative plasma GH profiles in rats i.c.v. administered either 5 μg GHS-A (FIG. 4B) or normal saline (FIG. 4A) 15 min prior to the expected onset of the spontaneous GH secretory bursts typical of the male rat. GHS-A administration severely attenuated the amplitude of the spontaneous GH pulses compared with normal saline icy-injected controls. Arrows indicate the times of i.c.v. injections.
Figure 4B:
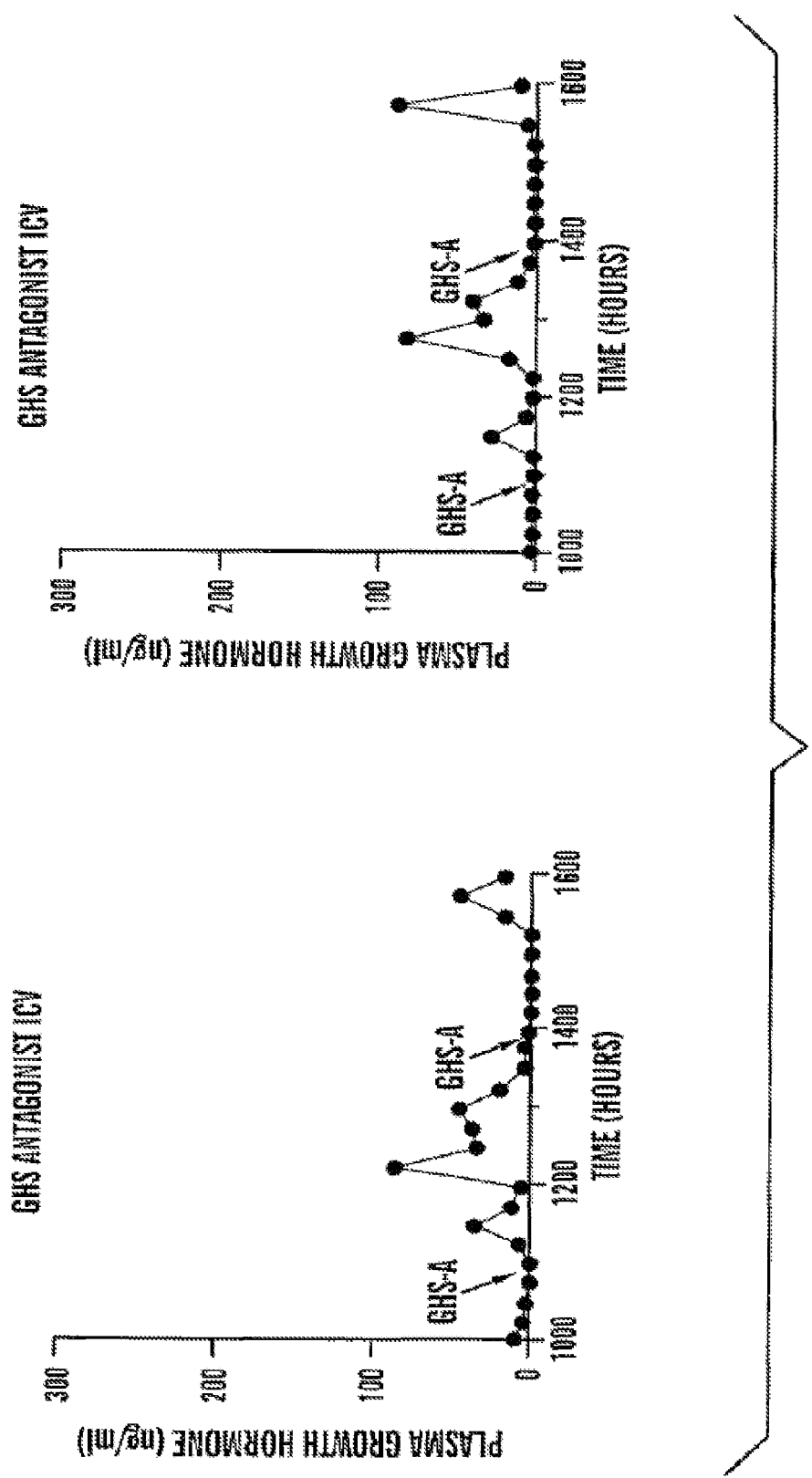
Figure 5:
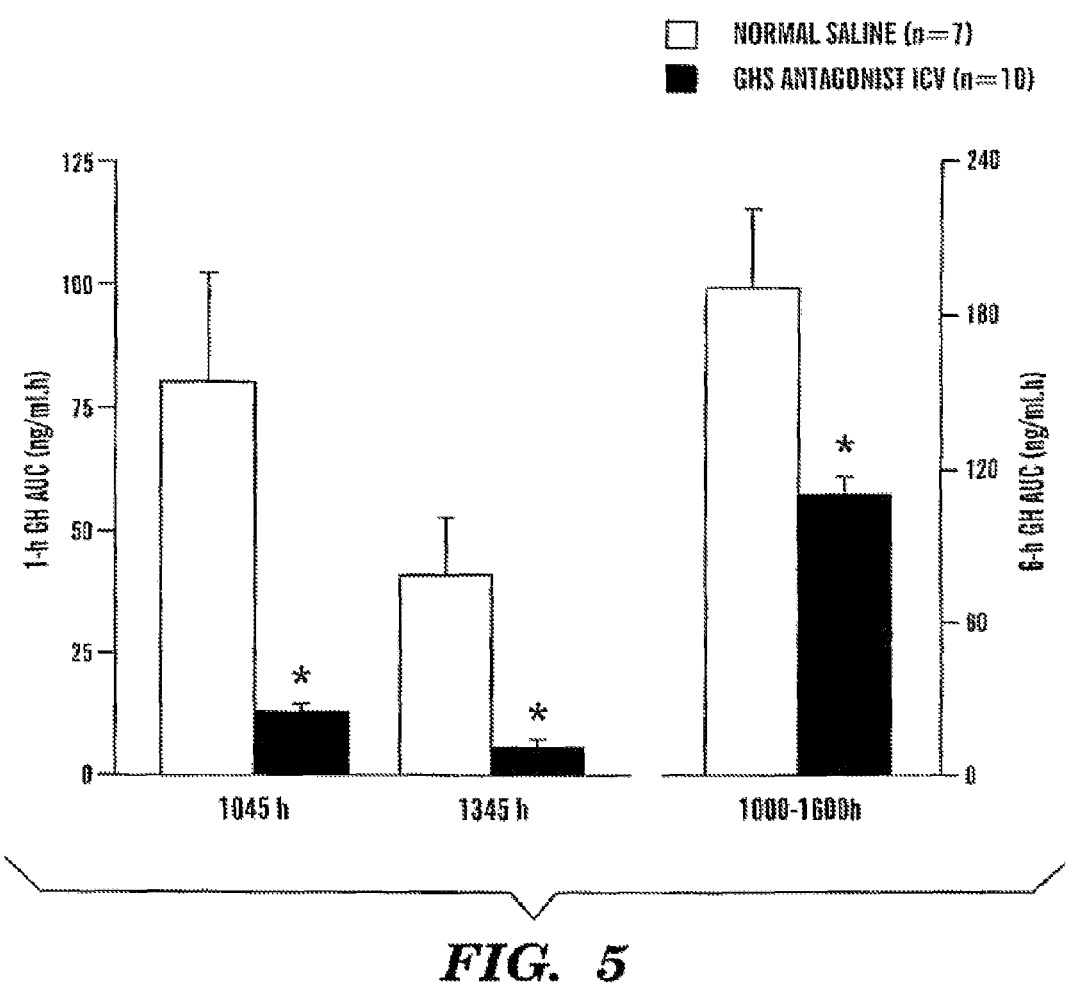
FIG. 5 shows that the 1-h GH AUC's of the spontaneous GH secretory episodes at 1100 h and 1400 h, and the overall 6-h GH AUC, were significantly reduced in animals treated i.c.v. with 5 μg GHS-A compared with normal saline i.c.v.-treated controls. Values are the mean±SE. *, P<0.01 or less compared with normal saline i.c.v.-treated group.
Figure 6:
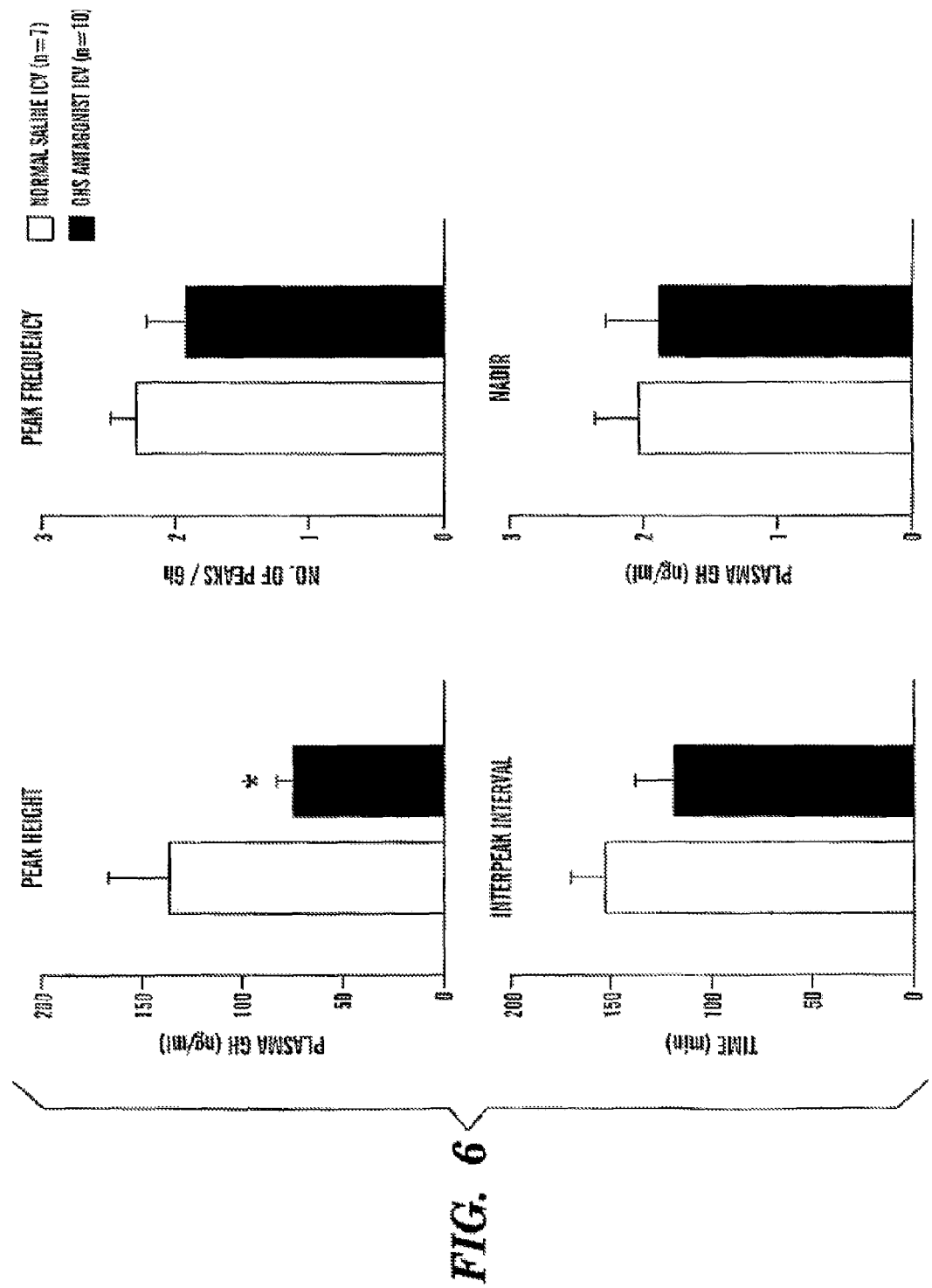
FIG. 6 shows a cluster analysis of the effects of centrally-administered GHS-A (5 μg) or normal saline on spontaneous GH pulse parameters. Cluster analysis revealed a significant suppression of GH peak height, but no significant effect of GHS-A on any other parameters of GH pulsatility, including GH peak frequency, interpeak interval and nadir, compared with normal saline icy-treated controls. Values are the mean±SE. *, P<0.03 vs. normal saline i.c.v.-treated controls.
Figure 7A:
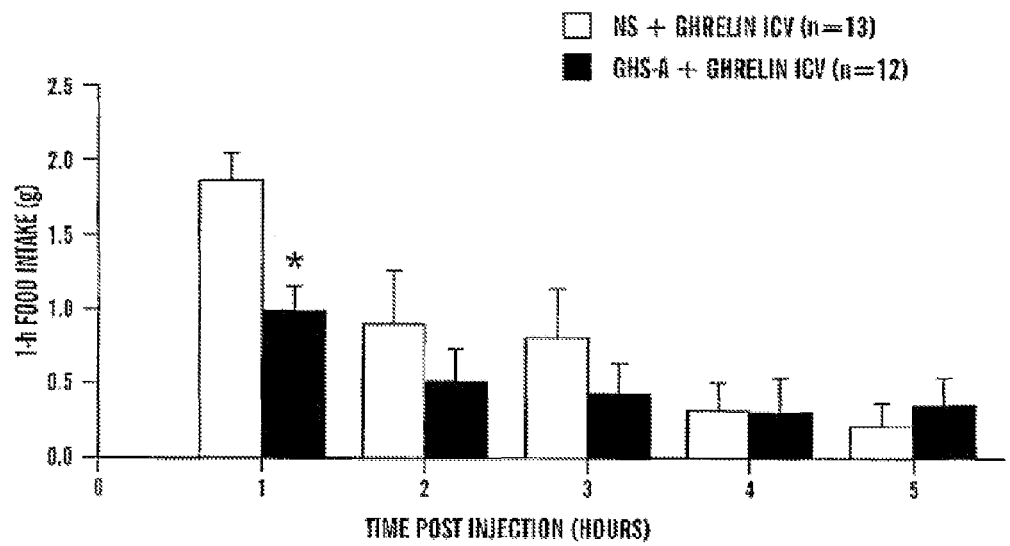
FIGS. 7A and 7B show a feeding response to icy-administered ghrelin (500 ng) in animals pretreated icy with either GHS-A (5 μg) or normal saline (FIG. 7A). GHS-A significantly inhibited ghrelin's stimulatory effects on food intake in the first hour after injections, compared with normal saline i.c.v.-pretreated controls (FIG. 7B). Cumulative food intake was significantly suppressed for up to 5 h after GHS-A injection. Values are the mean±SE. *, P<0.02 or less compared with normal saline icy-pretreated controls.
Figure 7B:
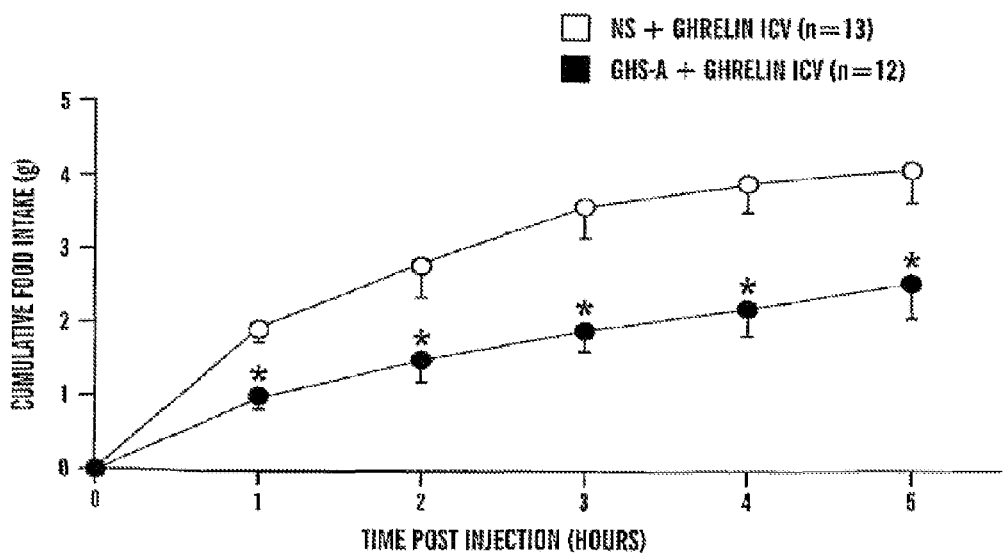
Figure 8A:
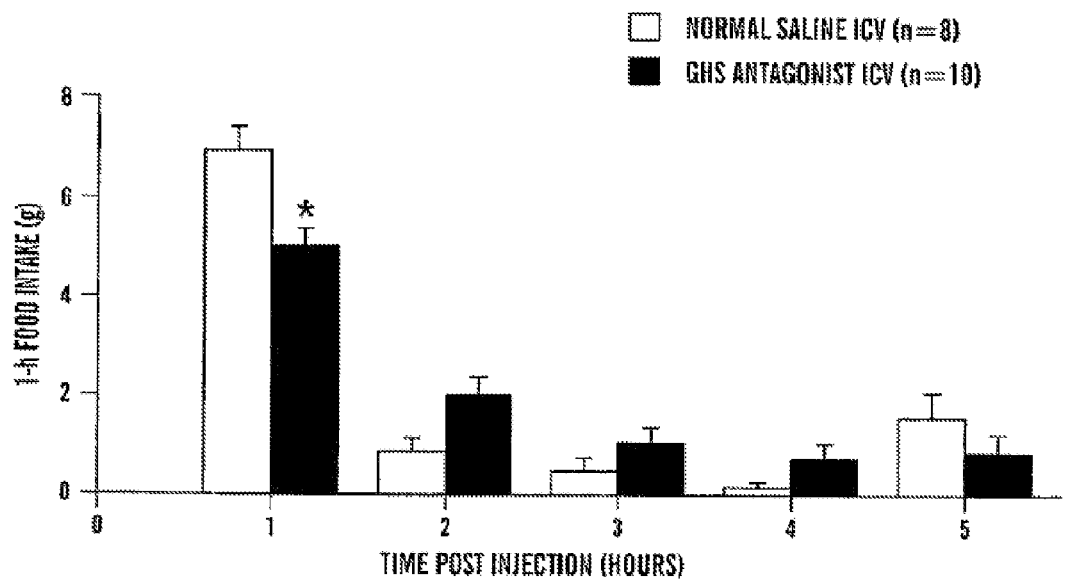
FIGS. 8A and 8B show the effects of icy-administered GHS-A (5 μg) or normal saline on spontaneous food intake in overnight-fasted animals (FIG. 8A). GHS-A significantly inhibited spontaneous food intake in the first hour after injection, compared with normal saline icy-treated controls (FIG. 8B). Cumulative food intake was not inhibited by GHS-A beyond the first hour after injection. Values are the mean±SE. *, P<0.004 compared with normal saline icy-treated controls.
Figure 8B:
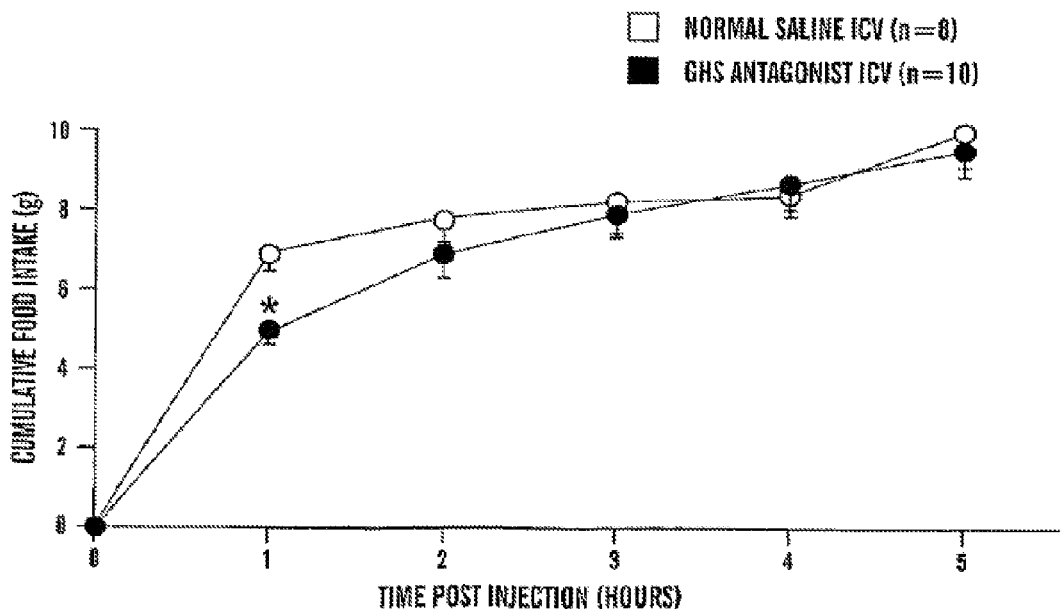
Figure 9:
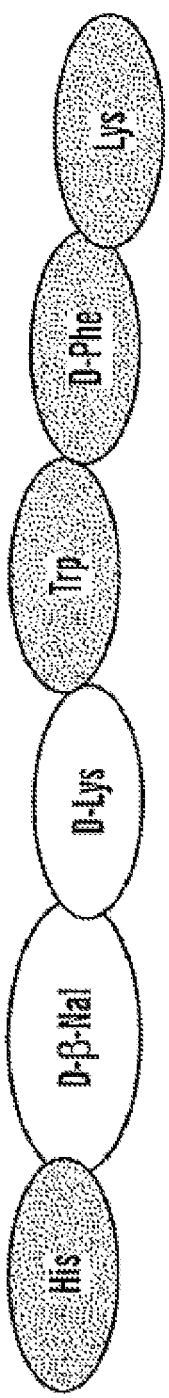
FIG. 9 shows a diagram of one ghrelin receptor antagonist HisDβNalDLysTrpDPheLysNH$_2$ (SEQ ID NO: 26).

The data obtained show that ghrelin receptor antagonists of the present invention such as HisDβNalDLysTrpD-PheLysNH$_2$ (SEQ ID NO: 26), can be used as a tool to disrupt the activity of ghrelin at the level of the CNS. This peptide is a GHRP derivative antagonist. ICV administration of 5 µg of this antagonist prior to i.c.v. injection of ghrelin (500 ng) in free moving, adult rats virtually obliterated the GH response to ghrelin, FIG. 1. A similar block of ghrelin (5 µg iv) induced GH release was observed when rats were pretreated peripherally with the GHS-R antagonist (250 µg i.v.), FIG. 2. In contrast, this GHS-R antagonist did not significantly reduce the GH response to GHRH (5 µg i.v.). With respect to feeding, i.c.v. administered GHS antagonist (5 µg) significantly inhibited ghrelin's (500 ng i.c.v.) stimulatory effects on food intake in the first hr after injections, FIGS. 7A and 8A. These results show the modulatory role for endogenous ghrelin in maintaining the high amplitude of spontaneous GH pulses under physiological conditions, likely acting through the GHS-R 1a on GHRH containing neurons in the arcuate nucleus (16, 17). Without wishing to be bound by theory, while ghrelin may be necessary for the full response of GHRH (the major driving regulator) on pulsatile GH release, it is not an active player in generating the ultradian rhythm of GH secretion. The lack of a dissociated effect on GH and food intake by the GHS antagonist shows that the GHS-R 1a mediates the effects of ghrelin on feeding (via NPY-containing neurons) as well as on GH.

Figure 10:
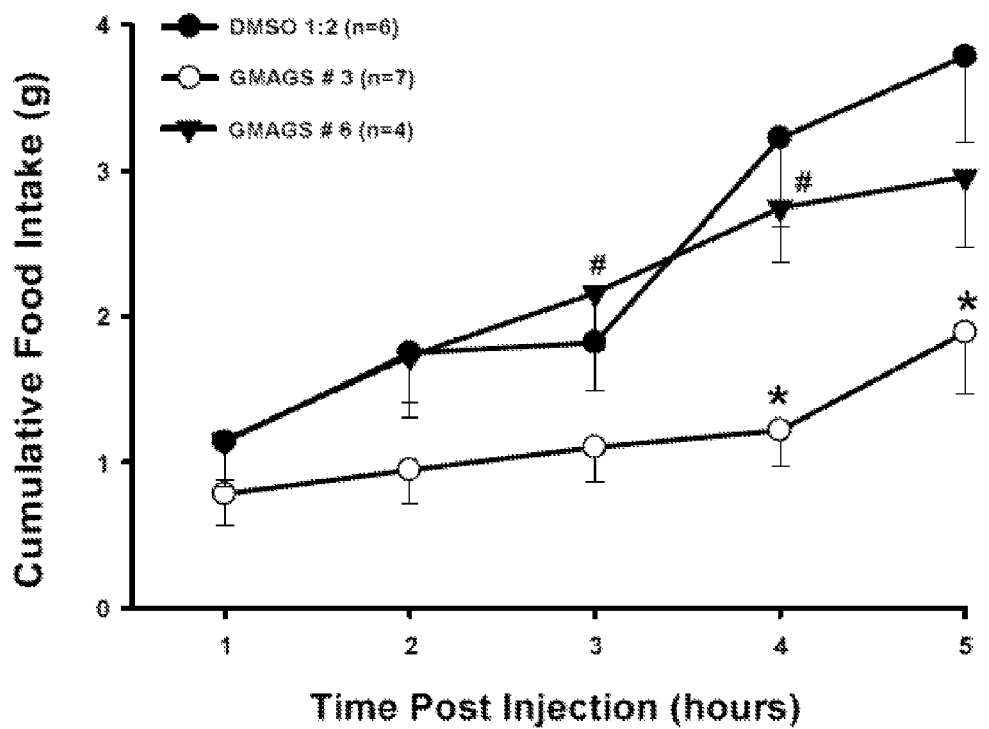
FIG. 10 shows GMAGS(Dap-Oct)FLSPEH-NH$_2$ (peptide #3) (SEQ ID NO: 3), but not GMAGS(Dap-Palmityl)FL-SPEH-NH$_2$ (peptide #6) (SEQ ID NO: 4) inhibited food intake.
Figure 11:
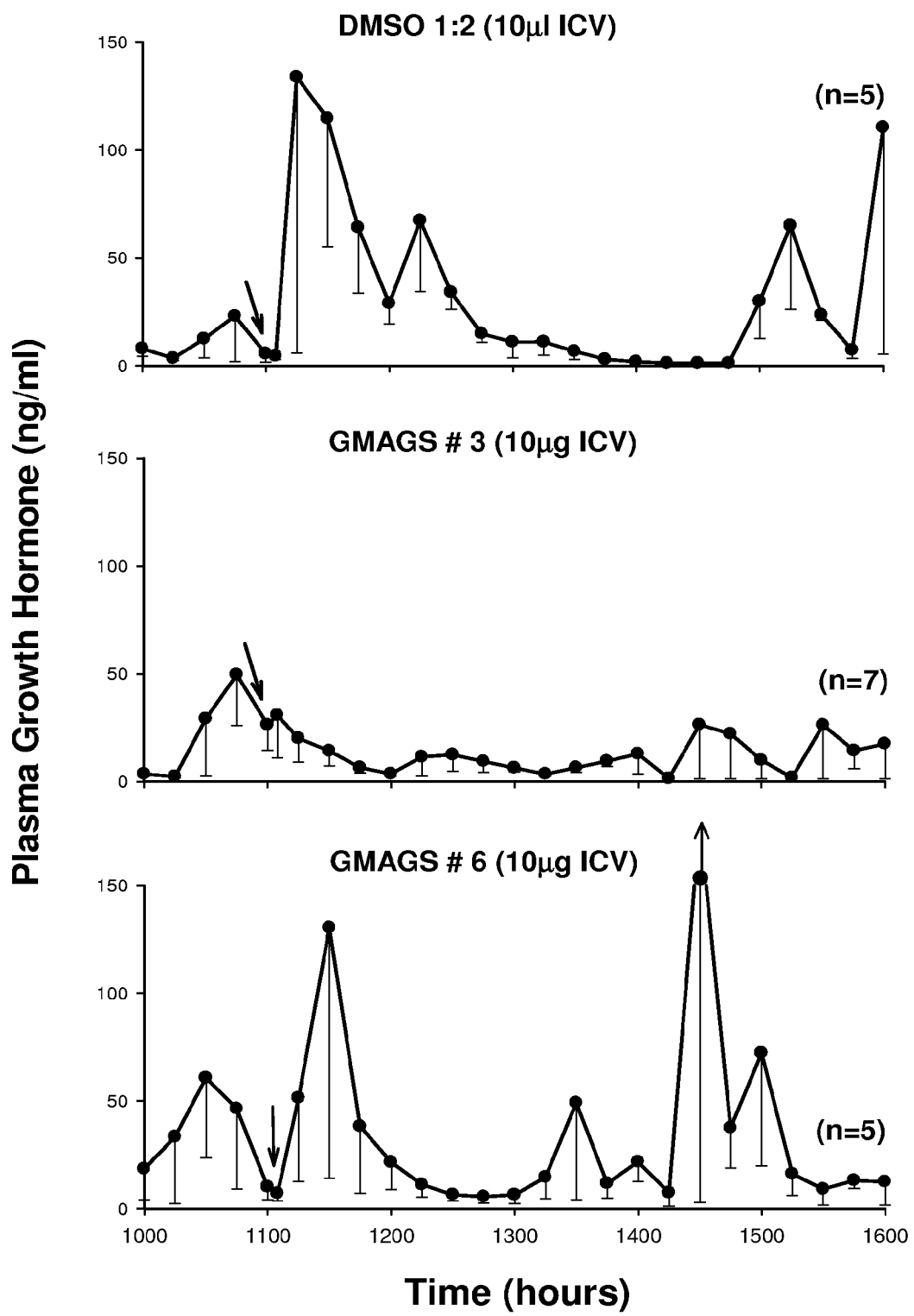
FIG. 11 shows GMAGS(Dap-Oct)FLSPEH-NH$_2$ (peptide #3) (SEQ ID NO: 3), but not GMAGS(Dap-Palmityl)FL-SPEH-NH$_2$ (peptide #6) (SEQ ID NO: 4) inhibited growth hormone secretion.

The administration of the peptide Gly-Met-Ala-Gly-Ser-(Dap-Oct)-Phe-Leu-Ser-Pro-Glu-His-NH$_2$ (SEQ ID NO: 3) reduced both cumulative food intake and inhibited plasma growth hormone levels, FIGS. 10 and 11. Without wishing to be bound by theory, this peptide acts on the hypothalamic ghrelin-R (GHS-R 1a) and inhibits the action of endogenous ghrelin on its hypothalamic receptor. In this peptide, the N-terminal, which is necessary for ghrelin's activity, of the ghrelin pentapeptide core is blocked by the tripeptide Gly-Met-Ala.

A similar peptide, Gly-Met-Ala-Gly-Ser-(Dap-Palmityl)-Phe-Leu-Ser-Pro-Glu-His-NH$_2$ (SEQ ID NO: 4), which has a Dap-palmityl residue instead of the Dap-Octanoyl did not inhibit GH secretion or decreased food intake on administration, FIGS. 10 and 11. Without wishing to be bound by theory, the presence of the larger palmityl group may lower or inhibit the interaction of this peptide with the ghrelin receptor. The sequences disclosed in Tables 1-12 are as follows:

Table 1 discloses SEQ ID NOS 96 and 11-22, respectively, in order of appearance.
Table 2 discloses SEQ ID NOS 97 and 23-28, respectively, in order of appearance.
Table 3 discloses SEQ ID NOS 29-39, respectively, in order of appearance.
Table 4 discloses SEQ ID NOS 97, 40, 40, 41, 41, 42, 42, 43 and 43, respectively, in order of appearance.
Table 5 discloses SEQ ID NOS 44-53, respectively, in order of appearance.
Table 6 discloses SEQ ID NOS 97, 54, 54, 55, 55, 56, 56, 57, 57, 58, 58, 59 and 59, respectively, in order of appearance.
Table 7 discloses SEQ ID NOS 97, 60, 60, 61, 61-65, 65, 66, 66, 53 and 53, respectively, in order of appearance.
Table 8 discloses SEQ ID NOS 67-80, respectively, in order of appearance.
Table 9 discloses SEQ ID NOS 97 and 81-85, respectively, in order of appearance.
Table 10 discloses SEQ ID NO: 97.
Table 11 discloses SEQ ID NO: 97.
Table 12 discloses SEQ ID NOS 96, 98, 13, 27 and 86-89, respectively, in order of appearance.

TABLE 1

In Vitro Ghrelin/GHRP/GHS Receptor Antagonist Activity on Stimulated GH (ng/ml) release from isolated pituitary glands by the pituitary incubation method. Stimulator is His-DTrp-Ala-Trp-DPhe-Lys-NH$_2$ at 10 ng/ml

| Peptide Antagonist | Control | Stimulated Control | Peptide Antagonist Dosage μg/ml | | | | | | |
|---|---|---|---|---|---|---|---|---|---|
| | | | 0.1 | 0.3 | 1 | 3 | 10 | 30 | 100 |
| 1-Tyr-DTrp-DLys-Trp-DPhe-NH$_2$ | 47 ± 22 | 1528 ± 214 | | | | −480 ± 95 | | −363 ± 66 | |
| 2-Tyr-DTrp-Lys-Trp-DPhe-NH$_2$ | −461 ± 163 | 1053 ± 182 | | | | | | | −555 ± 121 |
| 3-His-DTrp-DLys-Trp-DPhe-NH$_2$ | 57 ± 77 | 2120 ± 311 | | 1765 ± 160 | | 949 ± 178 | | 91 ± 103 | |
| 4-His-DTrp-DLys-Phe-DTrp-NH$_2$ | N/A | | | | | | | | |
| 5-His-DTrp-DArg-Trp-DPhe-NH$_2$ | −461 ± 163 | 1953 ± 182 | | | | 341 ± 222 | −125 ± 101 | −122 ± 44 | |
| 6-His-DTrp-DLys-Trp-DPhe-Lys-NH$_2$ | −129 ± 52 | 1267 ± 64 | | 952 ± 200 | 324 ± 181 | 134 ± 91 | −83 ± 132 | −175 ± 59 | |
| 7-DesaminoTyr-DTrp-Ala-TrpD-Phe-NH$_2$ | 58 ± 77 | 2120 ± 311 | | | | 1302 ± 269 | | −959 ± 75 | |
| 8-DesaminoTyr-DTrp-DLys-Trp-DPhe-NH$_2$ | 223 ± 203 | 5189 ± 1513 | 4297 ± 1061 | 2404 ± 802 | 688 ± 327 | −466 ± 432 | −1068 ± 318 | −576 ± 110 | |
| 9-DeaminoTyr-DTrp-Ser-Trp-DPhe-Lys-NH$_2$ | 8 ± 305 | 4436 ± 1006 | | | | | 3325 ± 391 | 3810 ± 621 | |
| 10-DesaminoTyr-DTrp-Ser-Trp-DPhe-NH$_2$ | 8 ± 305 | 4436 ± 1006 | | | | | 3119 ± 488 | 3258 ± 682 | |
| 11-His-DTrp-DTrp-Phe-Met-NH$_2$ | −129 ± 52 | 1267 ± 164 | | 1542 ± 523 | 323 ± 69 | 445 ± 188 | 287 ± 68 | −319 ± 95 | |
| 12-Tyr-DTrp-DTrp-Phe-Phe-NH$_2$ | 47 ± 22 | 1528 ± 214 | | 1274 ± 329 | | | 1034 ± 182 | −167 ± 157 | |

TABLE 2

In Vivo Ghrelin/GHRP/GHS Receptor Antagonist Activity on Stimulated GH (ng/ml) release from rat. Sitmulator is DAla-DβNal-Ala-Trp-DPhe-Lys-NH2 at 0.3 μg or 1 μg

| Peptide Antagonist | Control | Stimulated Control 0.3 μg | Stimulated Control 1 μg | Peptide Antagonist Dosage μg/i.v. | | | | |
|---|---|---|---|---|---|---|---|---|
| | | | | 1 | 3 | 10 | 30 | 100 |
| 1-Glyψ[CH$_2$NH]-DβNal-Ala-Trp-DPhe-Lys-NH$_2$ | 138 ± 11 | 1412 ± 400 | | | | 1112 ± 200 | 578 ± 82 | |
| | 138 ± 11 | | 3214 ± 276 | | | 2307 ± 176 | 890 ± 236 | |
| | 164 ± 14 | | 3105 ± 429 | | | 1842 ± 454 | 1135 ± 140 | |

TABLE 2-continued

In Vivo Ghrelin/GHRP/GHS Receptor Antagonist Activity on Stimulated GH (ng/ml) release from rat. Sitmulator is
DAla-DβNal-Ala-Trp-DPhe-Lys-NH2 at 0.3 μg or 1 μg

| Peptide Antagonist | Control | Stimulated Control 0.3 μg | Stimulated Control 1 μg | Peptide Antagonist Dosage μg/i.v. | | | | |
|---|---|---|---|---|---|---|---|---|
| | | | | 1 | 3 | 10 | 30 | 100 |
| 2-Glyψ[CH$_2$NH]-DβNal-DLys-Trp-DPhe-Lys-NH$_2$ | 143 ± 19 | | 2406 ± 288 | 2305 ± 320 | 1990 ± 196 | 1550 ± 284 | 946 ± 133 | 462 ± 122 |
| 3-DAla-DβNal-DLys-DTrp-Phe-Lys-NH$_2$ | 327 ± 39 | | 4950 ± 98 | | | | 2884 ± 828 | 1198 ± 114 |
| 4-His-DβNal-DLys-Trp-DPhe-Lys-NH$_2$ | 91 ± 46 | 2253 ± 252 | | | | | 733 ± 85 | |
| | 91 ± 46 | | 2825 ± 134 | | | | | 818 ± 269 |
| 5-Ala-His-DTrp-DLys-Trp-DPhe-Lys-NH$_2$ | 91 ± 46 | 2253 ± 252 | | | | | 1487 ± 397 | |
| 6-Alaψ[CH$_2$NH]-DβNal-Ala-Trp-DPhe-Lys-NH$_2$ | 164 ± 14 | | 3104 ± 429 | | 2771 ± 157 | 2341 ± 416 | 1948 ± 450 | 1639 ± 221 |

TABLE 3

In Vivo Ghrelin/GHRP/GHS Receptor Antagonist Activity on Unstimulated Basal GH (ng/ml) Release from rat.

| Partial Agonist/Antagonist Peptide | Control | Stimulated Control 0.3 μg | Stimulated Control 1 μg | Peptide Dosage μg/i.v. | | | | |
|---|---|---|---|---|---|---|---|---|
| | | | | 1 | 3 | 10 | 30 | 100 |
| 1-DβNal-Ala-Trp-DPhe-Ala-NH$_2$ | 253 ± 34 | 1991 ± 214 | | 623 ± 60 | 694 ± 70 | 654 ± 58 | 713 ± 71 | |
| 2-DAla-DcyclohexylAla-Ala-Phe-DPhe-Nle-NH$_2$ | 204 ± 46 | 1850 ± 324 | | 435 ± 152 | 195 ± 34 | 250 ± 41 | 393 ± 51 | 697 ± 75 |
| 3-DcyclohexylAla-Ala-Phe-DTrp-Lys-NH$_2$ | 204 ± 46 | 1765 ± 330 | | 199 ± 63 | 266 ± 68 | 199 ± 23 | 346 ± 82 | 350 ± 61 |
| 4-DAla-DβNal-Ala-Thr-DThr-Lys-NH$_2$ | 244 ± 56 | 1538 ± 215 | | | 255 ± 38 | | 288 ± 31 | 386 ± 57 |
| 5-DcyclohexylAla-Ala-Trp-DPhe-NH$_2$ | 176 ± 44 | 2282 ± 258 | | | 181 ± 28 | 237 ± 18 | 354 ± 81 | 771 ± 76 |
| 6-DAla-DβNal-Ala-Ala-DAla-Lys-NH$_2$ | 135 ± 19 | 1485 ± 200 | | | 235 ± 43 | 178 ± 33 | 172 ± 15 | 185 ± 39 |
| 7-DβNal-Ala-Trp-DPhe-Leu-NH$_2$ | 145 ± 48 | 1470 ± 338 | | | 253 ± 79 | 277 ± 43 | 347 ± 66 | 645 ± 117 |
| 8-His-DTrp-Phe-Trp-DPhe-Lys-NH$_2$ | 240 ± 55 | | 2766 ± 726 | 67 ± 14 | 141 ± 53 | 197 ± 70 | 509 ± 48 | |
| 9-DAla-DβNal-DAla-DTrp-Phe-Lys-NH$_2$ | 100 ± 22 | | 4785 ± 798 | 184 ± 55 | 467 ± 201 | 244 ± 107 | | |
| 10-βAla-Trp-DAla-DTrp-Phe-NH$_2$ | 195 ± 33 | | 4130 ± 349 | | | | 341 ± 46 | 636 ± 171 |
| 11-His-Trp-DAla-DTrp-Phe-LysNH$_2$ | 150 ± 26 | 1847 ± 362 | | 204 ± 44 | 127 ± 44 | 83 ± 5 | | |

TABLE 4

In Vivo Ghrelin/GHRP/GHS Receptor Antagonist Activity on Unstimulated and Stimulated (S) GH (ng/ml) release from rats.
The Stimulator is DAla-DβNal-Ala-Trp-DPhe-Lys-NH2 at 0.3 μg, 1 μg, or 10 μg.

| Peptide Antagonist (P) | | Control | Stimulated Control 0.3 | Stimulated Control 1 | Peptide Anatgonist Dosage μg/i.v. | | | | |
|---|---|---|---|---|---|---|---|---|---|
| | | | | | 1 | 3 | 10 | 30 | 100 |
| Pentobarbital Rats | | | | | | | | | |
| 1-DLys-DβNal-Ala-Trp-DPhe-Lys-NH$_2$ | −S | 197 ± 81 | | | | 616 ± 169 | 847 ± 17 | 629 ± 148 | 228 ± 45 |
| 1-DLys-DβNal-Ala-Trp-DPhe-Lys-NH$_2$ | P + S | | 5052 ± 511 | | | 5232 ± 346 | 3404 ± 396 | 704 ± 169 | |
| 2-DAla-DβNal-DLys-DTrp-Phe-Lys-NH$_2$ | −S | 327 ± 39 | | | | | | 323 ± 50 | 812 ± 6 |
| 2-DAla-DβNal-DLys-DTrp-Phe-Lys-NH$_2$ | P + S | | | 4950 ± 98 | | | | 2884 ± 828 | 1198 ± 114 |
| Non-Pentobarbital Rats | | | | | | | | | |
| 1-Tyr-DAla-Phe-Aib-NH$_2$ | −S | 12 ± 1 | 10 μg | | | | | 18 ± 1 | |
| 1-Tyr-DAla-Phe-Aib-NH$_2$ | P + S | | | 72 ± 9 | | | | 23 ± 5 | |
| 2-Tyr-DAla-Sar-NMePhe-NH$_2$ | −S | 12 ± 1 | | | | | | 18 ± 4 | |
| 2-Tyr-DAla-Sar-NMePhe-NH$_2$ | P + S | | | 72 ± 9 | | | | 24 ± 6 | |

TABLE 5

In Vivo Ghrelin/GHRP/GHS Receptor Antagonist Activity on Unstimulated Basal GH (ng/ml) release from rats.

| Peptide Antagonist | Control | Stimulated Control 0.3 μg | Stimulated Control 1 μg | Peptide Antagonist Dosage μg/i.v. 1 | 3 | 10 | 30 | 100 |
|---|---|---|---|---|---|---|---|---|
| 1-αγAbu-DTrp-DTrp-Ser-NH$_2$ | 106 ± 9 | | 2742 ± 206 | 80 ± 35 | | 62 ± 15 | 67 ± 8 | |
| 2-αγAbu-DTrp-DTrp-Lys-NH$_2$ | 136 ± 31 | | 1968 ± 294 | 57 ± 7 | 84 ± 18 | 62 ± 15 | | |
| 3-αγAbu-DTrp-DTrp-Orn-NH$_2$ | 167 ± 13 | | 2819 ± 530 | 118 ± 16 | | 126 ± 27 | 79 ± 31 | |
| 4-αAbu-DTrp-DTrp-Orn-NH$_2$ | 167 ± 13 | | 2819 ± 530 | 85 ± 25 | | 88 ± 18 | 50 ± 6 | |
| 5-DThr-DαNal-DTrp-DPro-Arg-NH$_2$ | 164 ± 23 | | 2691 ± 281 | 60 ± 5 | 130 ± 24 | 134 ± 31 | | |
| 6-DAla-Ala-DAla-DTrp-Phe-Lys-NH$_2$ | 180 ± 20 | | 4785 ± 798 | | | 228 ± 76 | 172 ± 14 | 153 ± 45 |
| 7-Alaψ[CH$_2$NH]His-DTrp-Ala-Trp-DPhe-Lys-NH$_2$ | 211 ± 30 | | 2335 ± 323 | 127 ± 32 | 147 ± 37 | | | |
| 8-Lys-DHis-DTrp-Phe-NH$_2$ | 211 ± 30 | | 2335 ± 323 | | | 121 ± 24 | | |
| 9-γAbu-DTrp-DTrp-Orn-NH$_2$ | 167 ± 13 | | 2819 ± 530 | 82 ± 28 | | 90 ± 5 | 113 ± 32 | |
| 10-inip-Trp-Trp-Phe-NH$_2$ | 155 ± 31 | | 2503 ± 240 | | | 69 ± 3 | 81 ± 10 | | inip = isonipecotic carboxylic acid
αγAbu = alpha gamma diaminobutyric acid

TABLE 6

In Vitro Ghrelin/GHRP/GHS Receptor Antagonist Activity on Unstimulated and Stimulated(S) GH (ng/ml) release from cell culture of pituitary cells. The Sitmulator is DAla-DβNal-Ala-Trp-DPhe-Lys-NH$_2$ at at 10 ng/ml.

| Peptide Antagonist (P) | | Control | Stimulated Control 10 ng/ml | Peptide Antagonist Dosage μg/ml 0.1 | 0.3 | 1 | 3 | 10 | 30 |
|---|---|---|---|---|---|---|---|---|---|
| 1-Ac-DTrp-Phe-DTrp-Leu-NH$_2$ | −S | 1640 ± 100 | | | | | | | 400 ± 20 |
| 1-Ac-DTrp-Phe-DTrp-Leu-NH$_2$ | P + S | | 2420 ± 0 | | | | 2100 ± 0 | 1200 ± 20 | 600 ± 20 |
| 2-Ac-DTrp-Phe-DTrp-Lys-NH$_2$ | −S | 1640 ± 100 | | | | | | | 350 ± 80 |
| 2-Ac-DTrp-Phe-DTrp-Lys-NH$_2$ | P + S | | 2420 ± 0 | | | | 1750 ± 10 | 800 ± 0 | 470 ± 30 |
| 3-Ac-DTrp-DTrp-Lys-NH$_2$ | −S | 1640 ± 100 | | | | | | 610 ± 30 | 420 ± 20 |
| 3-Ac-DTrp-DTrp-Lys-NH$_2$ | P + S | | 2420 ± 0 | | | | 1970 ± 70 | 1130 ± 30 | 900 ± 0 |
| 4-DLys-Tyr-DTrp-DTrp-Phe-Lys-NH$_2$ | −S | 1640 ± 100 | | | | | | 1340 ± 60 | 1060 ± 0 |
| 4-DLys-Tyr-DTrp-DTrp-Phe-Lys-NH$_2$ | P + S | | 2420 ± 0 | | | | 2100 ± 40 | 1710 ± 10 | 1270 ± 10 |
| 5-Ac-DβNal-Leu-Pro-NH$_2$ | −S | 1233 ± 49 | | | | | | | |
| 5-Ac-DβNal-Leu-Pro-NH$_2$ | P + S | | 2811 ± 229 | | | | 1998 ± 36 | 1206 ± 53 | 860 ± 33 |
| 6-βAla-Trp-DTrp-DTrp-Orn-NH$_2$ | −S | 1722 ± 205 | | | | | | | |
| 6-βAla-Trp-DTrp-DTrp-Orn-NH$_2$ | P + S | | 2385 ± 8 | | | 3103 ± 471 | | 1633 ± 34 | 1166 ± 13 |

TABLE 7

In Vitro Ghrelin/GHRP/GHS Receptor Antagonist Activity on Unstimulated and Stimulated (S) GH (ng/ml) release from cell culture of pituitary cells. The Stimulator is DAla-DβNal-Ala-Trp-DPhe-Lys-NH$_2$ at 1 ng/ml.

| Partial Agonist/Antagonist Peptide (P) | | Control | Stimulated Control 1 ng/ml | Peptide Dosage μg/ml 1 | 3 | 10 | 30 | 100 |
|---|---|---|---|---|---|---|---|---|
| 1-DVal-DαNal-DTrp-Phe-Arg-NH$_2$ | −S | 480 ± 16 | | | 934 ± 34 | 850 ± 19 | 598 ± 7 | |
| 1-DVal-DαNal-DTrp-Phe-Arg-NH$_2$ | P + S | | 1399 ± 27 | | 949 ± 52 | 672 ± 64 | 520 ± 5 | |
| 2-DLeu-DαNal-DTrp-Phe-Arg-NH$_2$ | −S | 480 ± 16 | | | 1156 ± 10 | 971 ± 5 | 520 ± 5 | |
| 2-DLeu-DαNal-DTrp-Phe-Arg-NH$_2$ | P + S | | 1399 ± 27 | | 1136 ± 7 | 957 ± 44 | 777 ± 71 | |
| 3-CyclohexylAla-DαNal-DTrp-Phe-Arg-NH$_2$ | P + S | 734 ± 6 | 1841 ± 41 | | 1362 ± 59 | 1021 ± 22 | | |
| 4-DTrp-DαNal-DTrp-Phe-Arg-NH$_2$ | P + S | 734 ± 6 | 1851 ± 41 | | 1239 ± 17 | 878 ± 28 | | |
| 5-DAla-DβNal-DPro-Phe-Arg-NH$_2$ | P + S | 734 ± 6 | 1851 ± 41 | | 1779 ± 27 | 1328 ± 59 | | |
| 6-Ac-DαNal-DTrp-Phe-Arg-NH$_2$ | −S | 480 ± 16 | | | 1106 ± 7 | 996 ± 16 | 704 ± 76 | |
| 6-Ac-DαNal-DTrp-Phe-Arg-NH$_2$ | P + S | | 1399 ± 27 | | 1128 ± 12 | 970 ± 25 | 704 ± 76 | |
| 7-DαNal-DTrp-Phe-Arg-NH$_2$ | −S | 480 ± 16 | | | 1170 ± 43 | 987 ± 52 | 727 ± 44 | |
| 7-DαNal-DTrp-Phe-Arg-NH$_2$ | P + S | | 1399 ± 27 | | 1288 ± 40 | 1079 ± 17 | 824 ± 29 | |
| 8-inip-Trp-Trp-Phe-NH$_2$ | −S | 625 ± 12 | | | | 553 ± 111 | 247 ± 9 | 132 ± 7 |
| 8-inip-Trp-Trp-Phe-NH$_2$ | P + S | | 749 ± 28 | | | 393 ± 6 | 278 ± 35 | 154 ± 4 | inip = isonipecotic carboxylic acid

TABLE 8

In Vitro Ghrelin/GHRP/GHS Receptor Antagonist Activity on Unstimulated Basal GH (ng/ml) release from cell cultures of pituitary cells.

| Peptide Antagonist (P) | Control | Stimulated control 1 ng/ml | Peptide Antagonist Dosage μg/ml | | | | |
|---|---|---|---|---|---|---|---|
| | | | 1 | 3 | 10 | 30 | 100 |
| 1-His-DTrp-DTrp-Lys-NH$_2$ | 1089 ± 47 | 1551 ± 2 | | 1124 ± 37 | 749 ± 10 | 615 ± 41 | |
| 2-Ac-DβNal-DTrp-NH$_2$ | 1089 ± 47 | 1551 ± 2 | | 1264 ± 2 | 980 ± 72 | 699 ± 7 | |
| 3-αAib-DTrp-DcyclohexylAla-NH$_2$ | 478 ± 8 | 1014 ± 8 | 980 ± 44 | 826 ± 32 | 602 ± 53 | 492 ± 11 | |
| 4-αAib-DTrp-DAla-cyclohexylAla-NH$_2$ | 478 ± 8 | 1014 ± 8 | 1086 ± 52 | 1103 ± 18 | 994 ± 22 | 704 ± 115 | |
| 5-DAla-DcyclohexylAla-Ala-Ala-Phe-DPhe-Nle-NH$_2$ | 500 ± 116 | 1991 ± 214 | 286 ± 75 | 177 ± 44 | 271 ± 38 | 376 ± 28 | |
| 6-DPhe-Ala-Phe-DPal-NH$_2$ | 176 ± 44 | | | 170 ± 19 | 181 ± 31 | 161 ± 20 | 146 ± 21 |
| 7-DPhe-Ala-Phe-DPhe-Lys-NH$_2$ | 368 ± 32 | | | | 267 ± 27 | 276 ± 65 | 360 ± 84 |
| 8-DLys-Tyr-DTrp-DTrp-Phe-NH$_2$ | 1403 ± 13 | | 1451 ± 19 | 1175 ± 77 | 1129 ± 6 | 744 ± 44 | |
| 9-Ac-DLys-Tyr-DTrp-DTrp-Phe-NH$_2$ | 1403 ± 13 | | | 105 ± 8 | 950 ± 91 | 782 ± 56 | 756 ± 1 |
| 10-Arg-DTrp-Leu-Tyr-Trp-Pro(cyclic Arg-Pro) | 1403 ± 13 | | | 1480 ± 19 | 802 ± 26 | 601 ± 16 | 509 ± 49 |
| 11-Ac-DβNal-PicLys-ILys-DPhe-NH$_2$ | 1333 ± 41 | | | 1013 ± 207 | 976 ± 13 | 928 ± 16 | |
| 12-DPal-Phe-DTrp-Phe-Met-NH$_2$ | 1333 ± 41 | | | 1081 ± 50 | 997 ± 30 | 425 ± 25 | |
| 13-DPhe-Trp-DPhe-Phe-Met-NH$_2$ | 1333 ± 41 | | | 1146 ± 34 | 1086 ± 32 | 871 ± 89 | |
| 14-DPal-Trp-DPhe-Phe-Met-NH$_2$ | 1333 ± 41 | | | 1105 ± 18 | 891 ± 4 | 567 ± 24 | |

ILys = Lys(iPr)

TABLE 9

In Vitro Ghrelin/GHRP/GHS Receptor Antagonist Activity on Unstimulated and Stimulated(S) GH (ng/ml) release from cell cultures of pituitary cells. The Stimulator is DAla-DβNal-Ala-Trp-DPhe-Lys-NH$_2$ at 1 ng/ml.

| Peptide Antagonist (P) | | Control | Stimulated control 1 ng/ml | Peptide Antagonist Dosage μg/ml | | | | |
|---|---|---|---|---|---|---|---|---|
| | | | | 1 | 3 | 10 | 30 | 100 |
| 1-βAla-Pal-DTrp-DTrp-Orn-NH$_2$ | −S | 894 ± 18 | | | | 759 ± 11 | 861 ± 25 | |
| | P + S | | 1232 ± 34 | | | 855 ± 11 | 828 ± 11 | |
| 2-αγAbu-Trp-DTrp-DTrp-Orn-NH$_2$ | −S | 894 ± 18 | | | | 609 ± 3 | 503 ± 5 | |
| | P + S | | 1232 ± 34 | | | 666 ± 2 | 578 ± 31 | |
| 3-βAla-Trp-DTrp-DTrp-Lys-NH$_2$ | −S | 894 ± 18 | | | | 733 ± 25 | 616 ± 21 | |
| | P + S | | 1232 ± 34 | | | 806 ± 45 | 596 ± 18 | |
| 4-γAbu-Trp-DTrp-DTrp-Orn-NH$_2$ | −S | 894 ± 18 | | | | 840 ± 30 | 634 ± 1 | |
| | P + S | | 1232 ± 34 | | | 835 ± 5 | 655 ± 40 | |
| 5-Ava-Trp-DTrp-DTrp-Orn-NH$_2$ | −S | 894 ± 18 | | | | 481 ± 3 | 406 ± 21 | |
| | P + S | | 1232 ± 34 | | | 505 ± 19 | 420 ± 34 | |

αγAbu = alpha gamma diaminobutyric acid
Ava = aminovaleric acid

TABLE 10

In Vitro Ghrelin/GHRP/GHS Receptor Antagonist Activity on Unstimulated and Stimulated(S) GH (ng/ml) release from cell cultures of pituitary cells. The Stimulator is DAla-DβNal-Ala-Trp-DPhe-Lys-NH$_2$ at 1 ng/ml.

| Partial Peptide/Non-peptide(P) | | Control | Stimulated Control 1 ng/ml | Partial Peptide/Non-peptide Dosage μg/ml | | | |
|---|---|---|---|---|---|---|---|
| | | | | 1 | 3 | 10 | 30 |
| 1-DTrp-4-phenylpiperdinamide | P + S | 385 ± 49 | 1060 ± 24 | 815 ± 26 | 390 ± 35 | 520 ± 61 | 577 ± 24 |
| | | | | 1085 ± 1 | 917 ± 4 | 344 ± 6 | 486 ± 29 |
| 2-2,3-di[N-(2-methoxylphenyl)piperazyl-naphthalene carboxylamide | P + S | 361 ± 30 | 905 ± 6 | 338 ± 3 | 204 ± 10 | 262 ± 4 | |
| | | | | 654 ± 18 | 442 ± 4 | 537 ± 28 | |
| | P + S | 385 ± 17 | 1153 ± 36 | | | 136 ± 11 | 118 ± 8 |
| | | | | | | 648 ± 16 | 309 ± 46 |
| 3-Benzamide-DSerDLysTrp-p-phenylpiperidinamide | P + S | 370 ± 24 | 1216 ± 26 | | 393 ± 54 | 369 ± 30 | |
| | | | | | 432 ± 25 | 353 ± 10 | |
| 4-Ser(Bzl)Lys(Ac)DTrp-p-phenylpiperidinamide | P + S | 385 ± 17 | 1153 ± 36 | | | 388 ± 41 | 273 ± 39 |
| | | | | | | 571 ± 32 | 399 ± 24 |
| 5-O-(2-methylallyl) benzophonone oxime | P + S | 969 ± 33 | 1461 ± 58 | | | 929 ± 28 | 616 ± 23 |
| | | | | | | 1281 ± 58 | 699 ± 53 |
| 6-D Ser(BZL)-N'-phenyl-N-piperazinamide | P + S | 626 ± 4 | 1016 ± 18 | | | 585 ± 10 | 368 ± 2 |
| | | | | | | 719 ± 26 | 435 ± 0 |
| 7-αAibDSer(BZL)-N'-phenyl-N-piperazinamide | P + S | 626 ± 4 | 1016 ± 18 | | | 777 ± 34 | 499 ± 18 |
| | | | | | | 878 ± 30 | 510 ± 15 |
| 8-2-[acetylester]-3-(p-m-methoxyl | P + S | 421 ± 16 | 859 ± 4 | | | 373 ± 2 | 176 ± 11 |

TABLE 10-continued

In Vitro Ghrelin/GHRP/GHS Receptor Antagonist Activity on Unstimulated and Stimulated(S) GH (ng/ml) release from cell cultures of pituitary cells. The Stimulator is DAla-DβNal-Ala-Trp-DPhe-Lys-NH$_2$ at 1 ng/ml.

| Partial Peptide/Non-peptide(P) | Control | Stimulated Control 1 ng/ml | Partial Peptide/Non-peptide Dosage μg/ml | | | |
|---|---|---|---|---|---|---|
| | | | 1 | 3 | 10 | 30 |
| phenyl)piperidinamide]-naphthalene carboxamide | | | | | 480 ± 9 | 223 ± 22 |

TABLE 11

In Vitro Ghrelin/GHRP/GHS Receptor Antagonist Activity on Unstimulated and Stimulated(S) GH (ng/ml) release from cell cultures of pituitary cells. The Stimulator is DAla-DβNal-Ala-Trp-DPhe-Lys-NH$_2$ at 1 ng/ml.

| Partial Peptide/Non-peptide(P) | | Control | Stimulated Control 1 ng/ml | Partial Peptide/Non-peptide Dosage μg/ml | | | |
|---|---|---|---|---|---|---|---|
| | | | | 1 | 3 | 10 | 30 |
| 1-2-[methylester]-3-[p-methylphenylamide naphthalene carboxylamide | P + S | 626 ± 4 | 1016 ± 18 | | | 754 ± 32<br>1149 ± 33 | 498 ± 26<br>886 ± 29 |
| 2-p-phenyl(piperidinamide-DTrpLysSer(BZL)-acetylamide | P + S | 408 ± 40 | 905 ± 6 | 680 ± 13 | 489 ± 41 | 245 ± 16 | |
| 3-γAbuDTrp-p-[m-methoxyphenyl]piperidinamide | P + S | 364 ± 31 | 947 ± 11 | | | 557 ± 19<br>526 ± 27 | 378 ± 18<br>428 ± 22 |
| 4-αAibDTrp-p-(o-methoxylphenyl)piperidinamide | P + S | 377 ± 24 | 947 ± 33 | | | 365 ± 2<br>441 ± 21 | 375 ± 30<br>384 ± 16 |
| 5-2-[ethylester-3-m-methoxylphenylamide]naphthalene carboxylamide | P + S | 364 ± 31 | 947 ± 11 | | | 698 ± 18<br>670 ± 32 | 552 ± 20<br>458 ± 15 |
| 6-1,3-diaminobutyricamide-DβNal-4-phenylpiperidinamide | P + S | 626 ± 4 | 1016 ± 18 | | | 794 ± 34<br>644 ± 33 | 504 ± 20<br>529 ± 20 |

TABLE 12

In Vitro Ghrelin/GHRP/GHS Receptor Antagonist Activity on Unstimulated and Stimulated(S) GH (ng/ml) release from isolated pituitary glands by the pituitary incubation method. The Stimulator S = His-DTrp-Ala-Trp-DPhe-Lys-NH$_2$ (10 ng/ml) and Stimulator *S = Tyr-DTrp-Ala-Trp-DPhe-NH$_2$ (0.3 μg/ml)

| Peptide(P) | | Control | Stimulated Control | Peptide Dosage μg/ml | | | | |
|---|---|---|---|---|---|---|---|---|
| | | | | 1 | 3 | 10 | 30 | 100 |
| 1-His-DTrp-DLys-Trp-DPhe-NH$_2$ | P + S | 654 ± 255 | 8769 ± 583 | 8121 ± 687 | 5929 ± 857 | 3017 ± 413 | 269 ± 140 | |
| 2-Ala-His-DTrp-DLys-Trp-DPhe-Lys-NH$_2$ | P + S | 1674 ± 1171 | 5218 ± 507 | 4850 ± 539 | 947 ± 551 | 3977 ± 1360<br>−2384 ± 868 | | |
| 3-DLys-Tyr-DTrp-Ala-Trp-DPhe-NH$_2$* | P + S | 148 ± 137 | 2218 ± 194 | | 1233 ± 268 | 688 ± 3233 | 916 ± 80 | |
| 4-His-DTrp-DArg-Trp-DPhe-NH$_2$ | P + S | −14 ± 62 | 776 ± 142 | | −109 ± 124<br>136 ± 108 | 290 ± 124 | −500 ± 104<br>−454 ± 95 | |
| 5-<Glu-His-Trp-DSer-DArg-NH$_2$ | | 246 ± 67 | | | | −4 ± 25 | 6 ± 34 | |
| 6-DPhe-DPhe-DTrp-Met-DLys-NH$_2$* | P + S | 148 ± 137 | 2218 ± 194 | | 1584 ± 136 | 1398 ± 98 | 1388 ± 300 | |

All patents and other publications identified throughout the specification and examples and in the references section are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

REFERENCES

1. Kojima M, Hosada H, Date Y, Nakazato M, Matsuo H, Kangawa K. Ghrelin is a growth-hormone-releasing acylated peptide from stomach. Nature 1999; 402:656-60.
2. Bowers C Y. Growth Hormone Releasing Peptides (GH-RPs). In: Handbook of Physiology, Eds. J Kostyo, H Goodman 1999; Oxford University Press, New York, pg 267-297.
3. Bowers C Y. Unnatural growth hormone-releasing peptide begets natural ghrelin. J Clin Endocrinol Metab 2001; 86:1464-1469.
4. Wren A M, Seal L J, Cohen M A, Brynes A E, Frost G S, Murphy K G et al. Ghrelin enhances appetite and increases food intake in humans. J Clin Endocrinol Metab 2001; 86:5992-5995.

5. Laferrere B, Abraham C, Russell C D, Bowers C Y. Growth hormone releasing peptide-2 (GHRP-2), like ghrelin, increases food intake in healthy men. J Clin Endocrinol Metab 2005; 90:611-614.
6. Laferrere B, Hart A B, Bowers C Y. Obese subjects respond to the stimulatory effect of the ghrelin agonist Growth Hormone Releasing Peptide-2 (GHRP-2) on food intake. Obesity 14(6):1056-63, 2006.
7. Bowers C Y. Octanoyl ghrelin is hypothalamic rooted. Endocrinology 146:2508-9, 2005.
8. Sethumadhaven K, Veeraragavan K, Bowers C Y. Demonstration and characterization of the specific binding of growth hormone-releasing peptide (GHRP) to rat anterior pituitary and hypothalamic membranes. Biochem Biophy Res Comm 178(1):31-37, 1991.
9. Bitar K G, Bowers C Y, Coy D H. Effects of Substance P/Bombesin antagonists on the release of growth hormone by GHRP and GHRH. Biochem Biophy Res Comm 180 (1):156-161, 1991.
10. Veeraragavan K, Sethumadhavan K, Bowers C Y. Growth hormone releasing peptide (GHRP) binding to porcine anterior pituitary and hypothalamic membranes. Life Sciences 50:1149-1155, 1992
11. Camina J P. Cell biology of the ghrelin receptor. J Neuroendocrinol 2006; 18:65-76.
12. Bodart V, Febbraio M, Demers A, McNicoll N, Pohankova P, Perreault A et al. CD36 mediates cardiovascular action of growth hormone-releasing peptides in the heart. Circ Res 2002; 90:844-49.
13. Holst B, Cygankiewicz A, Jensen T H, Ankersen M, Schwartz T W. High constitutive signaling of the ghrelin receptor-identification of a potent inverse agonist. Mol. Endocrinol. 2003; 17 (11):2201-10.
14. Holst B, Holliday N D, Bach A, Elling C E, Cox H M, Schwartz T W. Common structural basis for constitutive activity of the ghrelin receptor family. J Biol Chem 2004; 279:53805-53817.
15. Petersen P S, Wolsbye D, Lang M, Beck-Sickinger A, Schwartz T W, Holst B. Effect of icy infusion of the ghrelin receptor selective inverse agonist [DArg$^1$,DPhe$^5$,DTrp$^{7,9}$ Leu$^{11}$]-Sub P on body weight gain in rats. Keystone Symposium Gut Hormone and Other Regulators of Appetite, Satiety and Energy Expenditure Mar. 2-7, 2006, p. 53.
16. Holst B, Mokrosinski J, Lang M, Brandt E, Nygaard R, Frimurer T M, Beck-Sickinger A G, Schwartz T W. Identification of an efficacy switch region in the ghrelin receptor responsible for interchange between agonism and inverse agonism. Journal Biol Chem doi/10.1074, 2007.
17. Zigman J M, Jones J E, Lee C E, Saper C B, Elmquist J K. Expression of ghrelin receptor mRNA in the rat and the mouse brain. J Comparative Neurology 2006; 494:528-548.
18. Zigman K M, Nakano Y, Coppari R, Balthasar N, Marcus J N, Lee C E et al. Mice lacking ghrelin receptors resist the development of diet induced obesity. J Clin Invest 2005; 115:3564-3572.
19. Wortley K E, del Rincon J P, Murray J D, Garcia J, Lida K, Thorner M O, Sleeman M W. Absence of ghrelin protects against early-onset obesity. J Clin Invest 2005; 115:3573-3578.
20. Gelling R W, Overduin J, Morrison C D, Morton G J, Frayo R S, Cummings D E, Schwartz M W. Effect of uncontrolled diabetes on plasma ghrelin concentrations and ghrelin-induced feeding. Endocrinology 2004; 145: 4575-4582.
21. Tannenbaum G S, Epelbaum J, Bowers C Y. Interrelationship between the novel peptide ghrelin and somatostatin/GHRH in regulation of pulsatile growth hormone secretion. Endocrinology 2003; 144:967-974.
22. Tannenbaum G S, Epelbaum J, Bowers C Y. Ghrelin and growth hormone neuroendocrine axis. In: Brain Somatic Cross-Talk and the Central Control of Metabolism. Eds. C Kordon et al. 2003; Springer-Verlag, Berlin/Heidelberg pg 65-80.
23. Bowers C Y, Chang, J-K, Wu S, Linse K D, Hurley D L, Veldhuis J D. Biochemistry of growth hormone secretagogue molecules, In: Fat Loss, Wasting and Cachexia in Medicine, (Ed) Schuster M and Mantovani G, Springer Verlag, Chapter 5.7, p 219-234, 2006.
24. Bowers C Y, Laferrere B, Hurley D L, Veldhuis J D. The role of GHS/Ghrelin in Feeding and Body Composition. Obesity and Energy Metabolism: research and Clinical Applications (Eds) Conn P M and Donohoue P. The Humans Press, 2007.
25. Inui A, Asakawa A, Bowers C Y, Montovani G, Laviano A, Meguid M, Fujimiya M. Ghrelin, appetite and growth—The emerging role of the stomach as an endocrine organ. FASEB Journal 2004; 18:439-456.
26. Van der Lely A J, Tschop M, Heiman M L, Ghigo E. Biological, physiological, pathophysiological and pharmacological aspects of ghrelin. Endocrine Reviews 2004; 25:426-457.
27. Korbonits M, Goldstone A P, Gueorguiev M, Grossman A B. Ghrelin—a hormone with multiple functions. Neuroendocrinology 2004; 25:27-68.
28. Yang J, Brown M S, Liang G, Grishin N V, Goldstein J L. Identification of the acyltransferase that octanoylates ghrelin, an appetite-stimulating peptide hormone. Cell. 2008 Feb. 8; 132(3):387-96.
29. Yang J, Zhao T J, Goldstein J L, Brown M S. Inhibition of ghrelin O-acyltransferase (GOAT) by octanoylated pentapeptides. Proc Natl Acad Sci USA. 2008 Aug. 5; 105(31): 10750-5. Epub 2008 Jul. 31.

All references cited in the specification and the Examples are incorporated herein in their entirety by reference.

What is claimed is:

1. A method for treatment, prevention or management of diabetes mellitus in a subject said method comprising the step of administering an effective amount of a GOAT inhibitor and an effective amount of a ghrelin receptor antagonist to a subject in need thereof, wherein the GOAT inhibitor or the ghrelin receptor antagonist comprises an octanoylated pentapeptide and wherein the octanoylation is at position three of the pentapeptide.

2. The method of claim 1, wherein the diabetes mellitus is type I or II.

3. The method of claim 1, wherein the ghrelin receptor antagonist is administered alone, sequentially, or concomitantly with a biguanide, a peroxisome proliferator activator-receptor alpha (PPAR-alpha) ligand or PPAR-gamma ligand.

4. A method for treatment, prevention, or management of metabolic syndrome in a subject said method comprising the step of administering an effective amount of a GOAT inhibitor and an effective amount of a ghrelin receptor antagonist to a subject in need thereof, wherein the GOAT inhibitor or the ghrelin receptor antagonist comprises an octanoylated pentapeptide and wherein the octanoylation is at position three of the pentapeptide.

5. A method of treatment, prevention or management of obesity or obesity related disease or disorder in a subject, said method comprising the step of administering an effective amount of a ghrelin O-acyltransferase (GOAT) inhibitor and an effective amount of a ghrelin receptor antagonist to a subject in need thereof, wherein the GOAT inhibitor and/or the ghrelin receptor antagonist comprises an octanoylated peptide and wherein the octanoylation is at position three of the peptide.

6. The method of claim 5, further comprising an additional anti-obesity treatment.

7. The method of claim 6, wherein the additional anti-obesity treatment is a dietary restriction therapy in combination with a 5HT (serotonin) transporter inhibitor, a NE (norepinephrine) transporter inhibitor, a CB-1 (cannabinoid-1) antagonist/inverse agonist, a H3 (histamine H3) antagonist/inverse agonist, a MCH1R (melanin concentrating hormone 1R) antagonist, a MCH2R agonist/antagonist, a NPY1 antagonist, a leptin, a leptin derivative, a leptin analog, PYY (1-36), PYY(3-36), an opioid antagonist, an orexin antagonist, a BRS3 (bombesin receptor subtype 3) agonist, a CCK-A (cholecystokinin-A) agonist, a CNTF (Ciliary neurotrophic factor), a CNTF derivative, a lipase drug inhibitor, an inhibitor of food intake, an incretin, an incretin agonist, an incretin analog or an incretin mimic.

8. The method of claim 5, wherein the GOAT inhibitor and/or the ghrelin receptor antagonist comprises an octanoylated pentapeptide and wherein the octanoylation is at position three of the pentapeptide.

9. The method of claim 8, wherein the GOAT inhibitor and/or the ghrelin receptor antagonist comprises an octanoylated pentapeptide and wherein the octanoylation is on the side chain of the residue at position three of the pentapeptide.

10. The method of claim 9, wherein the octanoylated ghrelin pentapeptide is Gly-Ser-[Ser-Octanoyl$^3$]-Phe-LeuCO$_2$H (SEQ ID NO: 1), Gly-Ser-[Ser-Octanoyl$^3$]-Phe-LeuNH$_2$ (SEQ ID NO: 94), Gly-Ser-[Dap-Octanoyl$^3$]-Phe-LeuCO$_2$H (SEQ ID NO: 2), or Gly-Ser-[Dap-Octanoyl$^3$]-Phe-LeuNH$_2$ (SEQ ID NO: 95).

11. The method of claim 5, wherein the ghrelin receptor antagonist is of formula (VII): $A^{11}$-$A^{12}$-$A^{13}$-Gly-Ser-$A^{14}$-Phe-Leu-$A^{15}$-$A^{16}$-$A^{17}$-$A^{18}$(SEQ ID NO:93), wherein $A^{11}$ is absent, desamino-Tyr, an amino acid or an amino protecting group; $A^{12}$ is absent, or an amino acid; $A^{13}$ is absent, or an amino acid; each of $A^{15}$, $A^{16}$, $A^{17}$, and $A^{18}$ is absent or an amino acid, and can be the same or different; $A^{14}$ is a serine conjugated with a —C(O)C$_1$-C$_{20}$ alkyl group on the side chain OH of said serine or a diaminopropionic acid conjugated with a —C(O)C$_1$-C$_{20}$ alkyl group on one of the amino groups of said diaminopropionic acid, provided at least one of $A^{11}$, $A^{12}$, $A^{13}$ is present.

12. The method of claim 11, wherein the amino acid is selected from the group consisting of alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, valine, homocysteine, phosphoserine, phosphothreonine, phosphotyrosine, hydroxyproline, gamma-carboxyglutamate, hippuric acid, octahydroindole-2-carboxylic acid, statine, 1,2,3,4,-tetrahydroisoquinoline-3-carboxylic acid, penicillamine (3-mercapto-D-valine), ornithine, citruline, alpha-methyl-alanine, para-benzoylphenylalanine, para-aminophenylalanine, p-fluorophenylalanine, phenylglycine, propargylglycine, sarcosine, tert-butylglycine, diaminobutyric acid, 7-hydroxy-tetrahydroisoquinoline carboxylic acid, naphthylalanine, biphenylalanine, cyclohexylalanine, amino-isobutyric acid, norvaline, norleucine, tert-leucine, tetrahydroisoquinoline carboxylic acid, pipecolic acid, homophenylalanine, cyclohexylglycine, dehydroleucine, 2,2-diethylglycine, 1-amino-1-cyclopentanecarboxylic acid, 1-amino-1-cyclohexanecarboxylic acid, amino-benzoic acid, amino-naphthoic acid, gamma-aminobutyric acid, difluorophenylalanine, nipecotic acid, alpha-amino butyric acid, thienyl-alanine, t-butylglycine, aminovaleric acid, pyroglutamic acid, alpha-aminoisobutyric acid, alpha,gamma-diaminobutyric acid (αγAbu), pyridylalanine, α-naphthylalanine, β-naphthylalanine, N$^\epsilon$-picoloyl-lysine, 4-halo-Phenylalanine, 4-pyrolidylalanine, isonipecotic acid, and isomers thereof; or wherein A$^{11}$ is desamino-Tyr-.

13. The method of claim 5, wherein the ghrelin receptor antagonist is selected from the group consisting of Tyr-DTrp-DLys-Trp-DPhe-NH$_2$ (SEQ ID NO: 11), Tyr-DTrp-Lys-Trp-DPhe-NH$_2$ (SEQ ID NO: 12), His-DTrp-DLys-Trp-DPhe-NH$_2$ (SEQ ID NO: 13), His-DTrp-DLys-Phe-DTrp-NH$_2$ (SEQ ID NO: 14), His-DTrp-DArg-Trp-DPhe-NH$_2$ (SEQ ID NO: 15), His-DTrp-DLys-Trp-DPhe-Lys-NH$_2$ (SEQ ID NO: 16), DesaminoTyr-DTrp-Ala-Trp-DPhe-NH$_2$ (SEQ ID NO: 17), DesaminoTyr-DTrp-DLys-Trp-DPhe-NH$_2$ (SEQ ID NO: 18), DesaminoTyr-DTrp-Ser-Trp-DPhe-Lys-NH$_2$ (SEQ ID NO: 19), DesaminoTyr-DTrp-Ser-Trp-DPhe-NH$_2$ (SEQ ID NO: 20), His-DTrp-DTrp-Phe-Met-NH$_2$ (SEQ ID NO: 21), Tyr-DTrp-DTrp-Phe-Phe-NH$_2$ (SEQ ID NO: 22), Glyψ[CH$_2$NH]DβNal-Ala-Trp-DPhe-Lys-NH$_2$ (SEQ ID NO: 23), Glyψ[CH$_2$NH]-DβNal-DLys-Trp-DPhe-Lys-NH$_2$ (SEQ ID NO: 24), DAla-DβNal-DLys-DTrp-Phe-Lys-NH$_2$ (SEQ ID NO: 25), His-DβNal-DLys-DTrp-Phe-Lys-NH$_2$ (SEQ ID NO: 26), Ala-His-DTrp-DLys-Trp-DPhe-Lys-NH$_2$ (SEQ ID NO: 27), Alaψ[CH$_2$NH]-DβNal-Ala-Trp-DPhe-Lys-NH$_2$ (SEQ ID NO: 28), DβNal-Ala-Trp-DPhe-Ala-NH$_2$ (SEQ ID NO: 29), DAla-DcyclohexylAla-Ala-Phe-DPhe-Nle-NH$_2$ (SEQ ID NO: 30), DcyclohexylAla-Ala-Phe-DTrp-Lys-NH$_2$ (SEQ ID NO: 31), DAla-DβNal-Ala-Thr-DThr-Lys-NH$_2$ (SEQ ID NO: 32), DcyclohexylAla-Ala-Trp-DPhe-NH$_2$ (SEQ ID NO: 33), DAla-DβNal-Ala-Ala-DAla-Lys-NH$_2$ (SEQ ID NO: 34), DβNal-Ala-Trp-DPhe-Leu-NH$_2$ (SEQ ID NO: 35), His-DTrp-Phe-Trp-DPhe-Lys-NH$_2$ (SEQ ID NO: 36), DAla-DβNal-DAla-DTrp-Phe-Lys-NH$_2$ (SEQ ID NO: 37), βAla-Trp-DAla-DTrp-Phe-NH$_2$ (SEQ ID NO: 38), His-Trp-DAla-DTrp-Phe-LysNH$_2$ (SEQ ID NO: 39), DLys-Dβ-Nal-Ala-Trp-DPhe-Lys-NH$_2$ (SEQ ID NO: 40), DAla-Dβ-Nal-DLys-DTrp-Phe-Lys-NH$_2$ (SEQ ID NO: 41), Tyr-DAla-Phe-Aib-NH$_2$ (SEQ ID NO: 42), Tyr-DAla-Sar-NMePhe-NH$_2$ (SEQ ID NO: 43), αγAbu-DTrp-DTrp-Ser-NH$_2$ (SEQ ID NO: 44), αγAbu-DTrp-DTrp-Lys-NH$_2$ (SEQ ID NO: 45), αγAbu-DTrp-DTrp-Orn-NH$_2$ (SEQ ID NO: 46), αAbu-DTrp-DTrp-Orn-NH$_2$ (SEQ ID NO: 47), DThr-DαNal-DTrp-DPro-Arg-NH$_2$ (SEQ ID NO: 48), DAla-Ala-DAla-DTrp-Phe-Lys-NH$_2$ (SEQ ID NO: 49), Alaψ[CH$_2$NH]His-DTrp-Ala-Trp-DPhe-Lys-NH$_2$ (SEQ ID NO: 50), Lys-DHis-DTrp-Phe-NH$_2$ (SEQ ID NO: 51), γAbu-DTrp-DTrp-Orn-NH$_2$ (SEQ ID NO: 52), inip-Trp-Trp-Phe-NH$_2$ (SEQ ID NO: 53), Ac-DTrp-Phe-DTrp-Leu-NH$_2$ (SEQ ID NO: 54), Ac-DTrp-Phe-DTrp-Lys-NH$_2$ (SEQ ID NO: 55), Ac-DTrp-DTrp-Lys-NH$_2$ (SEQ ID NO: 56), DLys-Tyr-DTrp-DTrp-Phe-Lys-NH$_2$ (SEQ ID NO: 57), Ac-DβNal-Leu-Pro-NH$_2$ (SEQ ID NO: 58), βAla-Trp-DTrp-DTrp-Orn-NH$_2$ (SEQ ID NO: 59), DVal-DαNal-DTrp-Phe-Arg-NH$_2$ (SEQ ID NO: 60), DLeu-DαNal-DTrp-Phe-Arg-NH$_2$ (SEQ ID NO: 61), CyclohexylAla-DαNal-DTrp-Phe-Arg-NH$_2$ (SEQ ID NO: 62), DTrp-DαNal-DTrp-Phe-Arg-NH$_2$ (SEQ ID NO: 63), DAla-DβNal-DPro-Phe-Arg-NH$_2$ (SEQ ID NO: 64), Ac-Dα-Nal-DTrp-Phe-Arg-NH$_2$ (SEQ ID NO: 65), DαNal-DTrp-Phe-Arg-NH$_2$ (SEQ ID NO: 66), His-DTrp-DTrp-Lys-NH$_2$ (SEQ ID NO: 67), Ac-DβNal-DTrp-NH$_2$ (SEQ ID NO: 68), αAib-DTrp-DcyclohexylAla-NH$_2$ (SEQ ID NO: 69), αAib-DTrp-DAla-cyclohexylAla-NH$_2$ (SEQ ID NO: 70), DAla-DcyclohexylAla-Ala-Ala-Phe-DPhe-Nle-NH$_2$ (SEQ ID NO: 71), DPhe-Ala-Phe-DPal-NH$_2$ (SEQ ID NO: 72), DPhe-Ala-Phe-DPhe-Lys-NH$_2$ (SEQ ID NO: 73), DLys-Tyr-DTrp-DTrp-Phe-NH$_2$ (SEQ ID NO: 74), Ac-DLys-Tyr-DTrp-DTrp-Phe-NH$_2$ (SEQ ID NO: 75), Arg-DTrp-Leu-Tyr-Trp-Pro (cyclic Arg-Pro) (SEQ ID NO: 76), Ac-DβNal-PicLys-ILys-DPhe-NH$_2$ (SEQ ID NO: 77), DPal-Phe-DTrp-Phe-Met-NH$_2$ (SEQ ID NO: 78), DPhe-Trp-DPhe-Phe-Met-NH$_2$ (SEQ ID NO: 79), DPal-Trp-DPhe-Phe-Met-NH$_2$ (SEQ ID NO: 80), βAla-Pal-DTrp-DTrp-Orn-NH$_2$ (SEQ ID NO: 81), αγAbu-Trp-DTrp-DTrp-Orn-NH$_2$ (SEQ ID NO: 82), βAla-Trp-DTrp-DTrp-Lys-NH$_2$ (SEQ ID NO: 83), γAbu-Trp-DTrp-DTrp-Orn-NH$_2$ (SEQ ID NO: 84), Ava-Trp-DTrp-DTrp-Orn-NH$_2$ (SEQ ID NO: 85), DLys-Tyr-DTrp-Ala-Trp-DPhe-NH$_2$ (SEQ ID NO: 86), His-DTrp-DArg-Trp-DPhe-NH$_2$ (SEQ ID NO: 87), <Glu-His-Trp-DSer-DArg-NH$_2$ (SEQ ID NO: 88), DPhe-DPhe-DTrp-Met-DLys-NH$_2$ (SEQ ID NO: 89), Gly-Met-Ala-Gly-Ser-(Dap-Oct)-Phe-Leu-Ser-Pro-Glu-His-NH$_2$ (SEQ ID NO: 3), O-(2-methylallyl)benzophenone oxime, (R)-2-amino-3-(1H-indol-3-yl)-1-(4-phenylpiperidin-1-yl)propan-1-one, N—((R)-1-((R)-1-((S)-3-(1H-indol-3-yl)-1-oxo-1-(4-phenylpiperidin-1-yl)propan-2-ylamino)-6-amino-1-oxohexan-2-ylamino)-3-hydroxy-1-oxopropan-2-yl)benzamide, (S)—N—((S)-3-(1H-indol-3-yl)-1-oxo-1-(4-phenylpiperidin-1-yl)propan-2-yl)-6-acetamido-2-((S)-2-amino-3-(benzyloxy)propanamido)hexanamide, (S)—N—((R)-3-(1H-indol-3-yl)-1-oxo-1-(4-phenylpiperidin-1-yl)propan-2-yl)-2-((S)-2-acetamido-3-(benzyloxy)propanamido)-6-aminohexanamide, (R)—N-(3-(1H-indol-3-yl)-1-(4-(2-methoxyphenyl)piperidin-1-yl)-1-oxopropan-2-yl)-4-aminobutanamide, (R)—N-(3-(1H-indol-3-yl)-1-(4-(2-methoxyphenyl)piperidin-1-yl)-1-oxopropan-2-yl)-2-amino-2-methylpropanamide, methyl 3-(p-tolylcarbamoyl)-2-naphthoate, ethyl 3-(4-(2-methoxyphenyl)piperidine-1-carbonyl)-2-naphthoate, 3-(2-methoxyphenylcarbamoyl)-2-naphthoate, (S-2,4-diamino-N-((R)-3-(naphthalen-2-ylmethoxy)-1-oxo-1-(4-phenylpiperidin-1-yl)propan-2-yl) butanamide, naphthalene-2,3-diylbis((4-(2-methoxyphenyl) piperazin-1-yl)methanone), (R)-2-amino-N-(3-(benzyloxy)-1-oxo-1-(4-phenylpiperazin-1-yl)propan-2-yl)-2-methylpropanamide, or (R)-2-amino-3-(benzyloxy)-1-(4-phenylpiperazin-1-yl)propan-1-one, and pharmaceutically acceptable salts thereof.

14. A peptide consisting of the amino acid sequence of formula (VII): A$^{11}$-A$^{12}$-A$^{13}$-Gly-Ser-A$^{14}$-Phe-Leu-A$^{15}$-A$^{16}$-A$^{17}$-A$^{18}$(SEQ ID NO:93), wherein A$^{11}$ is absent, an amino acid, or an amino protecting group; A$^{12}$ is absent or an amino acid; A$^{13}$ is an amino acid; each of A$^{15}$, A$^{16}$, A$^{17}$, and A$^{18}$ is absent or an amino acid, and can be the same or different; A$^{14}$ is a serine conjugated with a —C(O)C$_1$-C$_{20}$ alkyl group on the side chain OH of said serine.

15. A peptide comprising the amino acid sequence of formula (VII): A$^{11}$-A$^{12}$-A$^{13}$-Gly-Ser-A$^{14}$-Phe-Leu-A$^{15}$-A$^{16}$-A$^{17}$-A$^{18}$ (SEQ ID NO: 93), wherein A$^{11}$ is absent, an amino acid, or an amino protecting group; A$^{12}$ is absent or an amino acid; A$^{13}$ is absent or an amino acid; each of A$^{15}$, A$^{16}$, A$^{17}$, and A$^{18}$ is absent or an amino acid, and can be the same or different; A$^{14}$ is a diaminopropionic acid conjugated with a —C(O)C$_1$-C$_{20}$ alkyl group on one of the amino groups of said diaminopropionic acid, provided that at least one of A$^{11}$, A$^{12}$, A$^{13}$ is present.

* * * * *